US008242166B2

(12) United States Patent
Vu et al.

(10) Patent No.: US 8,242,166 B2
(45) Date of Patent: Aug. 14, 2012

(54) C(10) ETHYL ESTER AND C(10) CYCLOPROPYL ESTER SUBSTITUTED TAXANES

(75) Inventors: Phong Vu, Tallahassee, FL (US); Robert A. Holton, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 541 days.

(21) Appl. No.: 12/409,884

(22) Filed: Mar. 24, 2009

(65) Prior Publication Data
US 2009/0318543 A1 Dec. 24, 2009

Related U.S. Application Data

(60) Provisional application No. 61/014,017, filed on Mar. 31, 2008.

(51) Int. Cl.
A61K 31/44 (2006.01)
C07D 305/14 (2006.01)
C07D 405/12 (2006.01)

(52) U.S. Cl. .......................... 514/449; 549/510; 549/511

(58) Field of Classification Search .................. 549/510, 549/511
See application file for complete search history.

(56) References Cited

U.S. PATENT DOCUMENTS

| | | |
|---|---|---|
| 4,814,470 A | 3/1989 | Colin et al. |
| 5,175,315 A | 12/1992 | Holton |
| 5,200,534 A | 4/1993 | Rao |
| 5,227,400 A | 7/1993 | Holton et al. |
| 5,243,045 A | 9/1993 | Holton et al. |
| 5,250,683 A | 10/1993 | Holton et al. |
| 5,254,580 A | 10/1993 | Chen et al. |
| 5,274,124 A | 12/1993 | Holton |
| 5,283,253 A | 2/1994 | Holton et al. |
| 5,350,866 A | 9/1994 | Holton et al. |
| 5,367,086 A | 11/1994 | Rao |
| 5,407,674 A | 4/1995 | Gabetta et al. |
| 5,430,160 A | 7/1995 | Holton |
| 5,475,011 A | 12/1995 | Ojima et al. |
| 5,556,878 A | 9/1996 | Kelly et al. |
| 5,567,614 A | 10/1996 | Patel et al. |
| 5,614,645 A | 3/1997 | Kingston et al. |
| 5,714,512 A | 2/1998 | Bastart et al. |
| 5,714,513 A | 2/1998 | Holton et al. |
| 5,721,268 A | 2/1998 | Holton et al. |
| 5,739,362 A | 4/1998 | Holton et al. |
| 5,756,776 A | 5/1998 | Bombardelli et al. |
| 5,767,297 A | 6/1998 | Mandai et al. |
| 5,780,653 A | 7/1998 | Tao et al. |
| 5,811,452 A | 9/1998 | Ojima et al. |
| 5,879,929 A | 3/1999 | Patel |
| 5,889,043 A | 3/1999 | Bouchard et al. |
| 5,906,990 A | 5/1999 | Bouchard et al. |
| 5,912,264 A | 6/1999 | Wittman et al. |
| 5,959,125 A | 9/1999 | Bouchard et al. |
| 5,965,739 A | 10/1999 | Kelly et al. |
| 6,025,385 A | 2/2000 | Shimizu et al. |
| 6,136,808 A | 10/2000 | Abe et al. |
| 6,156,789 A | 12/2000 | Bissery et al. |
| 6,268,381 B1 | 7/2001 | Shimizu et al. |
| 6,369,244 B1 | 4/2002 | Holton et al. |
| 6,638,973 B2 | 10/2003 | Holton |
| 6,649,632 B2 | 11/2003 | Holton |
| 6,660,866 B2 | 12/2003 | Holton |
| 6,780,879 B2 | 8/2004 | Holton |
| 2001/0002404 A1 | 5/2001 | Webb et al. |

FOREIGN PATENT DOCUMENTS

| | | |
|---|---|---|
| EP | 0 534 709 A1 | 3/1993 |
| EP | 0 558 959 B1 | 9/1993 |
| EP | 0 590 267 A2 | 4/1994 |
| EP | 0 590 267 A3 | 4/1994 |
| EP | 0 600 517 B1 | 6/1994 |
| EP | 0 604 910 B1 | 7/1994 |
| EP | 0 629 701 A1 | 12/1994 |
| EP | 0 639 577 A1 | 2/1995 |
| EP | 0 882 732 A1 | 12/1998 |
| WO | 93/06079 A1 | 4/1993 |
| WO | 93/18018 A1 | 9/1993 |
| WO | 93/23389 A1 | 11/1993 |
| WO | 94/07880 A1 | 4/1994 |
| WO | 94/13655 A1 | 6/1994 |
| WO | 94/20484 A1 | 9/1994 |
| WO | 95/04154 A1 | 2/1995 |
| WO | 96/13495 A1 | 5/1996 |
| WO | 96/14308 A1 | 5/1996 |
| WO | 96/30356 A1 | 10/1996 |
| WO | 97/07110 A1 | 2/1997 |
| WO | 97/09979 A1 | 3/1997 |
| WO | 97/32578 A1 | 9/1997 |
| WO | 97/42181 A1 | 11/1997 |
| WO | 97/44026 A1 | 11/1997 |
| WO | 97/44063 A1 | 11/1997 |
| WO | 98/02426 A1 | 1/1998 |
| WO | 99/09021 A1 | 2/1999 |

(Continued)

OTHER PUBLICATIONS

Alley et al., Human Tumor Xenograft Models in NCI Drug Development, Anticancer Drug Development Guide, pp. 125-152 (Humana Press, Totowa, NJ, 2004).

Appendino et al. "Synthesis of Paclitaxel (Docetaxel) / 2-Deacetoxytaxinine J Dimers" Tetrahedron, vol. 55 (1999) pp. 6567-6576.

Burger et al., Screening Using Animal Systems, Anticancer Drug Development, pp. 285-299 (Academic Press, San Diego, CA, 2002).

Cravallee et al. "Methyleniminium Salts as Acylating Agent—One Step Synthesis of Baccatin III from 10-Deacetylbaccatin III with High Selectivity" Tetrahedron Letters, vol. 39 (1998) pp. 4263-4266.

Dubois et al. "Fluorescent and Biotinylated Analogues of Docetaxel: Synthesis and Biological Evaluation" Bioorganic & Medicinal Chemistry, vol. 3, No. 10 (1995) pp. 1357-1368.

(Continued)

*Primary Examiner* — Noble Jarrell
*Assistant Examiner* — Raymond Covington
(74) *Attorney, Agent, or Firm* — Bryan Cave LLP

(57) ABSTRACT

Taxanes having an ethyl ester or cyclopropyl ester substituent at C(10), a keto substituent at C(9), a hydroxy substituent at C(7), a thienyl substituent at C(3') and a cyclobutyloxycarbamate or cyclopentyloxycarbamate substituent at C(3'), pharmaceutical compositions comprising such taxanes, methods of treatment and administration, and methods of preparation of medicaments comprising the taxanes.

20 Claims, 17 Drawing Sheets

FOREIGN PATENT DOCUMENTS

| | | |
|---|---|---|
| WO | 99/14209 A1 | 3/1999 |
| WO | 99/32473 A1 | 7/1999 |
| WO | 00/53592 A1 | 9/2000 |
| WO | 01/57013 A1 | 8/2001 |
| WO | 01/57032 A1 | 8/2001 |
| WO | 01/68089 A1 | 9/2001 |
| WO | 2006/088767 A2 | 8/2006 |
| WO | 2008/013785 A2 | 1/2008 |

OTHER PUBLICATIONS

Fiebig et al., Human Tumor Xenografts and Explants, Tumor Models in Cancer Research 113-137 (Humana Press, Totowa, NJ, 2002).

Guenard et al. "Effects of the Hydrophobicity of Taxoids on Their Interaction with Tubulin" Bioorganic & Medicinal Chemistry, vol. 8 (2000) pp. 145-156.

Gueritte-Voegelein et al. "Relationships between the Structure of Taxol Analogues and Their Antimitotic Activity" Journal of Medicinal Chemistry, vol. 34, No. 3 (1991) pp. 992-998.

Ishihara et al. "Scandium Trifluoromethanesulfonate as an Extremely Active Acylation Catalyst" J. Am. Chem. Soc., vol. 117, No. 15 (1995) pp. 4413-4414.

Journal of Chinese Universities, vol. 21:3, (2000), pp. 401-406.

Journal of Tianjin University, vol. 33:1, (200), pp. 51-55.

Kant et al. "A Chemoselective Approach to Functionalize the C-10 Position of 10-Deacetylbaccatin III. Synthesis and Biological Properties of Novel C-10 Taxol Analogues" Tetrahedron Letters, vol. 35, No. 30 (1994) pp. 5543-5546.

Kingston et al., Bioactivity of Taxol and Other Taxoids, Progress in the Chemistry of Organic Natural Products 160-165 (Springer-Verlag, New York, 1993).

Kirikae et al. "Structural Significance of the Acyl Group at the C-10 Position and the A Ring of the Taxane Core of Paclitaxel for Inducing Nitric Oxide and Tumor Necrosis Factor Production by Murine Macrophages" FEBS Letters, vol. 478 (2000) pp. 221-226.

Kirikae et al. "Structural Requirements of Taxoids for Nitric Oxide and Tumor Necrosis Factor Production by Murine Macrophages" Biochemical and Biophysical Research Communications, vol. 227 (1996) pp. 227-235 (Article No. 1494).

Kobayashi et al. "Modulation of Multidrug Resistance by Taxuspine C and Other Taxoids from Japanese Yew" Bioorganic & Medicinal Chemistry Letters, vol. 8 (1998) pp. 1555-1558.

Lin et al. "Synthesis of Highly Potent Second-Generation Taxoids Through Effective Kinetic Resolution Coupling of Racemic G3-Lactams with Baccatins" Chirality, vol. 12, No. 5/6 (2000) pp. 431-441.

Longley et al., In Vivo Efficacy of TL-310, Presented at 97th Annual Meeting of American Association for Cancer Research on Apr. 1-5, 2006.

Longley et al., In vitro mechanism of action studies with the taxane analog, TL-909 (MST-997), Abstract Presented at the 95th Annual Meeting of the American Association for Cancer Research, Orlando, FL, Mar. 27-31, 2004.

Longley et al., In vitro mechanism of action studies with the taxane analog, TL-310, Abstract Presented at the 96th Annual Meeting of the American Association for Cancer Research, Anaheim, CA, Apr. 16-20, 2005.

McFadyen, et al., "Cytochrome P450 CYP1B1 protein expression: a novel mechanism of anticancer drug resistance" Biochemical Pharmacology 62 (2001) 207-212.

Ojima et al. "Synthesis and Structure—Activity Relationships of the Second-Generation Antitumor Taxoids: Exceptional Activity Against Drug-Resistant Cancer Cells" J. Med. Chem., vol. 39, No. 20 (1996) pp. 3889-3896.

Ojima et al. "Synthesis and Biological Activity of Novel 3'-Trifluoromethyl Taxoids" Bioorganic & Medicinal Chemistry, vol. 7, No. 2 (1997) pp. 133-138.

Ojima et al. "Synthesis of Novel 3'-Trifluoromethyl Taxoids Through Effective Kinetic Resolution of Racemic 4-CF3-β-Lactams With Baccatins" Chirality, vol. 9 (1997) pp. 487-494.

Ojima et al. "Efficient Asymmetric Synthesis of β-Lactams Bearing a Cyclopropane or an Epoxide Moiety and Their Application to the Synthesis of Novel Isoserines and Taxoids" Journal of Organic Chemistry, vol. 63, No. 2 (1998) pp. 224-225.

Ojima et al. "New Photoaffinity Analogs of Paclitaxel" Bioorganic & Medicinal Chemistry Letters, vol. 9 (1999) pp. 1189-1194.

Ojima et al. "Enantiopure Fluorine-Containing Taxoids: Potent Anticancer Agents and Versatile Probes for Biomedical Problems" Journal of Fluorine Chemistry, vol. 97 (1999) pp. 3-10.

Ojima et al. Synthesis and Structure-Activity Relationships of New Second-Generation Taxoids, Bioorganic & Medicinal Chemistry Letters, vol. 9 (1999) pp. 3423-3428.

Ojima et al. "Synthesis and Biological Activity fo C-3'-Difluoromethyl-Taxoids" Bioorganic & Medicinal Chemistry, vol. 8, No. 7 (2000) pp. 1619-1628.

Rao et al. "Synthesis and Evaluation of Some 10-Mono- and 2',10-Diesters of 10-Deacetylpaclitaxel" J. Med. Chem., vol. 38, No. 17 (1995) pp. 3411-3414.

Rygaard et al., Heterotransplantation of a Human Malignant Tumor to "Nude" Mice, Acta Path. Microbiol. Scand. 77, 758-760, 1969.

Sampath et al., Preclinical Pharmacologic Evaluation of MST-997, an Orally Active Taxane with Superior in Vitro and in Vivo Efficacy in Paclitaxel- and Docetaxel-Resistant Tumor Models, Clinical Cancer Research 12(11), 3459-3469, 2006.

Sengupta et al. "Probing the Environment of Tubulin-Bound Paclitaxel Using Fluorescent Paclitaxel Analogues" Biochemistry, vol. 36, No. 17 (1997) pp. 5179-5184.

Senilh et al. "Mise en evidence de nouveaux analogues du taxol extraits de taxus baccata" Journal of Natural Products, vol. 47, No. 1 (Jan./Feb. 1984) pp. 131-137.

Shi et al. "Studies on the Quantitative Structure-activity Relationships of Paclitaxel Analogues" Gaodeng Xuexiao Huaxue Xuebao, vol. 21, No. 3 (2000) pp. 401-406. (English Abstract attached).

Straubinger et al. "Pharmacology and Antitumor Effect of Novel Paclitaxel Formulations" Chapter 8, Edited by G. Georg et al., Taxane Anticancer Agents, Basic Science and Current Status, ACS Symposium Series 583, 207th National Meeting of the American Chemical Society, San Diego, CA (1994) pp. 111-123.

Suggitt et al., 50 Years of Preclinical Anticancer Drug Screening: Empirical to Target-Driven Approaches, Clin. Cancer Res. 11, 971-981, 2005.

International Search Report for PCT/US2009/038119 dated Nov. 9, 2009.

C(10) ETHYL ESTER AND C(10) CYCLOPROPYL ESTER SUBSTITUTED TAXANES

REFERENCE TO RELATED APPLICATIONS

This application claims the benefit of U.S. Provisional Application Ser. No. 61/041,017, filed on Mar. 31, 2008, which is hereby incorporated by reference in its entirety, including any figures, tables, and drawings.

BACKGROUND

The present disclosure is directed to novel taxanes having utility as anti-tumor agents.

The taxane family of terpenes, of which baccatin III and paclitaxel, also commonly referred to as Taxol®, are members, has been the subject of considerable interest in both the biological and chemical arts. Paclitaxel itself is employed as a cancer chemotherapeutic agent and possesses a broad range of tumor-inhibiting activity. Paclitaxel has a 2'R, 3'S configuration and the following structural formula:

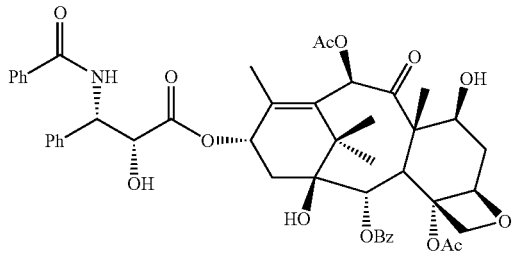

wherein Ac is acetyl, Bz is benzoyl, and Ph is phenyl.

Colin et al. reported in U.S. Pat. No. 4,814,470 that certain paclitaxel analogs have an activity significantly greater than that of paclitaxel. One of these analogs, commonly referred to as docetaxel (also known as Taxotere®), has the following structural formula:

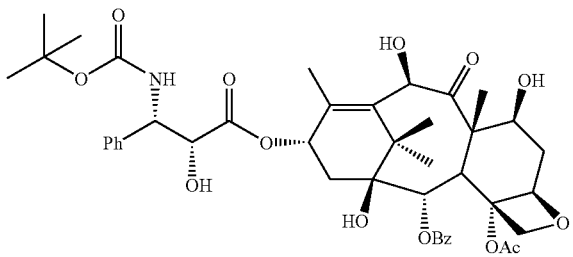

wherein Ac is acetyl, Bz is benzoyl, and Ph is phenyl.

Although paclitaxel and docetaxel are useful chemotherapeutic agents, there are limitations to their effectiveness, including limited efficacy against certain types of cancers and toxicity to subjects when administered at various doses. Further, certain tumors have shown resistance to paclitaxel and/or docetaxel. Accordingly, a need remains for additional chemotherapeutic agents with less toxicity and improved efficacy with respect to paclitaxel and/or docetaxel resistant and non-resistant tumors.

SUMMARY OF THE DISCLOSURE

Among the various aspects of the present disclosure, therefore, is the provision of taxanes which compare favorably to paclitaxel and docetaxel with respect to toxicity and to efficacy as an anti-tumor agent. In general, these taxanes posses an ethyl ester or cyclopropyl ester substituent at C(10), a keto substituent at C(9), a hydroxy substituent at C(7), a thienyl substituent at C(3'), and a cyclobutyloxycarbamate or cyclopentyloxycarbamate substituent at C(3').

Briefly, therefore, the present disclosure is directed to taxanes, per se, to prodrugs thereof, to pharmaceutical compositions comprising the taxanes (and prodrugs thereof) and a pharmaceutically acceptable carrier, to methods of treatment and administration, and to methods of preparation of medicaments comprising the taxanes (and prodrugs thereof).

In one particular aspect, the present disclosure is directed to a taxane having the structure (1):

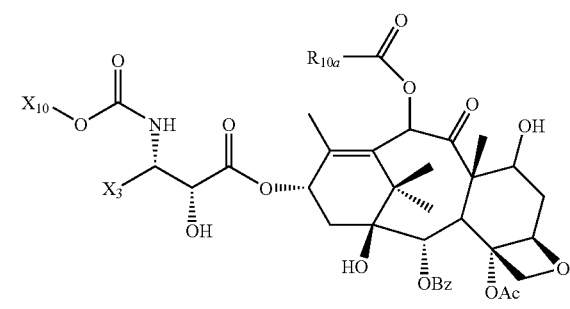

wherein $R_{10a}$ is ethyl or cyclopropyl; $X_3$ is thienyl; and $X_{10}$ is cyclobutyl or cyclopentyl.

In another particular aspect, the present disclosure is directed to a pharmaceutical composition comprising the taxane of structure (1) and at least one pharmaceutically acceptable carrier.

In another particular aspect, the present disclosure is directed to a method of inhibiting tumor growth in a mammal, the method comprising administering to the mammal a therapeutically effective amount of a pharmaceutical composition comprising the taxane of structure (1) and at least one pharmaceutically acceptable carrier. In a particular embodiment, the tumor is a multidrug resistant tumor.

Other objects and features will be in part apparent and in part pointed out hereinafter.

DETAILED DESCRIPTION

Figure 1:
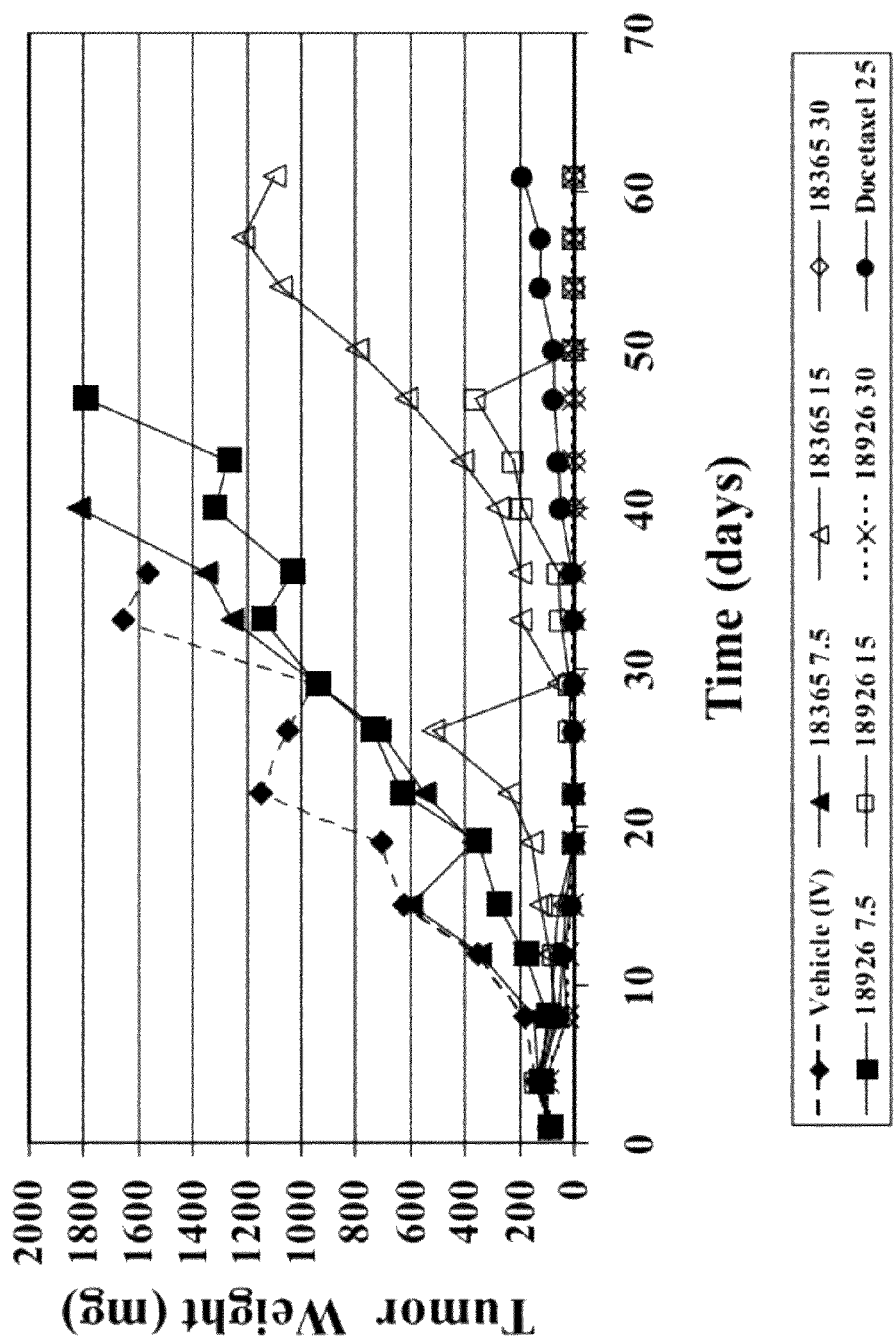
FIG. 1 depicts mean tumor growth curves for mice treated with compounds 18926, 18365, and docetaxel in the MX1 study (e219R1) (i.v. single dose).

The taxanes of the present disclosure have the following chemical structure (1):

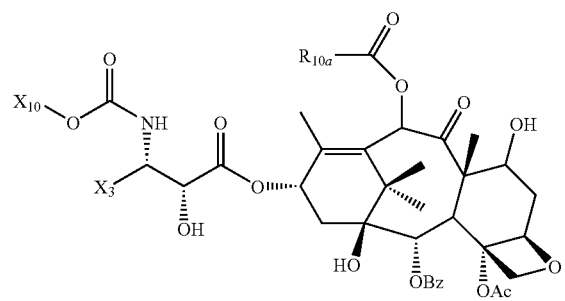

(1)

wherein $R_{10a}$ is ethyl or cyclopropyl; $X_3$ is thienyl; and $X_{10}$ is cyclobutyl or cyclopentyl.

As noted above in connection with Formula (1), $X_3$ is thienyl. Thus, for example, $X_3$ may be 2-thienyl or 3-thienyl. In a preferred embodiment, $X_3$ is 2-thienyl.

In combination, in certain embodiments in which the taxane corresponds to Formula (1), $R_{10a}$ is ethyl and $X_{10}$ is cyclobutyl or cyclopentyl; thus, for example, $R_{10a}$ can be ethyl and $X_{10}$ can be cyclobutyl, or $R_{10a}$ can be ethyl and $X_{10}$ can be cyclopentyl. In other embodiments in which the taxane corresponds to Formula (1), $R_{10a}$ is cyclopropyl and $X_{10}$ is cyclobutyl or cyclopentyl; thus, for example, $R_{10a}$ can be cyclopropyl and $X_{10}$ can be cyclobutyl, or $R_{10a}$ can be cyclopropyl and $X_{10}$ can be cyclopentyl. In each of these embodiments, $X_3$ is thienyl (e.g., 2-thienyl or 3-thienyl); more preferably in these embodiments, $X_3$ is 2-thienyl.

In other combinations, in certain embodiments in which the taxane corresponds to Formula (1), $R_{10a}$ is ethyl or cyclopropyl and $X_{10}$ is cyclobutyl; thus, for example, $R_{10a}$ can be ethyl and $X_{10}$ can be cyclobutyl, or $R_{10a}$ can be cyclopropyl and $X_{10}$ can be cyclobutyl. In other embodiments in which the taxane corresponds to Formula (1), $R_{10a}$ is ethyl or cyclopropyl and $X_{10}$ is cyclopentyl; thus, for example, $R_{10a}$ can be ethyl and $X_{10}$ can be cyclopentyl, or $R_{10a}$ can be cyclopropyl and $X_{10}$ can be cyclopentyl. In each of these embodiments, $X_3$ is thienyl (e.g., 2-thienyl or 3-thienyl); more preferably in these embodiments, $X_3$ is 2-thienyl.

In general, the C(7) hydroxy substituent and the C(10) cyclopropylcarbonyloxy or ethylcarbonyloxy substituent can independently have the alpha or beta stereochemical configuration. When the taxane compound corresponds to chemical structure (1), therefore, the C(7) and C(10) substituents can each have the alpha stereochemical configuration, the C(7) and C(10) substituents can each have the beta stereochemical configuration, the C(7) substituent can have the beta stereochemical configuration while the C(10) substituent has the alpha stereochemical configuration, or the C(7) substituent can have the alpha stereochemical configuration while the C(10) substituent has the beta stereochemical configuration, Thus, for example, in various embodiments the taxanes may correspond to one or more of the following formulae showing stereochemical configurations for the relevant portion of the chemical structure:

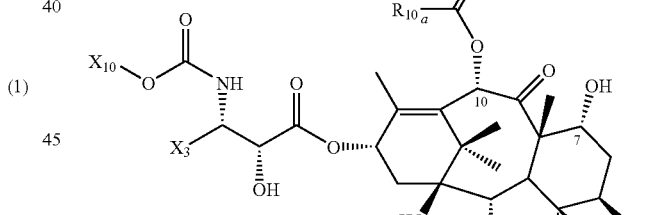

(1aa)

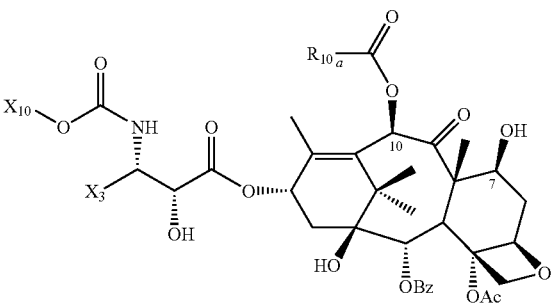

(1bb)

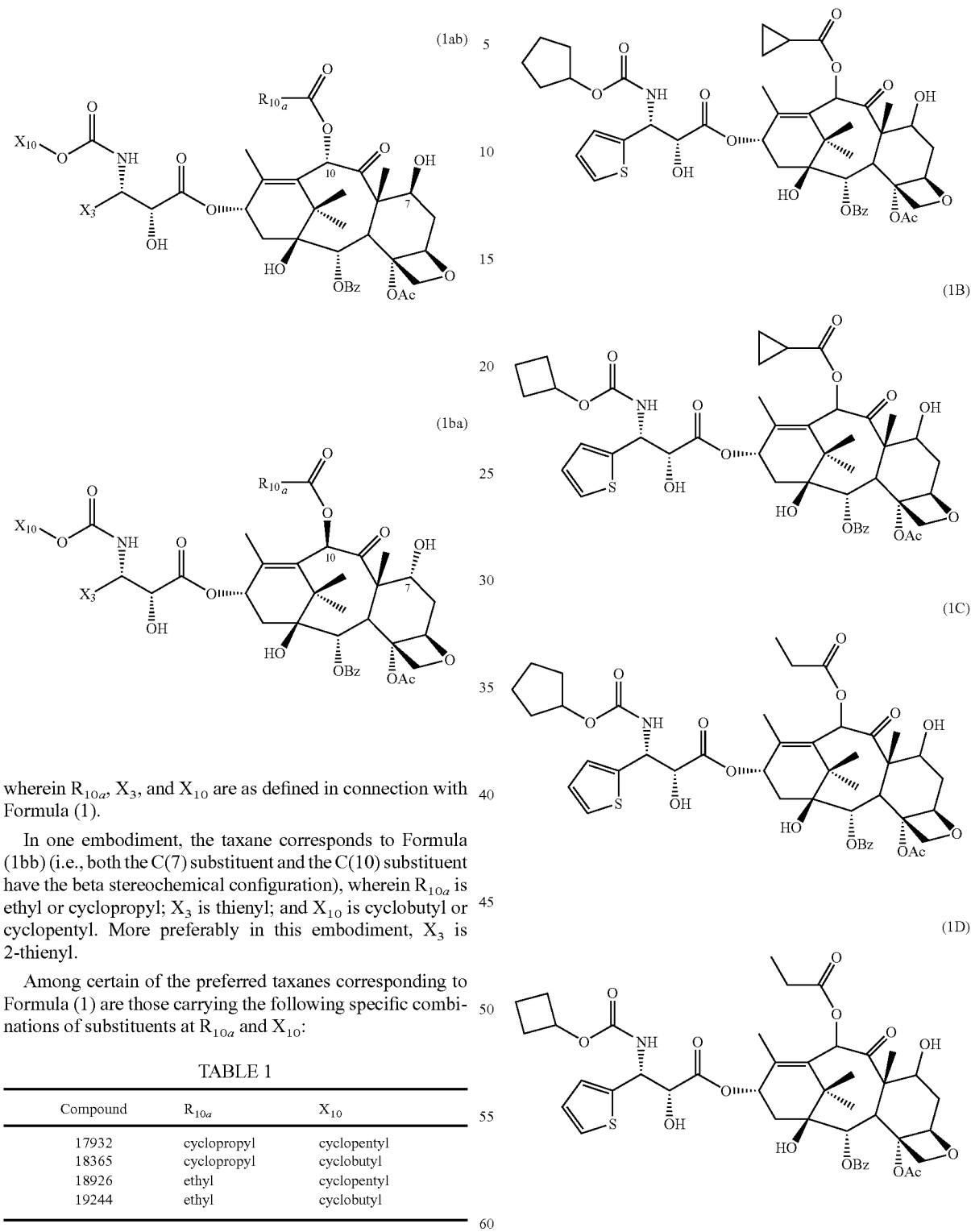

wherein $R_{10a}$, $X_3$, and $X_{10}$ are as defined in connection with Formula (1).

In one embodiment, the taxane corresponds to Formula (1bb) (i.e., both the C(7) substituent and the C(10) substituent have the beta stereochemical configuration), wherein $R_{10a}$ is ethyl or cyclopropyl; $X_3$ is thienyl; and $X_{10}$ is cyclobutyl or cyclopentyl. More preferably in this embodiment, $X_3$ is 2-thienyl.

Among certain of the preferred taxanes corresponding to Formula (1) are those carrying the following specific combinations of substituents at $R_{10a}$ and $X_{10}$:

TABLE 1

| Compound | $R_{10a}$ | $X_{10}$ |
|---|---|---|
| 17932 | cyclopropyl | cyclopentyl |
| 18365 | cyclopropyl | cyclobutyl |
| 18926 | ethyl | cyclopentyl |
| 19244 | ethyl | cyclobutyl |

In each of the combinations noted in Table 1 above (i.e., for Compounds 17932, 18365, 18926, 19244), the $X_3$ substituent of the taxane is thienyl. More preferably in these combinations, $X_3$ is 2-thienyl. Thus, for example, certain of the preferred taxanes correspond to one or more of Formulae (1A), (1B), (1C), or (1D):

In the embodiments in which both the C(7) substituent and the C(10) substituent of the taxanes corresponding to Formulae (1A), (1B), (1C), and (1D) have the beta stereochemical configuration, for example, these taxanes correspond to Formulae (1 AA), (1 BB), (1 CC), or (1 DD), respectively:

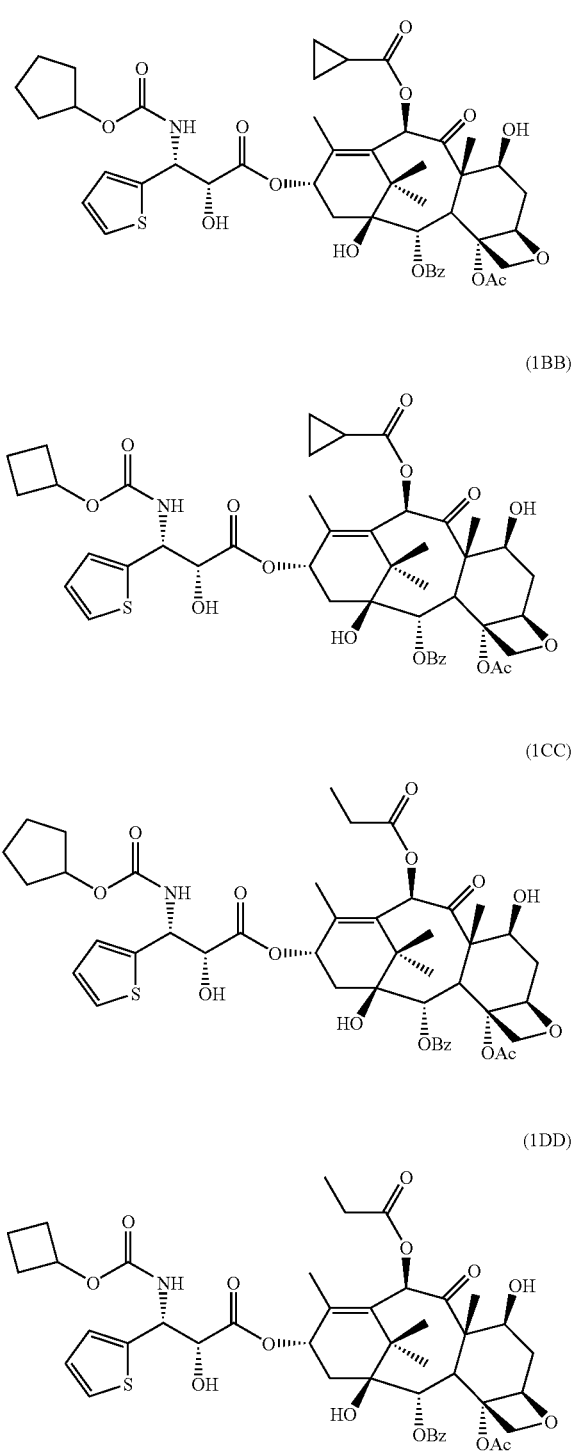

(1AA)

(1BB)

(1CC)

(1DD)

Chemotherapy using conventional chemotherapeutic agents is often hindered by the development of multidrug resistance (MDR) in tumor cells, whereby the tumor cells acquire cross-resistance to a variety of structurally and functionally unrelated compounds. Common forms of multidrug resistance have been attributed to, among other mechanisms anti-angiogenesis; overexpression of drug-efflux transporters (i.e., drug-efflux pumps); acquired mutations of the drug binding site of tubulin; differential expression of tubulin isoforms; alteration in apoptotic mechanisms; microtubule bundling and polymerization (e.g., leading to $G_2/M$ arrest and apoptosis); and activation of growth factor pathways. While the contribution of each one or more of these (and other) mechanisms of multidrug resistance remains uncertain, correlations have been made between multidrug resistance and drug-efflux transporter expression levels in various tumor types. See, e.g., Dumontet et al., J. Clin. Oncol. 17, 1061-1070 (1999); Gottesman et al., Nat. Rev. Cancer 2, 48-58 (2002).

The compounds of the present disclosure are efficacious against multidrug resistant tumors, including paclitaxel- and docetaxel-resistant tumors. Thus, in particular aspects, the compounds described herein can be used in methods for inhibiting tumor growth in a mammal, the tumor being a multidrug resistant tumor (i.e., a tumor including tumor cells exhibiting multidrug resistance). Additionally or alternatively, the tumor may be resistant to one or more conventional chemotherapeutic agents. For instance, the tumor may be resistant to carboplatin, docetaxel, doxorubicin, gemcitabine, irinotecan, paclitaxel, pemetrexed, and vincristine, among other agents. In a particular embodiment, the tumor is resistant to paclitaxel, resistant to docetaxel, or resistant to both paclitaxel and docetaxel.

In various embodiments, for example, the multidrug resistant tumor cells overexpress a drug-efflux transporter. Among particular drug-efflux transporters, the overexpression of ATP-binding cassette transporters such as P-glycoprotein (P-gp), MDR-associated protein(s) (e.g., MDR-1, MDR-2, MDR-3, among others), breast cancer resistance protein(s) (e.g., BCRP1), and/or multidrug resistance-associated protein(s) (MRPs) (e.g., MRP-1, MRP-2, MRP-3, MRP-9, among others) has been implicated in the mediation of multidrug resistance in tumor cells. Thus, in one embodiment, the overexpressed drug-efflux transporter is an ATP-binding cassette transporter. More typically in this embodiment, the drug-efflux transporter is P-glycoprotein, an MDR-associated protein, a breast cancer resistance protein, a multidrug resistance-associated protein, or a combination thereof. In these embodiments, the compounds can be efficacious against a wide variety of tumor types, including epithelial cell carcinomas such as brain, breast, colon, kidney, liver, lung (including non-small cell lung carcinomas), ovarian, pancreatic, renal, and skin tumor types. Unlike paclitaxel or docetaxel, for example, compounds 17932, 18365, 18926, and 19244 are highly effective at inhibiting the growth of tumor cells that overexpress MDR-associated proteins (e.g., MDR-1) such as, for example, DLD-1 colon carcinoma and 786-0 renal carcinoma cell lines. By way of another example, compounds 18926, 18365, 19244 are highly effective (as compared to paclitaxel and docetaxel) at inhibiting the growth of tumor cells that overexpress MRP-2 and BCRP1 such as, for example, MSTO-211H mesothelioma cells. By way of another example, compounds 18926, 18365, 19244 are highly effective (as compared to paclitaxel and docetaxel) at inhibiting the growth of tumor cells that overexpress MRP-9 such as, for example, A375 melanoma. Without being bound to one particular theory, it is believed that the basis for these improved effects over conventional chemotherapeutic agents such as paclitaxel and docetaxel is due, at least in part, to the reduced interaction of the compounds with these and other drug-efflux pumps.

Advantageously, and without regard to the particular mechanism(s) involved, the compounds described herein are effective against cancers both in vitro and in vivo in a manner superior to conventionally used taxanes with respect to certain tumor types, including paclitaxel- and/or docetaxel-sensitive and -resistant tumor lines. Whether or not used in combination with other agents, pharmaceutical compositions comprising compounds 17932, 18365, 18926, and/or 19244 may be used to treat those cancers indicated for treatment with paclitaxel and docetaxel (Taxol® and Taxotere®, respectively). Surprisingly, the compounds exhibit activity several orders of magnitude higher than that of paclitaxel and/or docetaxel (e.g., 2×, 5×, 10×, or higher) against a wide variety of tumor types (including, for example, those originating from brain, colon, lung, ovarian, pancreatic, renal, and skin cancers). Without being limiting, pharmaceutical compositions comprising compounds 17932, 18365, 18926, and/or 19244 may be used, either solely or in combination, to treat brain cancer, breast cancer, colon cancer, lung cancer (including non-small cell lung cancer), ovarian cancer, pancreatic cancer, prostate cancer, AIDS-related Kaposi's sarcoma, mesothelioma, gastric cancer, and renal cancer. The compound(s) is/are reasonably well tolerated whether administered orally or intravenously and can be effective as a single dose or multiple doses with improved toxicity profiles. The compounds of the present disclosure are also efficacious in non-Cremophor® vehicles.

Compounds 17932, 18365, 18926, and/or 19244 are highly efficacious in a number of human tumor nude mouse xenograft models, including those which are refractory/resistant to paclitaxel and docetaxel. Compounds 17932, 18365, 18926, and/or 19244 can be effectively dosed via the intravenous and oral routes on a single or multidose schedule. In the majority of xenograft models tested, the compounds show superior efficacy to paclitaxel and docetaxel when administered as an oral dose and on a multi-dose schedule, either every 4 days or every 7 days. Compounds 17932, 18365, 18926, and 19244 show a wide therapeutic index in these mouse xenograft models. Doses well below the maximum tolerated dose, as indicated by body weight loss, still maintain efficacy. The compounds display superior bioavailability orally as demonstrated by efficacy observed in xenograft models and in a favorable toxicity profile when dosed both orally and intravenously in Sprague-Dawley rats. For instance, the compounds have markedly less neurotoxicity (e.g., as measured by axonal degeneration), as compared to paclitaxel and docetaxel. The superior efficacy, lower toxicity, wide therapeutic index in multiple dosing regimens suggests an opportunity for increased dose intensity in the clinic particularly when dosed weekly in human studies. For instance, the compounds of the present disclosure could be dosed on an every three week schedule (similar to paclitaxel and docetaxel), or could be dosed on a weekly schedule. A weekly dosing schedule, for example, can allow an increase in dosing density and, for oral dosing in particular, improved patient convenience. Such oral dosing regimes could be accomplished on a daily basis with relatively low doses. Advantageously, these and other oral dosing regimes could be used as part of an anti-angiogenesis metronomic dosing schedule (which is undesirable for paclitaxel and docetaxel, as they are relatively ineffective in oral doses).

The taxanes of the present disclosure may be obtained by treatment of a β-lactam with an alkoxide having the taxane tetracyclic nucleus and a C(13) metallic oxide substituent to form compounds having a β-amido ester substituent at C(13) (as described more fully in Holton, U.S. Pat. No. 5,466,834 (hereby incorporated by reference herein in its entirety)), followed by removal of the hydroxy protecting groups. In general, β-lactams employed in these methods correspond to formula (I):

wherein $P_2$ is a hydroxy protecting group, $X_3$ is thienyl (e.g., 2-thienyl), and $X_5$ is cyclobutyloxycarbonyl or cyclopentyloxycarbonyl and the alkoxide corresponds to formula (II):

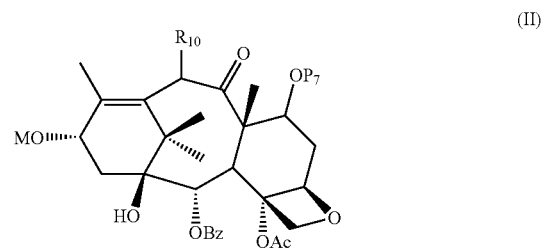

wherein M is metal or ammonium, $P_7$ is hydrogen or a hydroxy protecting group, $R_{10}$ is cyclopropylcarbonyloxy or propionyloxy, Ac is acetyl, and Bz is benzoyl.

The alkoxide of structural formula (II) may be prepared from 10-deacetylbaccatin III (10-DAB) (or a derivative thereof) by selective protection of the C(7) hydroxy group and then esterification of the C(10) hydroxy group followed by treatment with a metallic amide. In one embodiment of the present disclosure, the C(7) hydroxy group of 10-DAB is selectively protected with a silyl group as described, for example, by Denis et al. (J. Am. Chem. Soc., 1988, 110, 5917) (hereby incorporated by reference herein in its entirety).

Alternatively, the C(10) hydroxy group of a taxane can be selectively acylated in the absence of a base, as described, for example in Holton et al., U.S. Pat. No. 7,288,665 (hereby incorporated by reference herein in its entirety). Acylating agents which may be used for the selective acylation of the C(10) hydroxy group of a taxane include substituted or unsubstituted alkyl or aryl anhydrides. While the acylation of the C(10) hydroxy group of the taxane will proceed at an adequate rate for many acylating agents, it has been discovered that the reaction rate may be increased by including a Lewis acid in the reaction mixture. Preferred Lewis acids include zinc chloride, stannic chloride, cerium trichloride, cuprous chloride, lanthanum trichloride, dysprosium trichloride, and ytterbium trichloride. Zinc chloride or cerium trichloride is particularly preferred when the acylating agent is an anhydride.

In a preferred one-pot protocol, a solution of 10-DAB in N,N-dimethylformamide was treated with a stoichiometric amount of a silylating agent in the presence of 2 to 3 equivalents of 4-N,N-dimethylaminopyridine to protect the C(7) hydroxyl group, followed by treatment with an acylating agent (propionyl chloride or cyclopropylcarbonyl chloride) to selectively acylate the C(10) hydroxyl group at ambient temperature. This process reduces the production time and solvent requirements. See, e.g., U.S. Published Patent Application No. 2005/0228037 to Holton et al. (hereby incorporated by reference herein in its entirety).

It will be understood that compounds having particular stereochemical configurations at the C(7) and C(10) substituents (e.g., compounds 1aa, 1bb, 1ab, and 1ba, above) may be prepared using starting materials (e.g., 10-DAB) or intermediates having these stereochemical configurations. The preparation of C(7)-epimers of 10-DAB, for example, are illustrated by Georg et al., Journal of Organic Chemistry, 63, 8926-8934 (1998) (hereby incorporated by reference herein in its entirety). The preparation of 10-alpha 10-DAB, for example, is illustrated by Appendino et al., Tetrahedron Letters 36, 18, 3233-3236 (1995) (hereby incorporated by reference herein in its entirety). Thus, the stereochemical configuration of the C(7) position can be modified by treating the compound (with the appropriately substituted side chain attached) with a base as described by Chaudhary et al., Journal of Organic Chemistry 58, 3798-3799 (1993) (hereby incorporated by reference herein in its entirety). Additionally or alternatively, various C(10) alpha isomers can be obtained using the oxidation-reduction-esterification sequence illustrated by Appendino et al., supra, and Datta et al., Tetrahedron Letters 36, 12, 1985-1988 (1995) (hereby incorporated by reference herein in its entirety) and in the following reaction scheme, wherein $X_{10}$, $X_3$, and $R_{10a}$ are as defined in connection with Formula (1) and PG is a hydroxy protecting group:

In a preferred one-pot protocol for the synthesis of the appropriate beta-lactam (I) coupling partner, a tetrahydrofuran solution of an optically pure beta-lactam was treated with a stoichiometric amount of 2-methoxy-propene in the present of a catalytic amount of p-toluenesulfonic acid to protect its hydroxy group ($P_2$), followed by treatment with the appropriate chloroformates (cyclobutyl or cyclopentyl) to introduce the $X_{10}$ substituent at ambient temperature. See, e.g., U.S. Published Patent Application No. 2005/0228037 to Holton et al. (hereby incorporated by reference herein in its entirety).

Processes for the preparation and resolution of the β-lactam (I) starting material are generally well known in the art. For example, the β-lactam may be prepared as described in Holton, U.S. Pat. No. 5,430,160 (col. 9, lines 2-50) or Holton, U.S. Pat. No. 6,649,632 (col. 7, line 45 to col. 8, line 60), and U.S. Pat. App. Pub. No. 2006/0281914 (page 1, paragraph [0021] to page 6, paragraph [0060]), each of which is hereby incorporated by reference in their entirety. The resulting enantiomeric mixtures of β-lactams may be resolved by a stereoselective hydrolysis using a lipase or enzyme as

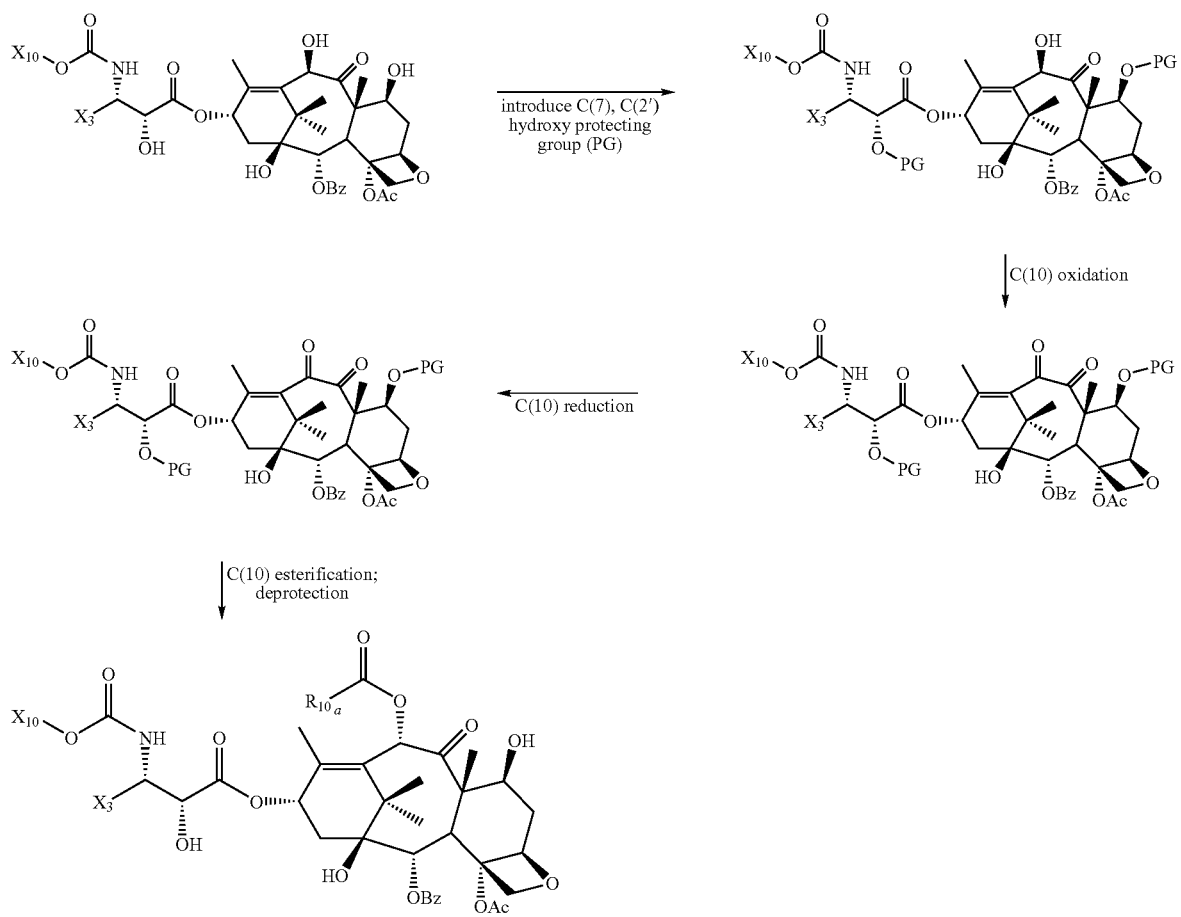

wherein $R_{10a}$, $X_3$ and $X_{10}$ are as defined in connection with Formula (1).

An exemplary oxidating agent for the C(10) hydroxy group in the above oxidation-reduction-esterification sequence is tetrapropylammonium perruthenate (TPAP), and an exemplary reducing agent for the C(10) keto group is sodium borohydride. A variety of protecting groups for the C(7) and C(2') hydroxy groups may be used, and several are described elsewhere herein (e.g., trialkylsilyl).

described, for example, in Patel, U.S. Pat. No. 5,879,929 (col. 16, line 1 to col. 18, line 27) or Patel, U.S. Pat. No. 5,567,614 or a liver homogenate as described, for example, in Holton, U.S. Pat. No. 6,548,293 (col. 3, lines 30-61), each of which is hereby incorporated by reference in its entirety, or by treatment with an optically active proline acylating agent followed by selective recovery of the unreacted enantiomer or one of the diastereomers as described in U.S. Pat. App. Pub. No. 2006/0281918 (page 1, paragraph [0022] to page 8, paragraph [0071]) (hereby incorporated by reference herein in its entirety). By way of example, U.S. Pat. No. 6,649,632 discloses the preparation of a β-lactam having a furyl substituent at the C(4) position of the β-lactam. With modifications evident to those skilled in the art, a β-lactam having a thienyl substituent at the β-lactam C(4) position may be prepared as illustrated in these prior patents and patent applications and as further disclosed in Example 11 below.

The compounds of the present disclosure may be provided in their salt form. Typically, the salt will be a pharmaceutically acceptable salt; that is, a salt prepared from pharmaceutically acceptable non-toxic acids, including inorganic acids and organic acids. Suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N"-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts of the compositions described herein can be prepared by reacting the compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, hereby incorporated by reference herein in its entirety.

Additionally or alternatively, the compounds may be provided in the form of a prodrug. In general, a pharmaceutically acceptable derivative or prodrug is any pharmaceutically acceptable salt, ester, salt of an ester or other derivative of a compound of this disclosure which, upon administration to a recipient, is capable of providing, either directly or indirectly, a compound of this disclosure or an inhibitorily active metabolite or residue thereof. Particularly favored derivatives or prodrugs are those that increase the bioavailability of the compounds of this disclosure when such compounds are administered to a patient (e.g., by allowing an orally administered compound to be more readily absorbed into the blood) or which enhance delivery of the parent compound to a biological compartment (e.g., the brain or lymphatic system) relative to the parent species. Pharmaceutically acceptable prodrugs include, but are not limited to, taxanes of the present disclosure derivatized with one or more of the following groups: phosphates, pivaloyloxymethyl, acetoxymethyl, phthalidyl, indanyl, methoxymethyl, methylpyridinium mesylate, bicarbonate, onium salts, phosphonooxymethyl carbonate, cinnamate, aminoacid, benzoyl, acyl, thioaryl, polyethylene glycol based, ester linked, polyalkylene oxide, dextran, polyvinyl alcohols, carbohydrate based polymers, oligopeptide, polyglutamic acid, polyamino acid, onium salts of 2-halogenated aza-arenes, highly polar amino sugar, and the like. Suitable positions in the taxane molecule of the present disclosure for prodrug formation include, but are not limited to, the C(2') and C(7) positions. Various forms of prodrugs are well known in the art. For examples of such prodrug derivatives, see: (a) *Design of Prodrugs*, edited by H. Bundgaard, (Elsevier, 1985) and *Methods in Enzymology*, Vol. 42, p. 309-396, edited by K. Widder, et al. (Acamedic Press, 1985); (b) *A Textbook of Drug Design and Development*, edited by Krosgaard-Larsen and H. Bundgaard, Chapter 5, "Design and Application of Prodrugs," by H. Bundgaard, p. 113-191 (1991); (c) H. Bundgaard, *Advanced Drug Delivery Reviews*, 8, 1-38 (1992); (d) H. Bundgaard, et al., *Journal of Pharmaceutical Sciences*, 77, 285 (1988); and (e) N. Kakeya, et al., *Chem. Pharm. Bull.*, 32, 692 (1984), each of which is hereby incorporated by reference herein in its entirety.

The taxanes of the instant disclosure are useful for inhibiting tumor growth in mammals including humans and is preferably administered in the form of a pharmaceutical composition comprising an effective anti-tumor amount of the compound of the instant disclosure in combination with at least one pharmaceutically or pharmacologically acceptable carrier. The carrier, also known in the art as an excipient, vehicle, auxiliary, adjuvant, or diluent, is any substance which is pharmaceutically inert, confers a suitable consistency or form to the composition, and does not diminish the therapeutic efficacy of the anti-tumor compounds. The carrier is "pharmaceutically or pharmacologically acceptable" if it does not produce an adverse, allergic or other untoward reaction when administered to a mammal or human, as appropriate.

The pharmaceutical compositions containing the anti-tumor compound of the present disclosure may be formulated in any conventional manner. Proper formulation is dependent upon the route of administration chosen. The compositions of the disclosure can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (e.g., nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present disclosure are well known to those of ordinary skill in the art and are selected based upon a number of factors: the particular anti-tumor compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, *Remington's Pharmaceutical Science* (A. Gennaro, ed.), Mack Publishing Co., Easton, Pa., (1985), pp. 1492-1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present disclosure are described in the following references: 7 *Modern Pharmaceutics*, Chapters 9 and 10 (Banker & Rhodes, Editors, 1979); Lieberman et al., *Pharmaceutical Dosage*

*Forms: Tablets* (1981); and Ansel, *Introduction to Pharmaceutical Dosage Forms,* 2nd Edition (1976).

The compositions of the disclosure for oral administration comprise an effective anti-tumor amount of the compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques, e.g., to delay disintegration and absorption.

The anti-tumor compound of the present disclosure may also be preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the disclosure for parenteral administration comprise an effective anti-tumor amount of the anti-tumor compound in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose, and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor EL® solution or Cremophor RH 40® solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.) (Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.,) (Marcel Dekker, Inc., New York, N.Y., 1980), *Remington's Pharmaceutical Sciences* (A. Gennaro, ed., 19th Ed.) (Mack Publishing, Easton, Pa., 1995), *The United States Pharmacopeia* 24, *The National Formulary* 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

Preferred solvents include those known to stabilize the anti-tumor compound, such as oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor EL® solution or Cremophor RH 40® solution). Commercially available triglyceride-rich oils include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®. Ethanol is a preferred solvent for use in dissolving the anti-tumor compound to form solutions, emulsions, and the like.

Additional minor components can be included in the compositions of the disclosure for a variety of purposes well known in the pharmaceutical industry. These components will for the most part impart properties which enhance retention of the anti-tumor compound at the site of administration, protect the stability of the composition, control the pH, facilitate processing of the anti-tumor compound into pharmaceutical formulations, and the like. Typically, each of these components is individually present in less than about 15 wt. % of the total composition, preferably less than about 5 wt. %, and more preferably less than about 0.5 wt. % of the total composition. Some components, such as fillers or diluents, can constitute up to 90 wt. % of the total composition, as is known in the formulation art. Such additives include cryoprotective agents for preventing reprecipitation of the taxane, surface active, wetting or emulsifying agents (e.g., lecithin, polysorbate-80, pluronic 60, polyoxyethylene stearate, and polyoxyethylated castor oils), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage form administration by these routes may be continuous or intermittent, depending, for example, upon the patient's physiological condition, whether the purpose of the administration is therapeutic or prophylactic, and other factors known to and assessable by a skilled practitioner.

Dosage and regimens for the administration of the pharmaceutical compositions of the disclosure can be readily determined by those with ordinary skill in treating cancer. It is understood that the dosage of the anti-tumor compounds will be dependent upon the age, sex, health, and weight of the recipient, kind of concurrent treatment, if any, frequency of treatment, and the nature of the effect desired. For any mode of administration, the actual amount of anti-tumor compound delivered, as well as the dosing schedule necessary to achieve the advantageous effects described herein, will also depend, in part, on such factors as the bioavailability of the anti-tumor compound, the disorder being treated, the desired therapeutic dose, and other factors that will be apparent to those of skill in the art. The dose administered to an animal, particularly a human, in the context of the present disclosure should be sufficient to affect the desired therapeutic response in the animal over a reasonable period of time. Preferably, an effective amount of the anti-tumor compound, whether administered orally or by another route, is any amount which would result in a desired therapeutic response when administered by that route. Preferably, the compositions for oral administration are prepared in such a way that a single dose in one or more oral preparations contains at least 20 mg of the anti-tumor compound per $m^2$ of patient body surface area, or at least 50, 100, 150, 200, 300, 400, or 500 mg of the anti-tumor compound per $m^2$ of patient body surface area, wherein the average body surface area for a human is 1.8 $m^2$. Preferably, a single dose of a composition for oral administration contains from about 20 to about 600 mg of the anti-tumor compound per $m^2$ of patient body surface area, more preferably from about 25 to about 400 $mg/m^2$, even more preferably, from about 40 to about 300 $mg/m^2$, even more preferably from about 50 to about 200 $mg/m^2$, and even more preferably about 50 to about 100 $mg/m^2$. Preferably, the compositions for parenteral administration are prepared in such a way that a single dose contains at least 20 mg of the anti-tumor compound per $m^2$ of patient body surface area, or at least 40, 50, 100, 150, 200, 300, 400, or 500 mg of the anti-tumor compound per $m^2$ of patient body surface area. Preferably, a single dose in one or more parenteral preparations contains from about 20 to about 500 mg of the anti-tumor compound per $m^2$ of patient body surface area, more preferably from about 40 to about 400 $mg/m^2$, even more preferably from about 60 to about 350 $mg/m^2$, and even more preferably about 50 to about 100 $mg/m^2$. However, the dosage may vary depending on the dosing schedule which can be adjusted as necessary to achieve the desired therapeutic effect. It should be noted that the ranges of effective doses provided herein are not intended to limit the disclosure and represent preferred dose ranges. The most preferred dosage will be tailored to the individual subject, as is understood and determinable by one of ordinary skill in the art without undue experimentation.

The concentration of the anti-tumor compound in a liquid pharmaceutical composition is preferably between about 0.001 mg and about 20 mg/mL of the composition, more preferably between about 0.01 mg and about 10 mg/mL of the composition, more preferably between about 0.1 mg and about 7 mg/mL, even more preferably between about 0.1 mg and about 5 mg/mL. In one embodiment, the concentration of the anti-tumor compound having chemical structure (1) in this formulation is 0.15 to 4 mg/mL. Relatively low concentrations are generally preferred because the anti-tumor compound is most soluble in the solution at low concentrations. The concentration of the anti-tumor compound in a solid pharmaceutical composition for oral administration is preferably between about 5 wt. % and about 50 wt. %, based on the total weight of the composition, more preferably between about 8 wt. % and about 40 wt. %, and most preferably between about 10 wt. % and about 30 wt. %.

In one embodiment, solutions for oral administration are prepared by dissolving an anti-tumor compound in any pharmaceutically acceptable solvent capable of dissolving the compound (e.g., ethanol or polyethylene glycol) to form a solution. An appropriate volume of a carrier which is a surfactant, such as Cremophor EL® solution, polysorbate 80, Solutol® HS15, or Vitamin E TPGS, is added to the solution while stirring to form a pharmaceutically acceptable solution for oral administration to a patient. For example, the resulting compositions may contain up to about 15% ethanol and/or up to about 15% surfactant, more typically, the concentrations will be about 7.5 to 15% by volume ethanol with an equal volume of surfactant and distilled water in the range of 75 to 90% by volume. For taste purposes, a fraction of the distilled water can be replaced by a diluted cherry or raspberry syrup, preferably, about 10 to 30% syrup with the remainder water. In one embodiment, the concentration of the anti-tumor compound having chemical structure (1) in this formulation is 2 to 4 mg/mL. If desired, such solutions can be formulated to contain a minimal amount of, or to be free of, ethanol, which is known in the art to cause adverse physiological effects when administered at certain concentrations in oral formulations. In a preferred embodiment, the solution comprises about 10% ethanol, about 10% surfactant selected from polysorbate 80 (e.g., Tween® 80), polyethoxylated castor oils (e.g., Cremophor®), and mixtures thereof, and about 80% distilled water.

In another embodiment, powders or tablets for oral administration are prepared by dissolving an anti-tumor compound in any pharmaceutically acceptable solvent capable of dissolving the compound (e.g., ethanol or polyethylene glycol) to form a solution. The solvent can optionally be capable of evaporating when the solution is dried under vacuum. An additional carrier can be added to the solution prior to drying, such as Cremophor EL® solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving an anti-tumor compound in any pharmaceutically acceptable solvent capable of dissolving the compound (e.g., ethanol or polyethylene glycol) to form a solution. An appropriate volume of a carrier which is an emulsion, such as Liposyn® II, Liposyn® III, or Intralipid® emulsion, is added to the solution while stirring to form a pharmaceutically acceptable emulsion for parenteral administration to a patient. For example, the resulting composition may contain up to about 10% ethanol and/or more than about 90% carrier, more typically, the concentration will be about 5 to 10% by volume ethanol and about 90 to 95% by volume carrier. In one embodiment, the concentration of the anti-tumor compound having chemical structure (1) in the dosing solution is about 1 to 2 mg/mL. If desired, such emulsions can be formulated to contain a minimal amount of, or to be free of, ethanol or Cremophor® solution, which are known in the art to cause adverse physiological effects when administered at certain concentrations in parenteral formulations. In a preferred embodiment, the emulsion comprises about 5% ethanol and about 95% carrier (e.g., Intralipid® 20%, Liposyn® II 20%, or a mixture thereof). In this preferred embodiment, the emulsion is free of agents which are known to cause adverse physiological effects, such as polyethoxylated castor oils (e.g., Cremophor®) and polysorbate 80 (e.g., Tween® 80).

Solutions for parenteral administration can be prepared by dissolving an anti-tumor compound in any pharmaceutically acceptable solvent capable of dissolving the compound (e.g., ethanol or polyethylene glycol) to form a solution. An appropriate volume of a carrier which is a surfactant, such as Cremophor® solution, polysorbate 80, or Solutol® HS15, is added to the solution while stirring to form a pharmaceutically acceptable solution for parenteral administration to a patient. For example, the resulting composition may contain up to about 10% ethanol and/or up to about 10% surfactant, more typically, the concentration will be about 5 to 10% by volume ethanol with an equal volume of surfactant and saline in the range of 80 to 90% by volume. If desired, such solutions can be formulated to contain a minimal amount of, or to be free of, ethanol or Cremophor® solution, which are known in the art to cause adverse physiological effects when administered at certain concentrations in parenteral formulations. In a preferred embodiment, the solution comprises about 5% ethanol, about 5% polysorbate 80 (e.g., Tween® 80) or polyethoxylated castor oils (e.g., Cremophor®), and about 90% saline (0.9% sodium chloride). To minimize or eliminate potential adverse effects (e.g., hypersensitivity reactions), a patient receiving this embodiment is preferably pretreated with dexamethasone, diphenhydramine, or any other agent known in the art to minimize or eliminate these adverse reactions.

Other suitable parenteral formulations include liposomes. Liposomes are generally spherical or spheroidal clusters or aggregates of amphiphatic compounds, including lipid compounds, typically in the form of one or more concentric layers, for example monolayers or bilayers. The liposomes may be formulated from either ionic or nonionic lipids. Liposomes from nonionic lipids are also referred to as niosomes. References for liposomes include: (a) *Liposomes Second Edition: A Practical Approach*, edited by V. Torchillin and V. Weissig, Oxford University Press, 2003; (b) M. Malmstein, *Surfactants and Polymers in Drug Delivery*, Marcel Dekker Inc., 2002; and (c) Muller et al., *Emulsions and Nanosuspensions for the Formulation of Poorly Soluble Drugs*, Medpharm Scientific Publishers, 1998.

If desired, the emulsions or solutions described above for oral or parenteral administration can be packaged in IV bags, vials or other conventional containers in concentrated form and diluted with any pharmaceutically acceptable liquid, such as saline, to form an acceptable taxane concentration prior to use as is known in the art.

Abbreviations And Definitions

The following definitions and methods are provided to better define the present disclosure and to guide those of ordinary skill in the art in the practice of the present disclosure. Unless otherwise noted, terms are to be understood according to conventional usage by those of ordinary skill in the relevant art.

With regard to stereoisomers, it should be understood that a solid line designation for the bonds in the compositions corresponding to Formula (1) (and others herein) for attachment of an substituent group to a chiral carbon atom of the compound indicates that these groups may lie either below or above the plane of the page (i.e., —◼R or ⋯‖‖‖R). All isomeric forms of the compounds disclosed herein are contemplated, including racemates, racemic mixtures, and individual enantiomers or diastereomers.

The terms "acetal" and "ketal," as used herein alone or as part of another group, denote the moieties represented by the following formulae, respectively:

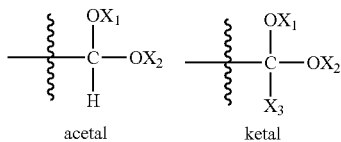

wherein $X^1$ and $X_2$ are independently hydrocarbyl, substituted hydrocarbyl, heterocyclo, or heteroaryl, and $X_3$ is hydrocarbyl or substituted hydrocarbyl, as defined in connection with such terms, and the wavy lines represent the attachment point of the acetal or ketal moiety to another moiety or compound.

The term "acyl," as used herein alone or as part of another group, denotes the moiety formed by removal of the hydroxyl group from the group —COOH of an organic carboxylic acid, e.g., $X_4C(O)$—, wherein $X_4$ is $X^1$, $X^1O$—, $X^1$ $X^2N$—, or $X^1S$—, $X^1$ is hydrocarbyl, heterosubstituted hydrocarbyl, or heterocyclo, and $X^2$ is hydrogen, hydrocarbyl or substituted hydrocarbyl. Exemplary acyl moieties include acetyl, propionyl, benzoyl, pyridinylcarbonyl, and the like.

The term "acyloxy," as used herein alone or as part of another group, denotes an acyl group as described above bonded through an oxygen linkage (—O—), e.g., $X_4C(O)O$— wherein $X_4$ is as defined in connection with the term "acyl."

The term "alkoxy," as used herein alone or as part of another group, denotes an —$OX_5$ radical, wherein $X_5$ is as defined in connection with the term "alkyl." Exemplary alkoxy moieties include methoxy, ethoxy, propoxy, or 2-propoxy, n-, iso-, or tert-butoxy, and the like.

The term "alkenoxy," as used herein alone or as part of another group, denotes an —$OX_6$ radical, wherein $X_6$ is as defined in connection with the term "alkenyl." Exemplary alkenoxy moieties include ethenoxy, propenoxy, butenoxy, hexenoxy, and the like.

The term "alkynoxy," as used herein alone or as part of another group, denotes an —$OX_7$ radical, wherein $X_7$ is as defined in connection with the term "alkynyl." Exemplary alkynoxy moieties include ethynoxy, propynoxy, butynoxy, hexynoxy, and the like.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "cycloalkyl," as used herein alone or as part of another group, denotes a cyclic saturated monovalent bridged or non-bridged hydrocarbon radical of three to ten carbon atoms. Exemplary cycloalkyl moieties include cyclopropyl, cyclobutyl, cyclopentyl, cyclohexyl, or adamantyl. Additionally, one or two ring carbon atoms may optionally be replaced with a —CO— group.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "amine" or "amino," as used herein alone or as part of another group, represents a group of formula —$N(X_8)(X_9)$, wherein $X_8$ and $X_9$ are independently hydrogen, hydrocarbyl, substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring. "Substituted amine," for example, refers to a group of formula —$N(X_8)(X_9)$, wherein at least one of $X_8$ and $X_9$ are other than hydrogen.

"Unubstituted amine," for example, refers to a group of formula —$N(X_8)(X_9)$, wherein $X_8$ and $X_9$ are both hydrogen.

The terms "amido" or "amide," as used herein alone or as part of another group, represents a group of formula —$CON(X_8)(X_9)$, wherein $X_8$ and $X_9$ are as defined in connection with the terms "amine" or "amino." "Substituted amide," for example, refers to a group of formula —$CON(X_8)(X_9)$, wherein at least one of $X_8$ and $X_9$ are other than hydrogen. "Unsubstituted amido," for example, refers to a group of formula —$CON(X_8)(X_9)$, wherein $X_8$ and $X_9$ are both hydrogen The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "alkaryl" or "alkylaryl," as used herein alone or as part of another group, denotes an -(arylene)-$X_{11}$ radical, wherein $X_{11}$ is as defined in connection with the term "alkyl."

The term "cyano," as used herein alone or as part of another group, denotes a group of formula —CN.

Unless otherwise indicated, the term "ester," as used herein alone or as part of another group, denotes a group of formula —$COOX_{12}$ wherein $X_{12}$ is alkyl or aryl, each as defined in connection with such term.

The term "ether," as used herein alone or as part of another group, includes compounds or moieties which contain an oxygen atom bonded to two carbon atoms. For example, ether includes "alkoxyalkyl" which refers to an alkyl, alkenyl, or alkynyl group substituted with an alkoxy group.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The terms "halide," "halogen" or "halo" as used herein alone or as part of another group refer to chlorine, bromine, fluorine, and iodine.

The term "heteroatom" shall mean atoms other than carbon and hydrogen.

The term "heteroaromatic" or "heteroaryl" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydroxy protecting group" as used herein denote a group capable of protecting a free hydroxyl group ("protected hydroxy") which, subsequent to the reaction for which protection is employed, may be removed without disturbing the remainder of the molecule. A variety of protecting groups for the hydroxyl group and the synthesis thereof may be found in *Protective Groups in Organic Synthesis*, 3rd Edition by T. W. Greene and P. G. M. Wuts, John Wiley and Sons, 1999. Exemplary hydroxy protecting groups include methoxymethyl, 1-ethoxyethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, dimethylphenylsilyl, trichloromethoxycarbonyl and 2,2,2-trichloroethoxymethyl.

The term "hydroxy," as used herein alone or as part of another group, denotes a group of formula —OH.

The term "keto," as used herein alone or as part of another group, denotes a double bonded oxygen moiety (i.e., =O).

The term "nitro," as used herein alone or as part of another group, denotes a group of formula —NO$_2$.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioethers.

The term "thioether," as used herein alone or as part of another group, denotes compounds and moieties that contain a sulfur atom bonded to two different carbon or hetero atoms (i.e., —S—), and also includes compounds and moieties containing two sulfur atoms bonded to each other, each of which is also bonded to a carbon or hetero atom (i.e., dithioethers (—S—S—)). Examples of thioethers include, but are not limited to, alkylthioalkyls, alkylthioalkenyls, and alkylthioalkynyls. The term "alkylthioalkyls" includes compounds with an alkyl, alkenyl, or alkynyl group bonded to a sulfur atom that is bonded to an alkyl group. Similarly, the term "alkylthioalkenyls" and "alkylthioalkynyls" refer to compounds or moieties where an alkyl, alkenyl, or alkynyl group is bonded to a sulfur atom that is covalently bonded to an alkynyl group.

The term "thiol," as used herein alone or as part of another group, denotes a group of formula —SH.

As used herein, "Ac" means acetyl; "Bz" means benzoyl; "TES" means triethylsilyl; "TMS" means trimethylsilyl; "LAH" means lithium aluminum hydride; "10-DAB" means 10-desacetylbaccatin III; "THF" means tetrahydrofuran; "DMAP" means 4-dimethylamino pyridine; "LHMDS" or "LiHMDS" means lithium hexamethyldisilazide; "TESCl" means triethylsilyl chloride; "TMSCl" means trimethylsilyl chloride; "DMF" means N,N-dimethylformamide; "MOP" means 2-methoxypropene; "LDA" means lithium diisopropylamide; "—OSiEt$_3$" means —O-triethylsilyl; "—O—SiMe$_3$" means —O-trimethylsilyl; "nBuLi" or "BuLi" means n-butyllithium; "DME" means dimethoxyethane; "ACN" means acetonitrile; "cPr" means cyclopropyl; "cPent" means cyclopentyl; "cPentO" means cyclopentyloxycarbonyl; "cBoc" means cyclobutoxycarbonyl.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLE 1

10-Cyclopropylcarbonyl-7-Triethylsilyl-10-DAB

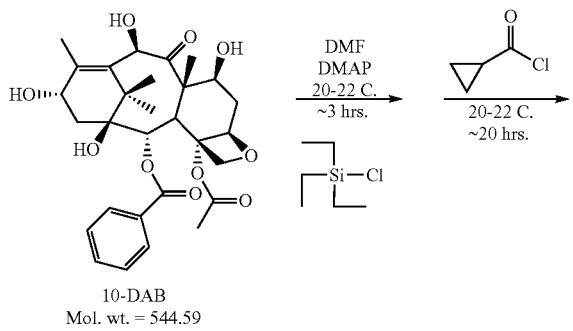

10-DAB
Mol. wt. = 544.59

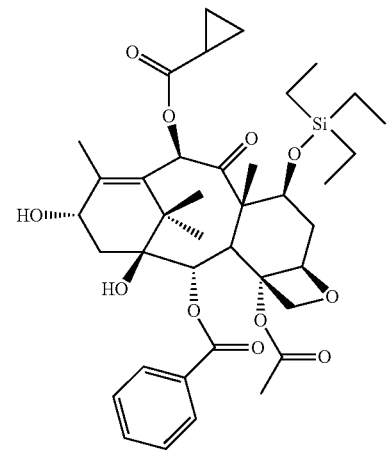

10-Cyclopropylcarboxyl-7-TES-10-DAB
Mol. wt. = 726.92

10-DAB (10.00 g, 18.36 mmol) was dissolved in anhydrous DMF at 6.0 mL/g (60.0 mL) along with 3 eq. of DMAP (6.73 g, 55.09 mmol) under nitrogen and magnetic stirring. To this clear yellowish solution at ambient temperature (22 to 25° C.) was added, drop-wise, 1.05 eq. of chlorotriethylsilane (2.91 g, 19.28 mmol) over a period of about 15 minutes. After 1 hr, $^1$HNMR reaction monitoring indicated that about 3% of the starting material 10-DAB was left un-reacted. A corrective amount of 3.8% chlorotriethylsilane was added and stirred for 2 hr for the reaction to achieve near completion with about 1% starting material remained un-reacted. To the reaction was added 1.05 eq. of cyclopropanecarbonyl chloride (2.02 g, 19.28 mmol) at ambient temperature and over a period of ~30 minutes. After stirring for 18 hrs, $^1$HNMR monitoring indicated that approximately 1.5% of the 7-TES-10-DAB was left un-reacted. A corrective amount of 2.6% cyclopropanecarbonyl chloride was added and further stirred for 2 hrs when the reaction went to near completion by TLC (2:3 E:H). The reaction mixture then was poured into ~800 mL of ice cold water with stirring at 0° C. After 1.0 hr, the solid product was collected by vacuum filtration. The filter cake was washed with cold water and dissolved in ~400 mL of ethyl acetate. The ethyl acetate solution was transferred to a separatory funnel, washed with water, saturated NaHCO$_3$ solution and brine, dried over Na$_2$SO$_4$, filtered and concentrated to give 15.4759 g of the crude product. This crude was filtered through a short pad of silica gel using 3:2 E:H. The filtrate was concentrated to give 13.5239 g of the product at 91.9% HPLC purity. This product was dissolved in ethyl acetate (8.0 mL/g) at reflux and then hexanes (16 mL/g) was added. The slurry of the crystallized product was cooled to room temperature and then to 0° C. The white crystalline product was collected via a Buchner funnel and washed with ice cold ethyl acetate:hexanes (1:4 E:H). The filter cake was dried under vacuum and then oven dried under vacuum (78° C. and <0.1 mmHg) to give 10.34 g the product (14.22 mmol, 77.46%) at 97.4% HPLC purity.

m.p.=222° C. $^1$HNMR (400 MHz, CDCl$_3$, δ (ppm): 0.56 (m, 6H), 0.92 (t, J=8.05 Hz, 9H), 0.99-1.05 (m, 2H), 1.05 (s, 3H), 1.13-1.21 (m, 2H), 1.21 (s, 3H), 1.6 (s, 1H), 1.68 (s, 3H), 1.76 (m, 1H), 1.87 (t, J=12.44 Hz, 1H), 2.01 (d, J=4.95 Hz, 1H), 2.2 (s, 3H), 2.26-2.28 (m, 2H), 2.29 (s, 3H), 2.52 (m, 1H), 3.89 (d, J=7.06 Hz, 1H), 4.16 (d, J=8.36 Hz, 1H), 4.3 (d, J=8.30 Hz, 1H), 4.47 (dd, J=10.20, 6.84 Hz), 4.84 (bm, 1H), 4.97 (dd, J=9.41, 1.56 Hz, 1H), 5.63 (d, J=7.16 Hz, 1H), 6.46 (s, 1H), 7.48 (dd, J=7.90, 7.73 Hz, 2H), 7.61 (dd, J=8.1, 7.35 Hz, 1H), 8.10 (d, J=7.16 Hz, 2H).

EXAMPLE 2

10-Propionyl-7-Triethylsilyl-10-Deacetyl-Baccatin

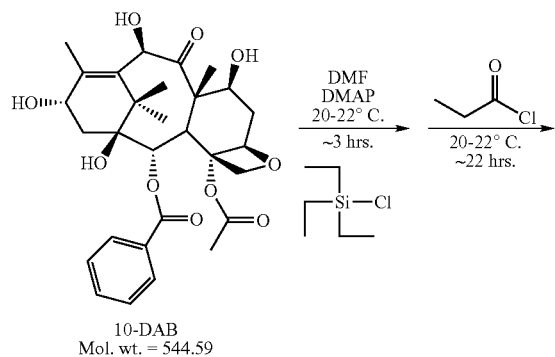

10-DAB
Mol. wt. = 544.59

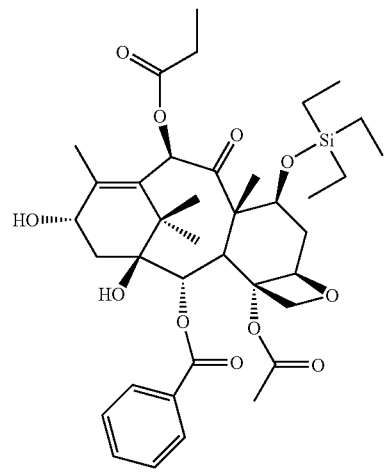

10-Propionyl-7-TES-10-DAB
Mol. wt. = 714.91

Using the procedure of Example 1, 10.00 g of 10-DAB was reacted with triethylchlorosilane and propionyl chloride in the present of DMAP to produce 7.94 g of the 10-propionyl-7-TES-10-DAB (60.5% yield) at 95.8% HPLC purity.

$^1$HNMR (400 MHz, CDCl$_3$) δ (ppm): 0.5-0.67 (m, 6H), 0.92 (t, J=7.93 Hz, 9H), 1.04 (s, 3H), 1.20 (s, 3H), 1.21 (t, J=7.6 Hz, 3H), 1.6 (s, 1H), 1.68 (s, 3H), 1.81-1.94 (m, 1H), 2.0 (d, J=4.94 Hz, 1H), 2.2 (s, 3H), 2.24-2.32 (m, 2H), 2.28 (s, 3H), 2.35-2.59 (m, 3H), 3.9 (d, J=6.83 Hz, 1H), 4.16 (d, J=8.36 Hz, 1H), 4.29 (d, J=8.18 Hz, 1H), 4.45-4.54 (m, 1H), 4.79-4.89 (m, 1H), 4.97 (d, J=7.84 Hz, 1H), 5.63 (d, J=7.16 Hz, 1H), 6.48 (s, 1H), 7.43-7.53 (m, 2H), 7.56-7.64 (m, 1H), 8.10 (d, J=7.05 Hz, 2H).

EXAMPLE 3

2'-MOP-7-TES-17932

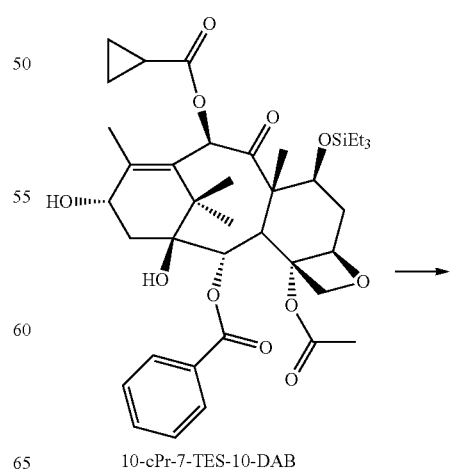

10-cPr-7-TES-10-DAB

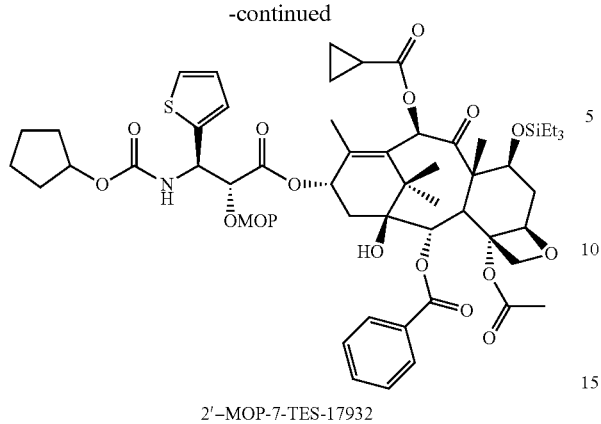

2'-MOP-7-TES-17932

A solution of 10-cPr-7-TES-10-DAB (209 mg, 0.287 mmol) and N-cPentO-(O-MOP)—SIT302 (111 mg, 0.316 mmol) in 8 mL of anhydrous tetrahydrofuran at −45° C., under nitrogen and magnetic stirring, was charged with 0.316 mL (0.316 mmol) of lithium hexamethyl disilazide and stirred for 4 hours. The reaction was quenched with 1 mL of aqueous sodium bicarbonate and diluted with 10 mL ethyl acetate. The mixture was washed with 10 mL each of H$_2$O, sodium bicarbonate, and brine and dried over sodium sulfate. The solvent was removed in vacuo and the crude solid was purified by flash chromatography to give 250 mg of the 2'-MOP-7-TES-17932 (80.6%).

$^1$H-NMR (400 MHz, J in Hz, CDCl$_3$): δ (ppm) 0.56 (m, 6H), 0.91 (m, 9H), 1.12 (m, 2H), 1.15-1.28 (m, 11H), 1.34 (s, 3H), 1.42-1.78 (m, 13H), 1.89 (t, J=12.33, 1H), 2.02 (s, 3H), 2.15 (m, 1H), 2.30 (m, 1H), 2.48-2.56 (m, 4H), 2.85 (s, 3H), 3.84 (d, J=7.04, 1H), 4.18 (d, J=8.53, 1H), 4.32 (d, J=8.53, 1H), 4.46 (dd, J=6.69, 10.58, 1H), 4.55 (s, 1H), 4.96 (m, 2H), 5.47 (m, 1H), 5.54 (d, J=7.02, 1H), 6.21 (t, J=9.06, 1H), 6.46 (s, 1H), 6.97 (m, 2H), 7.22 (dd, J=2.32, 3.90, 1H), 7.51 (m, 2H), 7.61 (m, 1H), 8.12 (d, J=7.09, 2H).

EXAMPLE 4

2'MOP-7-TES-18926

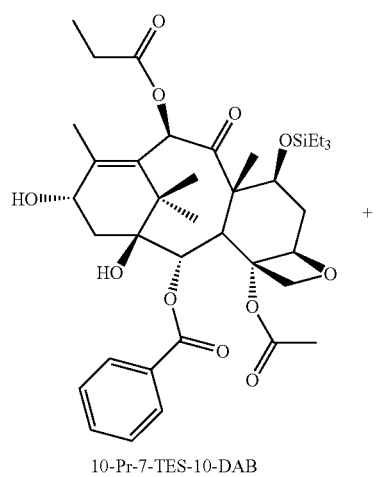

10-Pr-7-TES-10-DAB

+

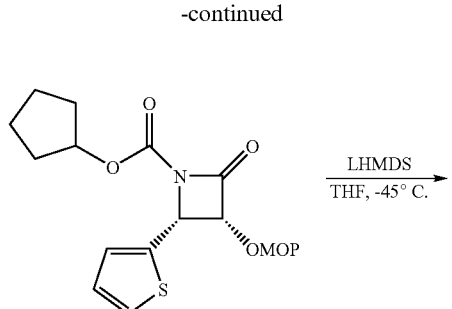

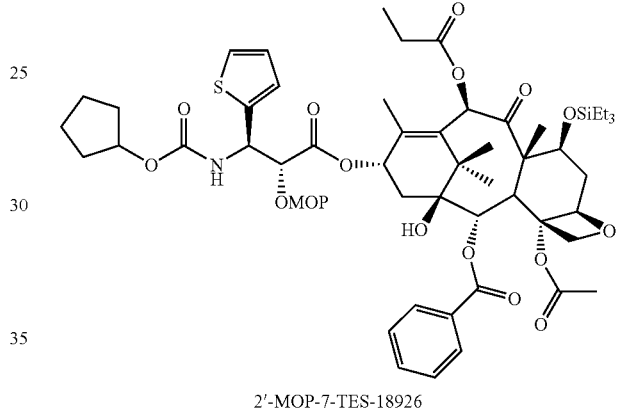

2'-MOP-7-TES-18926

A solution of 10-Pr-7-TES-10-DAB (7.72 g, 10.81 mmol) and N-cPentO-(O-MOP)—SIT302 (4.59, g 12.98 mmol) in 70 mL of anhydrous tetrahydrofuran at −45° C. was charged with 12.97 mL (12.97 mmol) of lithium hexamethyldisilazide and stirred for 1.5 hours. The reaction was quenched with 15 mL of aqueous sodium bicarbonate and washed with 50 mL of H$_2$O, 50 mL of sodium bicarbonate and 50 mL of brine. The organic layer was diluted with 70 mL of heptane and passed through a plug of basified silica gel. Residual product was flushed from the plug column with 200 mL of a 1:1 mixture of ethyl acetate/heptane. The solvent was removed in vacuo giving 15.08 g of a crude foam. Crystallization from ethyl acetate/heptane (1:1) gave 9.6 g of 2'-MOP-7-TES-18926 as a white solid (83%).

$^1$H-NMR (400 MHz, J in Hz, CDCl$_3$), δ (ppm): 0.57 (m, 6H), 0.90 (m, 9H), 1.19-1.70 (m, 27H), 1.89 (t, J=12.66, 1H), 2.03 (s, 3H), 2.16 (m, 1H), 2.29 (m, 1H), 2.38-2.56 (m, 6H), 2.85 (s, 3H), 3.84 (d, J=6.99, 1H), 4.18 (d, J=8.46, 1H), 4.32 (d, J=8.46, 1H), 4.47 (dd, J=6.65, 10.60, 1H), 4.56 (s, 1H), 4.96 (m, 2H), 5.48 (m, 1H), 5.55 (d, J=8.60, 1H), 5.70 (d, J=7.01, 1H), 6.20 (t, J=9.09, 1H), 6.47 (s, 1H), 6.97 (m, 2H), 7.22 (d, J=4.21, 1H), 7.51 (m, 2H), 7.61 (m, 1H), 8.22 (d, J=7.63, 2H).

EXAMPLE 5

2'-MOP-7-TES-18365

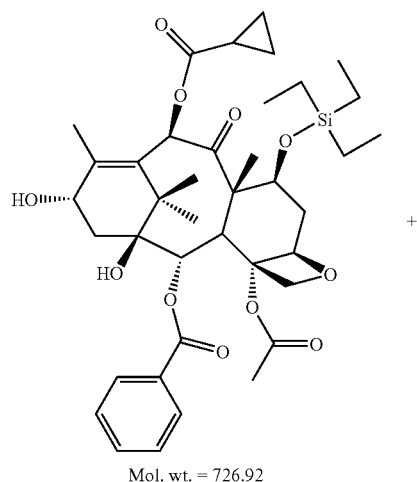

Mol. wt. = 726.92

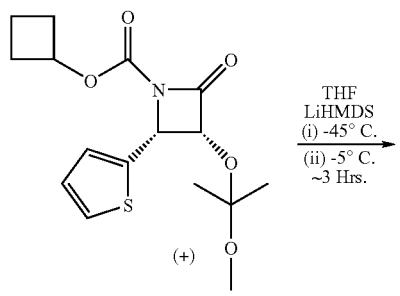

Mol. wt. = 339.41

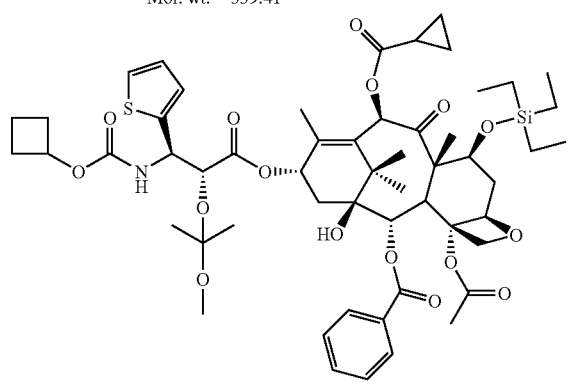

2'-MOP-7-TES-18365
Mol. wt. = 1066.33

10-Cyclopropanecarboxyl-7-TES-10-DAB (8.00 g, 11.00 mmol) was dissolved in anhydrous THF at 0.13 M (84.7 mL) under nitrogen and magnetic stirring. To the clear solution at −45° C. was added 1.14 eq. of a 1.0 M solution of lithium bis(trimethylsilyl)amide (2.10 g, 12.55 mmol) in THF over a period of ~10-15 minutes. The solution was stirred for 45 minutes at −45° C. To this solution at −45° C. was added a solution of 1.14 eq. N-cBoc-(O-MOP)—SIT302 (4.26 g, 12.55 mmol) over a period of ~5 to 10 minutes then stirred at −5 to −10° C. The coupling was complete in ~3 hr according to TLC (2:3 E:H) analysis. The reaction was quenched with 15 mL of saturated aqueous sodium bicarbonate solution, extracted with 150 mL of ethyl acetate, washed with 50 mL of brine, dried over sodium sulfate and filtered. The filtrate was concentrated to give 14.76 g of the crude product. This crude was plug filtered using 1:2.5 E:H and 1% triethylamine. The filtrate was concentrated in vacuo to give 11.65 g of the product. The product was further recrystallized using IPA (5 ml/g+1% triethylamine) to give 10.51 g (9.86 mmol, 89.60%) after drying to a constant weight under vacuum (<0.1 mmHg).

$^1$HNMR (400 MHz, CDCl$_3$, δ (ppm): 0.47-0.64 (m, 6H), 0.83-0.97 (m, 2H), 0.91 (t, J=7.9 Hz), 1.14-1.26 (m, 2H), 1.2 (s, 3H), 1.22 (s, 3H), 1.24 (s, 3H), 1.35 (s, 3H), 1.37-1.49 (m, 1H), 1.67 (s, 1H), 1.69 (s, 3H), 1.71-1.79 (m, 1H), 1.84-1.94 (m, 1H), 1.94-2.05 (m, 2H), 2.02 (s, 3H), 2.08-2.41 (m, 5H), 2.47 (s, 3H), 2.84 (s, 3H), 3.84 (d, J=7.16 Hz, 1H), 4.19 (d, J=8.53 Hz, 1H), 4.31 (d, J=8.53 Hz, 1H), 4.42-4.50 (m, 1H), 4.56 (d, J=2.78 Hz, 1H), 4.75-4.85 (m, 1H), 4.96 (d, J=9.18 Hz, 1H), 5.46 (bd, J=7.25 Hz, 1H), 5.59 (bd, J=8.12 Hz, 1H), 5.69 (d, J=7.05 Hz, 1H), 6.16-6.25 (m, 1H), 6.46 (s, 1H), 6.95-7.0 (m, 2H), 7.22 (dd, J=4.38, 2.04 Hz, H), 7.48-7.54 (m, 2H), 7.59-7.64 (m, 1H), 8.1-8.15 (m, 2H).

EXAMPLE 6

2'-MOP-7-TES-19244

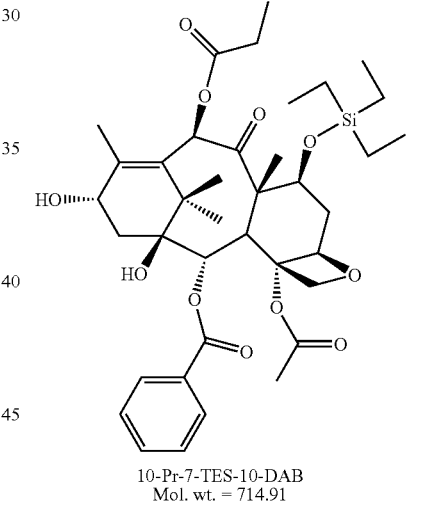

10-Pr-7-TES-10-DAB
Mol. wt. = 714.91

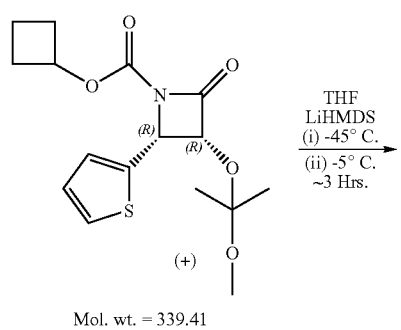

Mol. wt. = 339.41

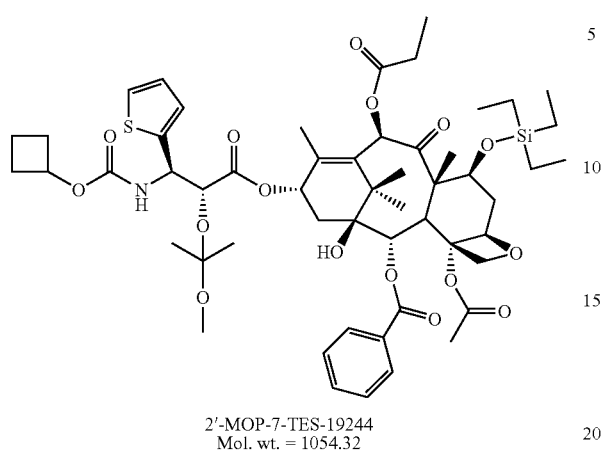

2'-MOP-7-TES-19244
Mol. wt. = 1054.32

Using the LHMDS coupling procedure described above, the 2'-MOP-7-TES-19244 was produced from 10-proprionyl-7-TES-10-DAB and N-cBoc-(O-MOP)—SIT302.

$^1$HNMR (400 MHz, CDCl3), δ (ppm): 0.49-0.66 (m, 6H), 0.92 (t, J=7.9 Hz, 9H), 1.15-1.28 (m, 11H), 1.35 (s, 3H), 1.37-1.49 (m, 1H), 1.58-1.76 (m, 5H), 1.83-1.95 (m, 1H), 1.95-2.08 (5H), 2.08-2.26 (m, 3H), 2.26-2.46 (m, 2H), 2.47 (s, 3H), 2.86 (s, 3H), 3.85 (d, J=6.82 Hz, 1H), 4.19 (d, J=8.53 Hz, 1H), 4.31 (d, J=8.53 Hz, 1H), 4.44-4.52 (m, 1H), 4.56 (d, J=2.9 Hz, 1H), 4.75-4.86 (m, 1H), 4.94 (d, J=9.36 Hz, 1H), 5.46 (bd, J=8.0 Hz, 1H), 5.57 (bd, J=8.58 Hz, 1H), 5.69 (d, J=7.16 Hz, 1H), 6.15-6.25 (m, 1H), 6.47 (s, 1H), 6.96-6.98 (m, 2H), 7.22 (dd, J=3.7, 3.0 Hz, 1H), 7.48-7.54 (m, 2H), 7.58-7.64 (m, 1H), 8.10-8.14 (m, 2H).

EXAMPLE 7

Compound 18926

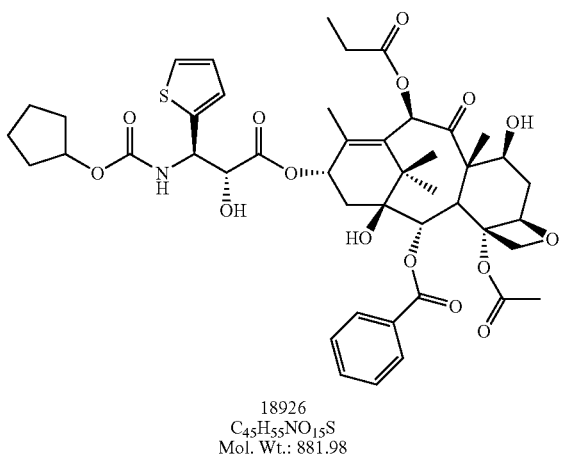

18926
$C_{45}H_{55}NO_{15}S$
Mol. Wt.: 881.98

To a solution of 2'-MOP-7-TES-18926(9.6 g, 8.98 mmol) in 70 mL of acetonitrile was added 25 mL of 0.2 N HCl at room temperature. After stirring for 24 hours, the reaction was diluted with 70 mL of ethyl acetate and washed with 50 mL each of $H_2O$, sodium bicarbonate, and brine. The organic layer was passed through a pad of silica gel and flushed with 150 mL of ethyl acetate. The solvent was removed in vacuo and the crude product was crystallized from ethyl acetate: heptane (1:1) giving 6.09 g of compound 18926 (76.9%).

m.p: 213° C.; $^1$H-NMR (400 MHz, J in Hz, CDCl$_3$), δ (ppm): 1.16 (s, 3H), 1.24 (t, J=7.50, 3H), 1.27 (s, 3H), 1.43-1.77 (m, 12H), 1.86-1.92 (m, 4H), 2.26-2.39 (m, 5H), 2.45-2.61 (m, 4H), 3.37 (d, J=5.29, 1H), 3.82 (d, J=7.16, 1H), 4.18 (d, J=8.7, 1H), 4.30 (d, J=8.36, 1H), 4.42 (m, 1H), 4.66 (dd, J=2.22, 5.29, 1H), 4.95 (m, 2H), 5.35 (d, J=9.98, 1H), 5.54 (d, J=8.87, 1H), 5.67 (d, J=7.17, 1H), 6.27 (t, J=9.04, 1H), 6.31 (s, 1H), 7.01 (dd, J=3.59, 5.09, 1H), 7.10 (d, J=3.41, 1H), 7.28 (dd, J=1.19, 5.11, 1H), 7.51 (m, 2H), 7.61 (m, 1H), 8.13 (d, J=7.34, 2H). Anal. Calcd for $C_{45}H_{55}NO_{15}S$: C, 61.28; H, 6.29. Found: C, 61.13; H, 6.40. $[α]_{20}^D$=−56.4° (C=1, MeOH).

EXAMPLE 8

Compound 17932

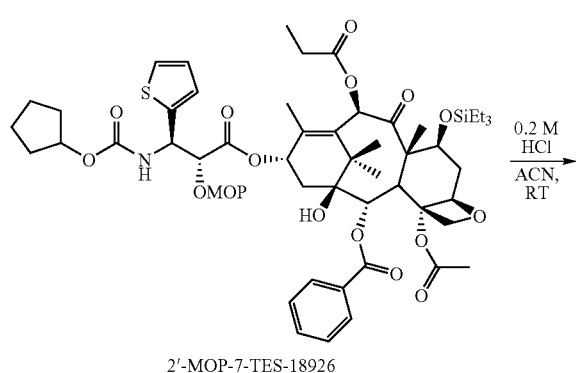

2'-MOP-7-TES-18926

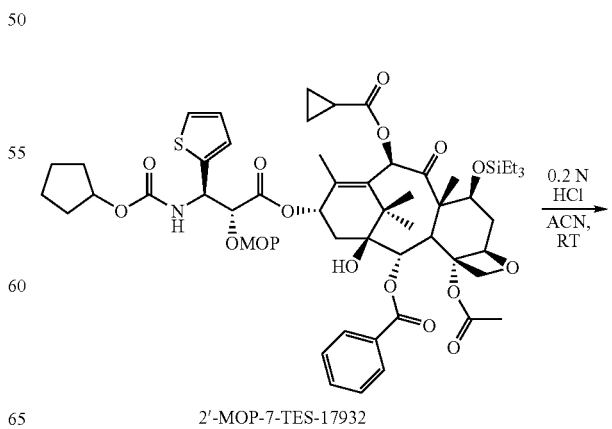

2'-MOP-7-TES-17932

-continued

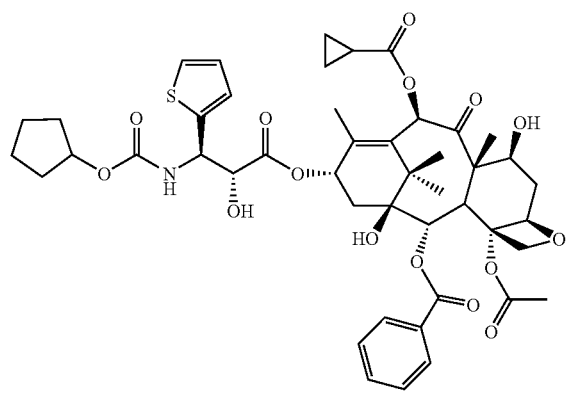

17932
C46H55NO15S
Mol. Wt.: 893.99

Using the deprotection procedure described above, 250 mg of 2'-MOP-7-TES-17932 was treated with 0.2 M HCl in acetonitrile to give compound 17932 (155 mg) after purification.

m.p: 165-167° C.; $^1$H-NMR (400 MHz, CDCl$_3$), δ (ppm) 0.98-1.03 (m, 2H), 1.12-1.17 (m, 5H), 1.28 (s, 3H), 1.44-1.91 (m, 17H), 2.26-2.39 (m, 5H), 2.50-2.58 (m, 2H), 3.38 (d, J=5.28, 1H), 3.81 (d, J=6.99, 1H), 4.18 (d, J=8.53, 1H), 4.30 (d, J=8.36, 1H), 4.40 (m, 1H), 4.65 (dd, J=2.22, 5.29, 1H), 4.94 (m, 2H), 5.36 (d, J=9.28, 1H), 5.54 (d, J=8.18, 1H), 5.67 (d, J=6.99, 1H), 6.27 (t, J=8.87, 1H), 6.30 (s, 1H), 7.02 (dd, J=3.59, 5.11, 1H), 7.10 (d, J=3.41, 1H), 7.29 (dd, J=1.19, 5.11, 1H), 7.51 (m, 2H), 7.59 (m, 1H), 8.12 (d, J=7.34, 2H).

Anal. Calcd for C$_{46}$H$_{55}$NO$_{15}$S: C, 61.80; H, 6.22. Found: C, 61.61; H, 6.29. [α]$_{20}^{D}$=−47.6° (C=1, MeOH).

EXAMPLE 9

Compound 18365

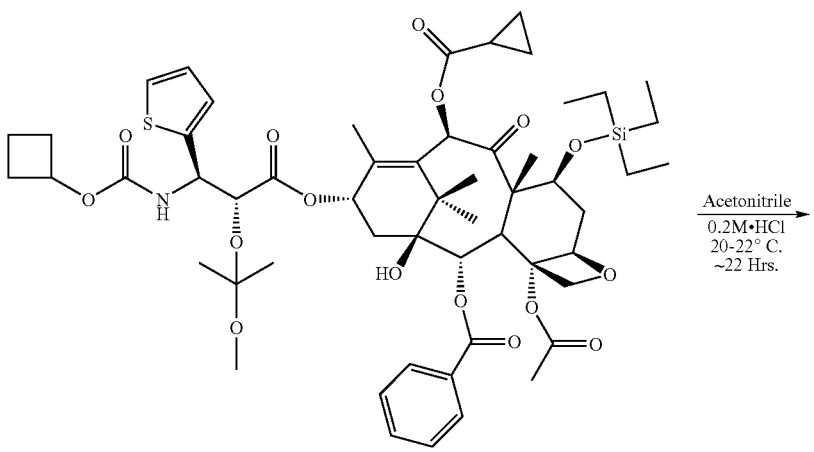

2'-MOP-7-TES-18365
Mol. wt. = 1066.33

Acetonitrile
0.2M•HCl
20-22° C.
~22 Hrs.

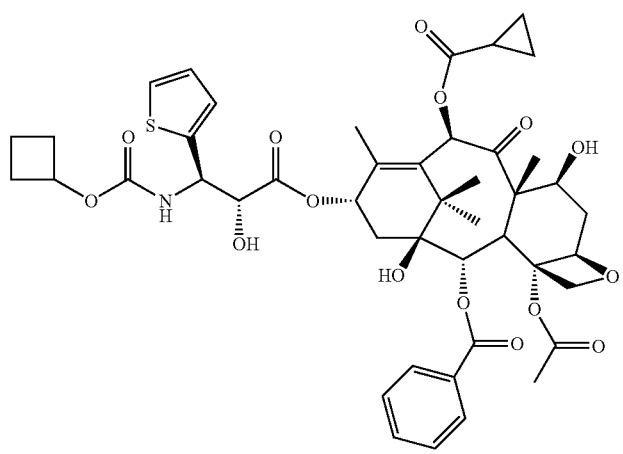

18365
Mol. wt. = 879.97

Using the deprotection procedure described above, 10.51 g (9.86 mmol) of the 2'-MOP-7-TES-18365 was treated with 0.2 M HCl in acetonitrile to give 8.08 g of compound 18365 at 97.09% HPLC purity after recrystallization from ethyl acetate: heptane (5.8:11.7 mL/g).

m.p.=231° C. $^1$HNMR (400 MHz, CDCl$_3$) δ (ppm): 0.94-1.08 (m, 2H), 1.09-1.15 (m, 2H), 1.17 (s, 3H), 1.28 (s, 3H), 1.32-1.45 (m, 1H), 1.68 (s, 3H), 1.70 (s, 1H), 1.75-1.83 (m, 1H), 1.85 (s, 3H), 1.86-2.05 (m, 3H), 2.06-2.16 (bm 1H), 2.16-2.31 (m, 2H), 2.31-2.37 (m, 1H), 2.39 (s, 3H), 2.49-2.55 (m, 1H), 2.56 (d, J=3.75 Hz, 1H), 3.41 (d, J=5.11 Hz, 1H), 3.82 (d, J=7.16 Hz, 1H), 4.19 (d, J=8.52 Hz, 1H), 4.3 (d, J=8.52 Hz, 1H), 4.37-4.46 (m, 1H), 4.67 (dd, J=5.24, 2.13 Hz, 1H), 4.75-4.87 (m, 1H), 4.94 (bd, J=10.59, 1.56 Hz, 1H), 5.43 (d, J=9.72 Hz, 1H), 5.53 (d, J=9.38 Hz, 1H), 5.66 (d, J=7.16 Hz, 1H), 6.27 (m, 1H), 6.29 (s, 1H), 7.02 (dd, J=5.19, 3.59 Hz, 1H), 7.10 (d, J=3.41 Hz, 1H), 7.3 (dd, J=5.19, 1.19 Hz, 1H), 7.52 (dd, J=8.03, 7.68 Hz, 2H), 7.63 (dd, J=8.08, 7.34 Hz, 1H), 8.14 (d, J=7.5 Hz, 2H).

EXAMPLE 10

Compound 19244

Using the deprotection procedure described above, 10.61 g (10.07 mmol) of the 2'-MOP-7-TES-19244 was treated with 0.2 M HCl in acetonitrile to give 5.70 g (6.57 mmol, 65%) of compound 19244 at 97.59% HPLC purity after recrystallization from ethyl acetate: heptane (6.0:11.0 mL/g).

$^1$HNMR (400 MHz, CDCl$_3$) δ (ppm): 1.16 (s, 3H), 1.24 (t, J=7.60 Hz, 3H), 1.27 (s, 3H), 1.32-1.46 (m, 1H), 1.65 (m, 1H), 1.68 (s, 3H), 1.70 (s, 1H), 1.87-2.05 (m, 3H), 2.12 (bm, 1H), 2.16-2.31 (m, 2H), 2.31-2.38 (m, 1H), 2.39 (s, 3H), 2.44-2.65 (m, 4H), 3.41 (d, J=5.28 Hz, 1H), 3.81 (d, J=6.99 Hz, 1H), 4.19 (d, J=8.52 Hz, 1H), 4.30 (d, J=8.52 Hz, 1H), 4.38-4.47 (m, 1H), 4.66 (dd, J=5.27, 2.15 Hz, 1H), 4.8 (bm, J=7.4 Hz, 1H), 4.94 (bd, J=9.78, 1.54 Hz, 1H), 5.42 (d, J=9.56 Hz, 1H), 5.53 (d, J=9.22 Hz, 1H), 5.66 (d, J=7.16 Hz, 1H), 6.26 6.30 (s, 1H), 7.03 (dd, J=5.18, 3.42 Hz, 1H), 7.10 (d, J=3.58 Hz, 1H), 7.30 (dd, J=5.14, 1.2 Hz, 1H), 7.52 (dd, J=8.17, 7.61 Hz, 2H), 7.63 (dd, J=8.1, 7.43 Hz, 1H), 8.12 (d, J=7.50).

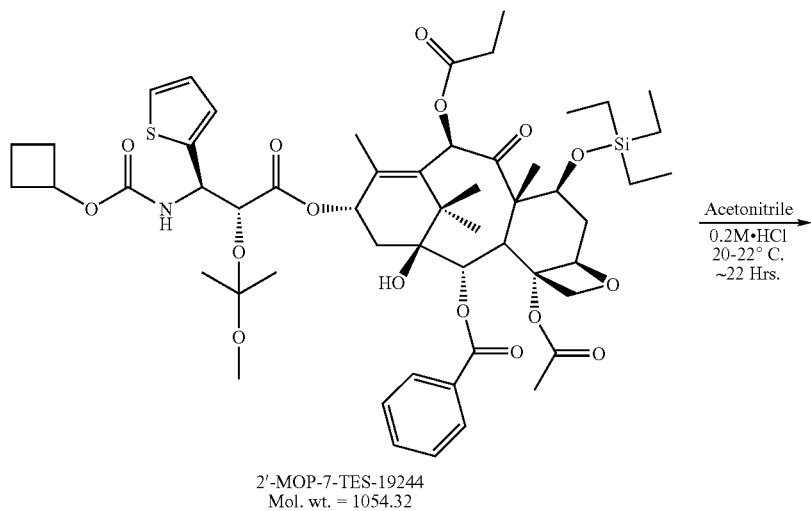

2'-MOP-7-TES-19244
Mol. wt. = 1054.32

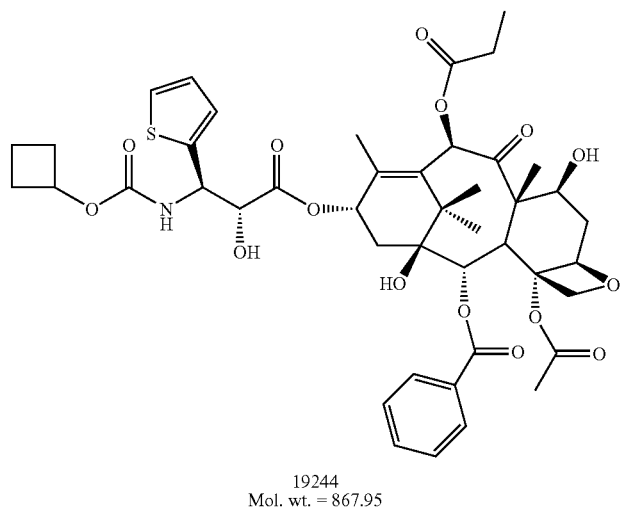

19244
Mol. wt. = 867.95

EXAMPLE 11

Racemic SIT302

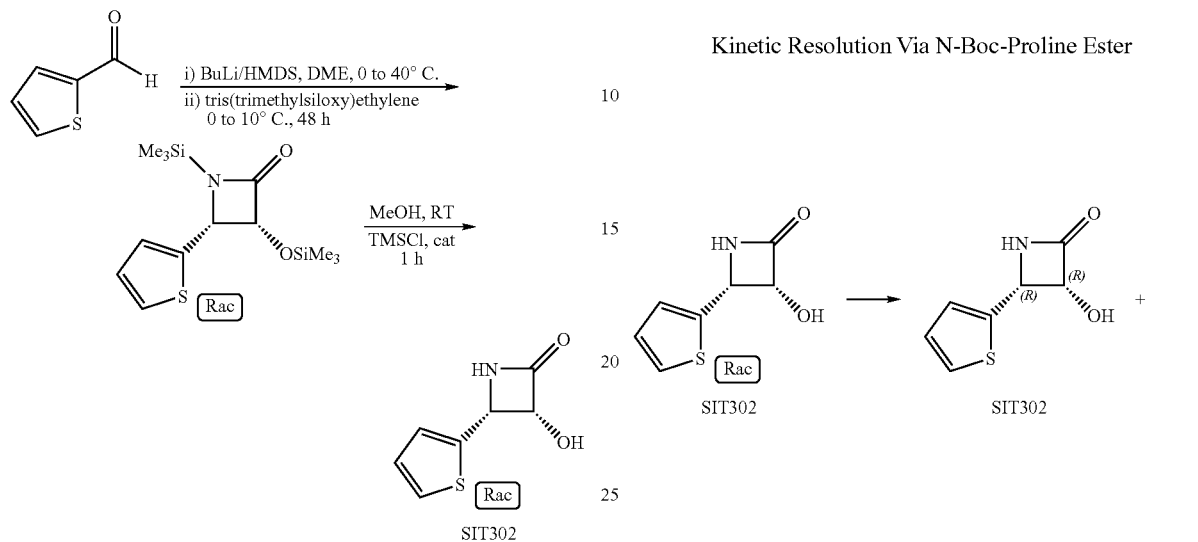

To a solution of hexamethyldisilazane (HMDS, 230 mL, 1.1 mol) in anhydrous dimethoxyethane (100 mL) at 0° C. was added a 2.5 M solution of n-butyllithium (nBuLi, 400 mL, 1.0 mol) over 20 min to maintain the reaction temperature at less than 40° C. After the addition, 2-thiophenecarboxaldehyde (112.15 g, 1.0 mol) was added to the reaction mixture over 30 min to maintain the reaction temperature at less than 40° C. After the addition was complete the mixture was cooled to 0° C. and tris(trimethylsiloxy)ethylene (322 g, 1.1 mol) was added and the mixture was stirred until reaction was complete (48 h), as determined by the disappearance of the starting ethylene material. The reaction mixture was quenched with trimethylsilylchloride (TMSCl, 108.16 g, 1.0 eq.) and diluted with hexanes (500 mL). The lithium salt was filtered off via a sintered funnel. The filtrate was concentrated to give a solid. Hexanes (500 mL) was added and the mixture was stirred at 0° C. for 45 min before harvesting via a Buchner funnel. The filter cake was washed with cold hexanes to give an off-white solid of the crude (214.5 g) racemic intermediate bis-(trimethylsilyl)-SIT302. ($^1$H-NMR (400 MHz, CDCl$_3$) ppm: 0.0 (s, 3H), 0.17 ppm (s, 3H), 4.94 (d, J=5.0 Hz, 1H), 5.06 (d, J=5.0 Hz, 1H), 6.95 (dd, J=3.68, 4.91, 1H), 7.03 (dd, J=3.68, 1.15 Hz, 1H), 7.32 (dd, 4.91, 1.15 Hz, 1H)).

The bis-silylated intermediate was taken up in anhydrous methanol (500 mL) and treated with a catalytic amount of trimethylsilylchloride (5.4 g, 0.05 mol) at ambient 20 to 24° C. to remove the two trimethylsilyl protecting groups. The desilylation was complete in a period of 1 h, as monitored via TLC (3:1 ethyl acetate:hexanes) to give the final product (Rf~0.2). The reaction mixture was basified with triethylamine (12.7 mL) and concentrated to give a slurry of crystalline product. Ethyl acetate (500 mL) was added and concentrated at 40° C. to a thick slurry before cooling ambient temperature (20 to 24° C.). The crystals were collected by vacuum filtration through a Buchner funnel and washed with cold ethyl acetate and dried to a constant weight of 74.5 g (44%) of the racemic SIT302. Isolation of the second crops were not attempted.

mp: 125-128° C., $^1$H-NMR (400 MHz, CDCl$_3$), δ (ppm): 2.27 (d, 9.74 Hz, 1H), 5.10 (m, 1H), 5.17 (d, 4.92 Hz, 1H), 6.23 (bm, 1H), 7.10 (om, 2H), 7.37 (dd, 1.71, 4.50 Hz, 1H).

EXAMPLE 12

Kinetic Resolution Via N-Boc-Proline Ester

To a clear anhydrous solution of the racemic SIT302 (846 g, 5.0 moles) and N-Boc-proline anhydride (1132 g, 2.75 moles, Benoiton N. L. et al., Synthesis 1978, 928) in acetonitrile, under nitrogen and mechanical stirring, at 0 to 5° C. was added N-methylbenzimidazole (6.6 g, 0.05 mol) was added to catalyze the kinetically controlled esterfication. After stirring at 0 to 5° C. for 24 h, TLC (3:1 E/H, CAM staining) and HNMR monitoring indicated that the ester to alcohol ratio was 37:63. An additional 1% of N-methylbenzimidazole (6.6 g, 0.05 mol) was added to drive the ratio to 50:50 after another 24 h stirring. The mixture warmed to ambient temperature and the solvent was removed under vacuum and then ethyl acetate (4 L) was added. The mixture was further concentrated to remove approximately 1.50 L of the solvents. The mixture was allowed to stand at an ambient temperature of 20 to 22° C. for 1 h before the crystals were collected by vacuum filtration and washed with cold ethyl acetate. The crystals were dried to a constant weight of 252 g (60% yield) and 99.4% optical purity. The mother liquor was further processed and washed with 3% acetic acid in water and the ethyl acetate was concentrated to a volume of approximately 1 L to give a 2nd crop of crystals (52 g at 99.1 optical purity). The combined total yield was 71.9% at >99% in chemical and optical purity.

$[\alpha]_D^{20}$=+120 (MeOH, 1.2), mp: 168-171° C. $^1$H-NMR (400 MHz, CDCl$_3$) δ (ppm): 2.27 (d, 9.74 Hz, 1H), 5.10 (m, 1H), 5.17 (d, 4.92 Hz, 1H), 6.23 (bm, 1H), 7.10 (om, 2H), 7.37 (dd, 1.71, 4.50 Hz, 1H).

EXAMPLE 13

N-CPentO-(O-MOP)—SIT302

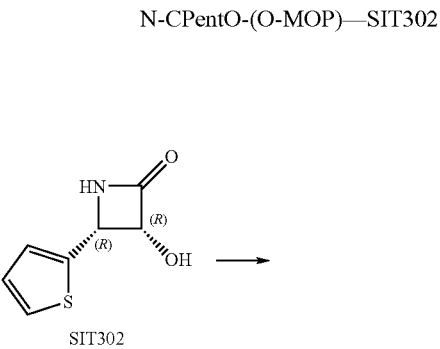

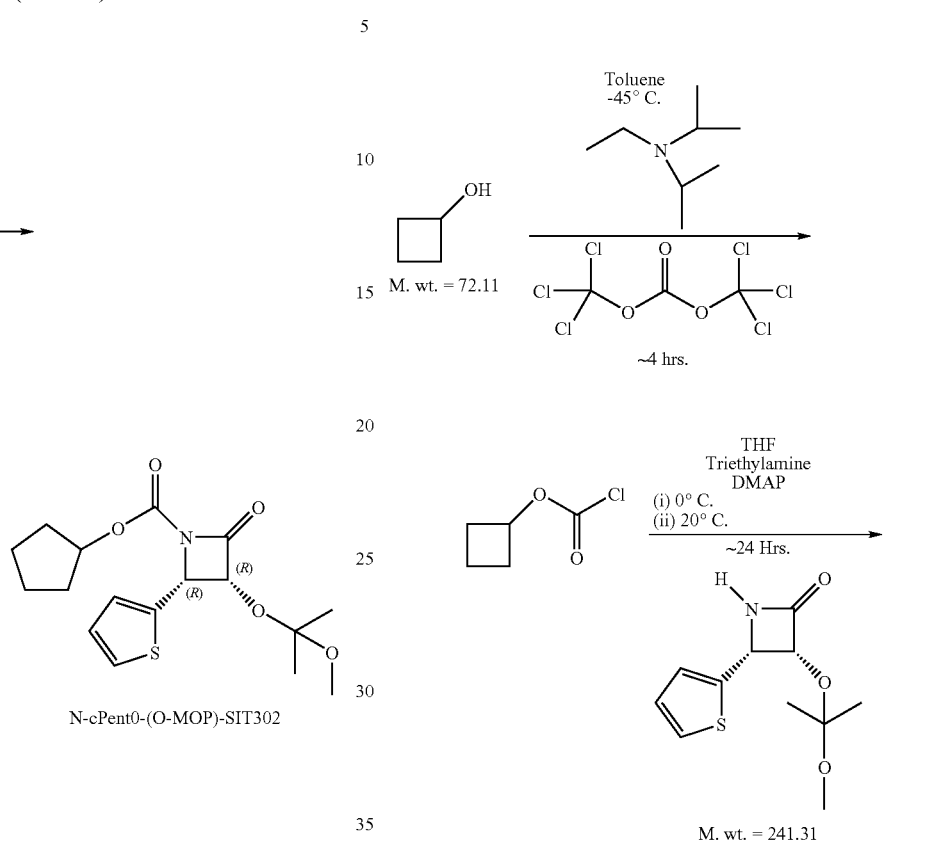

EXAMPLE 14

O-MOP-N-Cyclobutoxycarbonyl-SIT302

To a solution of triphosgene (5.5 g, 18.54 mmol) in toluene (45.0 mL) at −45° C. was added diisopropylethylamine (0.89 mL, 5.15 mmol) dropwise under a nitrogen atmosphere. The mixture was charged with cyclopentanol (4.72 mL, 51.5 mmol) dropwise, and stirred for 1 hour. The progress of cyclopentyl chloroformate formation was monitored by NMR. In a separate flask, 3.5 g (20.68 mmol) of SIT 302 was dissolved in 100 mL of anhydrous tetrahydrofuran under an atmosphere of nitrogen and cooled to −10° C. To this solution was added p-toluenesulfonic acid (196 mg, 1.03 mmol) followed by 2.37 mL (24.81 mmol) of 2-methoxypropene, dropwise. After 10 minutes, the first step of the one-pot reaction was complete and the solution was basified with triethylamine (8.6 mL, 62.04 mmol) and DMAP (500 mg, 4.09 mmol) and warmed to 0° C. The reaction was charged with 31.02 mL (31.02 mmol) of the toluene solution of cyclopentyl chloroformate and gradually warmed to room temperature. After 5 hours of stirring, 100 mL of heptane was added and the organic mixture was washed with 100 mL of $H_2O$, 100 mL of aqueous sodium bicarbonate solution, and 100 mL of brine. The organic layer was passed through a pad of triethylamine basified silica gel and flushed with 200 mL of a 1:1 mixture of ethyl acetate/heptane. Crystals formed on evaporation of the solvent giving 5.75 g of N-cPentO-(O-MOP)—SIT302 (78.8%).

m.p: 99° C.; $^1$H-NMR (400 MHz, J in Hz, CDCl$_3$): δ (ppm): 1.05 (s, 3H), 1.34 (s, 3H), 1.50-1.81 (m, 8H), 3.18 (s, 3H), 5.15 (m, 1H), 5.22 (d, J=5.63, 1H), 5.37 (d, J=5.63, 1H), 7.01 (dd, J=3.58, 5.11, 1H), 7.14 (d, J=0.68, 1H), 7.35 (dd, J=0.69, 4.94, 1H); $\alpha]_D^{20}$ D=+6.8° (C=1, MeOH).

Using the procedure described above, N-cBoc-(O-MOP)—SIT302 was prepared in 69.45% yield after recrystallization from hexanes containing 1% triethylamine.

m.p.=71° C. $\alpha]_D^{20}$=+14.7 (C=1, MeOH). $^1$HNMR (400 MHz, CDCl$_3$), δ (ppm): 1.06 (s, 3H), 1.34 (s, 3H), 1.54-1.64 (m, 2H), 1.73-1.81 (m, 1H), 2.0-2.18 (m, 2H), 2.32 (m, 2H), 3.18 (s, 3H), 4.99 (dt, J=7.53 Hz, 1H), 5.25 (d, J=5.68 Hz, 1H), 5.38 (d, J=5.88 Hz, 1H), 7.03 (dd, J=3.54, 5.24 Hz, 1H), 7.16 (dd, J=0.95, 3.60 Hz, 1H), 7.34 (dd, J=0.92, 5.06 Hz, 1H).

EXAMPLE 15

Comparison of In Vitro Cytotoxic Activity of Compounds 18926, 19244, 17932 and 18365 TO Paclitaxel and Docetaxel Using an MTT Assay Cytotoxicity and $IC_{50}$ Determination Compounds 18926, 18365, 17932, 19244, paclitaxel (PTX, 1), and docetaxel (TXT, 2) were analyzed for their absorbance of the test wells were divided by the absorbance of drug-free wells (after subtracting blank wells) and the concentration of the agent that resulted in 50% of the absorbance of untreated cultures ($IC_{50}$) was determined by analyses of best fit curve of the data. (GraphPad Prism version 4.00 for Windows). Studies were conducted by Taxolog, Inc., Tallahassee, Fla.

TABLE 2

| Compound | IN Vitro $IC_{50}$ (nm) HCT116 | IN Vitro $IC_{50}$ (nm) Panc | IN Vitro $IC_{50}$ (nm) DLD1 | IN Vitro $IC_{50}$ (nm) HT29 | IN Vitro $IC_{50}$ (nm) MSTO | IN Vitro $IC_{50}$ (nm) 786-0 | IN Vitro $IC_{50}$ (nm) A375 |
|---|---|---|---|---|---|---|---|
| Paclitaxel | 2.4 | 4.1 | >10 | 2.8 | 6.2 | >10 | 8.0 |
| Docetaxel | 0.9 | 1.9 | >10 | 1.3 | 4.0 | 6.2 | 2.4 |
| 17932 | 0.6 | 1.2 | 1.4 | 0.9 | | | |
| 18926 | 0.3 | 0.5 | 0.8 | 0.4 | 0.4 | 0.7 | 0.5 |
| 19244 | 0.4 | 1.2 | 1.8 | 0.6 | 0.6 | 0.9 | 0.6 |
| 18365 | 0.4 | 1.2 | 1.1 | 0.5 | 0.7 | 1.1 | 0.6 |

TABLE 3

| Compound | IN Vitro $IC_{50}$ (nm) A549 | IN Vitro $IC_{50}$ (nm) TK10 | IN Vitro $IC_{50}$ (nm) Malme3 | IN Vitro $IC_{50}$ (nm) OVCAR5 | IN Vitro $IC_{50}$ (nm) OVCAR4 | IN Vitro $IC_{50}$ (nm) HOP18 | IN Vitro $IC_{50}$ (nm) ske-mel28 | IN Vitro $IC_{50}$ (nm) SNB19 |
|---|---|---|---|---|---|---|---|---|
| Paclitaxel | 3.8 | 4.8 | 6.5 | | 2.9 | 7.2 | 5.4 | 6.1 |
| Docetaxel | 1.3 | 1.4 | 1.8 | 1.1 | 1.4 | 3.4 | 2.1 | 1.9 |
| 17932 | | | | | | | | |
| 18926 | 0.4 | 0.3 | 1.8 | 0.2 | 1.0 | 1.6 | 0.6 | 1.0 |
| 19244 | 0.5 | 0.4 | 1.1 | 0.6 | 2.7 | 1.5 | 2.0 | 0.9 |
| 18365 | 0.5 | 0.5 | 4.1 | 0.3 | 1.1 | 0.7 | 0.9 | 1.1 | effects), on proliferation of the following cell lines from American Type Tissue Culture: MALME-3 (human skin melanoma), MSTO-211H (human pleural mesothelioma), HT29 (human colon adenocarcinoma), DLD-1 (human colon adenocarcinoma), PANC-1 (human pancreatic adenocarcinoma), A549 (human lung carcinoma), A375 (human skin melanoma), 786-0 (human renal cell adenocarcinoma), SK-MEL-28 (human skin melanoma) and cell lines from NCI DCTD Tumor/Cell Line Repository: SNB-19 (human brain glioblastoma), HOP-18 (human lung NSCLC), OVCAR4 (human ovarian carcinoma) and OVCAR5 (human ovarian carcinoma), TK-10 (renal cell carcinoma). Compound 17932 was tested in four of these cell lines, while the remaining compounds were tested in all of these cell lines. All cell lines were maintained in RPMI-1640 tissue culture medium (TCM, supplemented with antibiotics and 10% fetal bovine serum) and cultured at 37° C. in humidified air containing 5% $CO_2$. To assess the antiproliferative effects of the test compounds, 172 μL of tumor cell suspension ($1.45 \times 10^4$ cells/ml) were added to each well of a 96-well plate and incubated for 24 h at 37° C. in 5% $CO_2$ in air to allow cells to adhere. Seven 2-fold drug dilutions in TCM/DMSO were performed in triplicate in separate 96-well plates and 28 μL was transferred to the wells containing tumor cells (200 μL final volume/0.1% DMSO). Plates were incubated for 72 h and cell viability was determined by adding 50 μL of warm TCM containing 5 mg/mL MTT (3-[4,5-dimethylthiazol-2-yl]-2,5-diphenyltetrazolium bromide) to each well and incubating for 1 h at 37° C. Plates were processed and the absorbances of the resulting solutions were measured by a plate reader at 570 nm. The

TABLE 4

| Resistance | DLD1 Colon MDR1+ | MSTO Mesothelioma MRP2/BCRP1 | 786-0 Renal MDR1+ | A375 Melanoma MRP9 |
|---|---|---|---|---|
| Paclitaxel | 41 | 6.2 | >10 | 8.0 |
| Docetaxel | 20 | 4.0 | 6.2 | 2.4 |
| 18926 | 0.8 | 0.4 | 0.7 | 0.5 |
| 18365 | 1.1 | 0.7 | 1.1 | 0.6 |
| 19244 | 1.8 | 0.6 | 0.9 | 0.5 |
| 17932 | 1.4 | NT | NT | NT |

NT = not tested

EXAMPLE 16

Comparison of In Vitro Cytotoxicity of Compounds 18365 and 19244 to Docetaxel (TXT) in the BxPC-3 Cancer Cell Line BxPC-3 cancer cell line (Source ATCC) and culture medium were purchased and provided by Oncodesign (France).

Tumor cells (5,000 cells per well) were plated in 96-well flat-bottom microtitration plates (Ref 167008, Batch 083310, Nunc, Dutscher, Brumath, France) and incubated at 37° C. for 24 hours before treatment in 100 μl of drug-free RPMI 1640 medium supplemented with 10% FBS. Tumor cell lines were incubated for 72 hours with 10 concentrations of both test substances and TXT (40 to 0.07 nM using ½ step dilutions). Experiments were repeated three times, each assay being issued from quadruplicate. Control cells were treated with the vehicle alone. At the end of treatments, the cytotoxic activity was evaluated by a MTT assay. These studies were conducted at Oncodesign, France.

Summary results of 18365, 19244, and TXT compounds $IC_{50}$ determination experiments on BxPC-3 cell lines.

TABLE 5

| Cell line | | $IC_{50}$ (nM) | | |
| --- | --- | --- | --- | --- |
| | | 18365 | 19244 | TXT |
| BxPC-3 | Exp 1 | 0.79 | 0.53 | 0.93 |
| | Exp 2 | 1.07 | 0.66 | 2.20 |
| | Exp 3 | 0.99 | 1.03 | 0.73 |

TABLE 6

| Cell line | $IC_{50}$ Mean ± SD (nM) | | |
| --- | --- | --- | --- |
| | 18365 | 19244 | TXT |
| BxPC-3 | 0.95 ± 0.14 | 0.74 ± 0.26 | 1.29 ± 0.80 |

EXAMPLE 17

In Vivo Activity of Compounds 18926 and 18365 in Nude Mice Bearing MX1 Human Tumor Xenografts This xenograft study was conducted at Piedmont Research Center, NC (PRC). Female athymic nude mice (nu/nu Harlan) were 7 weeks old, with a body weight (BW) range of 15.1-24.6 g, on Day 1 (D1) of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® Bed-o-Cobs® Laboratory Animal Bedding in static microisolators on a 12-hour light cycle at 21-22° C. (70-72° F.) and 40-60% humidity. PRC specifically complies with the recommendations of the *Guide for Care and Use of Laboratory Animals* with respect to restraint, husbandry, surgical procedures, feed and fluid regulation, and veterinary care. The animal program at PRC is accredited by Association for Assessment and Accreditation of Laboratory Animal Care (AALAC) International, which assures compliance with accepted standards for the care and use of laboratory animals.

Tumor Implantation

The human MX-1 breast carcinoma utilized in this study was maintained in athymic nude mice by serial engraftment. A tumor fragment (1 mm$^3$) was implanted s.c. into the right flank of each test mouse. Tumors were monitored twice weekly and then daily as their mean volume approached 80-120 mm$^3$. On D1 of the study, the animals were sorted into treatment groups with tumor sizes of 63-144 mm$^3$ and group mean tumor sizes of ~88 mm$^3$. Tumor size, in mm$^3$, was calculated from:

$$\text{Tumor Volume} = \frac{w^2 \times l}{2}$$

where w=width and l=length in mm of the tumor.

Tumor weight was estimated with the assumption that 1 mg is equivalent to 1 mm$^3$ of tumor volume.

Compounds 18365 and 18926 were formulated in 10% ethanol, 10% Cremophor EL® and 80% dextrose 5% in water and administered with a dosing volume of 0.3 mL per 20 gram mouse and scaled to the weight of each mouse. TXT was dissolved in 50% ethanol and 50% Tween® 80 to prepare a 6.67× solution, which was diluted with D5W to yield an i.v. dosing solution containing 7.5% ethanol and 7.5% Tween® 80 and 85% D5W and administered with a dosing volume of 0.2 mL per 20 gram mouse and scaled to the weight of each mouse. All drug solutions were prepared fresh on the day of dosing.

Treatment

Mice were sorted into groups with five mice per group. Intravenous (i.v.) treatments were given once on D1 (qd×1). Control Group 1 received Vehicle 1 intravenously. Groups 9-11 received compound 18365 i.v. at 7.5, 15, and 30 mg/kg, respectively. Groups 12-14 received compound 18926 i.v. at 7.5, 15, and 30 mg/kg, respectively. Group 25 received compound 2 i.v. at 25 mg/kg.

Endpoint

Each animal was euthanized when its neoplasm reached the predetermined endpoint size (1500 mm$^3$) or at the end of the study, whichever came first. The time to endpoint (TTE) for each mouse was calculated by the following equation:

$$TTE = \frac{\log_{10}(\text{endpoint volume}) - b}{m}$$

where TTE is expressed in days, endpoint volume is in mm$^3$, b is the intercept, and m is the slope of the line obtained by linear regression of a log-transformed tumor growth data set. The data set is comprised of the first observation that exceeded the study endpoint volume and the three consecutive observations that immediately preceded the attainment of the endpoint volume. The calculated TTE is usually less than the day on which an animal is euthanized for tumor size. Animals that do not reach the endpoint are assigned a TTE value equal to the last day of the study (61 days). An animal classified as having died from treatment-related (TR) causes or non-treatment-related metastasis (NTRm) causes is assigned a TTE value equal to the day of death. An animal classified as having died from non-treatment-related (NTR) causes is excluded from TTE calculations. Treatment efficacy was determined from tumor growth delay (TGD), which is defined as the increase in the median TTE for a treatment group compared to the control group:

$$TGD = T - C,$$

expressed in days, or as a percentage of the median TTE of the control group:

$$\% \; TGD = \frac{T - C}{C} \times 100$$

where:
T=median TTE for a treatment group,

C=median TTE for control Group 1.

MTV and Criteria for Regression Responses

Treatment efficacy was also determined from the tumor volumes of animals remaining in the study on the last day, and from the number of regression responses. The MTV (n) is defined as the median tumor volume on D61 in the number of animals remaining, n, whose tumors have not attained the endpoint volume. Treatment may cause a partial regression (PR) or a complete regression (CR) of the tumor in an animal. A PR indicates that the tumor volume was 50% or less of its D1 volume for three consecutive measurements during the course of the study, and equal to or greater than 13.5 mm$^3$ for one or more of these three measurements. A CR indicates that the tumor volume was less than 13.5 mm$^3$ for three consecutive measurements during the course of the study. An animal with a CR at the termination of a study is additionally classified as a tumor-free survivor (TFS).

Toxicity

Animals were weighed daily on D1-5, then twice weekly until the completion of the study. The mice were examined frequently for overt signs of any adverse, drug related side effects. Acceptable toxicity for the maximum tolerated dose (MTD) was defined as a group mean BW loss of less than 20% during the test, and not more than one TR death among ten animals. A death is classified as TR if it is attributable to treatment side effects as evidenced by clinical signs and/or necropsy, or due to unknown causes during the dosing period or within 10 days of the last dose. A death is classified as NTR if there is no evidence that the death was related to treatment side effects. A death is classified as NTRm if necropsy indicates that it may have resulted from tumor dissemination by invasion and/or metastasis. Control Group 1 received Vehicle 1 i.v., and served as the control for TTE analyses, and as the primary control for statistical evaluations of i.v. treatment groups. The median TTE for Group 1 mice was 32.1 days. Tumors in all five mice grew to the 1500 mm$^3$ endpoint volume. Therefore, the maximum % TGD possible in this 61-day study was 90. A summary of the results are shown below.

Compound 18365 at 15 and 30 mg/kg (Groups 10 and 11) caused 6.8% and 16% maximum group mean BW losses, respectively, on D5. Compound 18926 at 7.5, 15, and 30 mg/kg (Groups 12-14) caused 7.6% (D3), 6.6% (D4), and 15.5% (D5) maximum group mean BW losses, respectively. The tumor model performed satisfactorily in that all tumors in vehicle-treated Group 1 attained the 1500 mm$^3$ endpoint volume, and none regressed. Therefore, all survivors and regression responses could be attributed to the drug treatments. A minimal effective dose was defined as the lowest dose that produced statistically significant results, and also generated at least one D61 survivor and/or at least one regression response. Vehicle 1 treatments produced median TTEs of 32.1 Group 1. Based on the median TTE for Group 1, the maximum % TGD for this study was 90. Compound 18365 exhibited non-significant activity at 7.5 mg/kg (Group 9). Compound 18365 was minimally effective at 15 mg/kg (Group 10), which yielded 1 PR and 2 TFS, with 6.8% group mean BW loss. The 30 mg/kg regimen (Group 11) generated 5 TFS, with 16% group mean BW loss. Compound 18926 exhibited non-significant activity at 7.5 mg/kg (Group 12). Activity increased sharply at the minimally effective 15 mg/kg dose (Group 13), which generated 4 TFS, with 6.6% group mean BW loss. The 30 mg/kg treatment (Group 14) yielded 5 TFS and caused 15.5% mean BW loss. Compound 2 at 25 mg/kg qd×1 yielded 1 transient CR and 4 TFS, with 10.2% group mean weight loss. The mean tumor growth for this study is shown in FIG. 1.

EXAMPLE 18

In Vivo Activity of Compound 19244 in Nude Mice Bearing MX1 Human Tumor Xenografts This study was conducted at PRC as previously described. Compound 19244 was dosed on an every four day schedule for four doses. Docetaxel was dosed weekly for three doses. On D1 of the study, the animals were sorted into treatment

TABLE 7

| Group | n | Agent | Vehicle | mg/kg | Route | Schedule | Median TTE | T-C | % TGD | MTV (n), Day 60 | PR | CR | TFS | BW Nadir | TR | NTR |
|---|---|---|---|---|---|---|---|---|---|---|---|---|---|---|---|---|
| 1[#] | 5 | vehicle 1 | 10% EC in D5W | — | iv | qd × 1 | 32.14 | — | — | — | 0 | 0 | 0 | −0.6% (5) | 0 | 0 |
| 9 | 5 | 18365 | 10% EC in D5W | 7.5 | iv | qd × 1 | 36.29 | 4.15 | 12.92 | — | 0 | 0 | 0 | −3.8% (4) | 0 | 0 |
| 10 | 5 | 18365 | 10% EC in D5W | 15 | iv | qd × 1 | 56.65 | 24.51 | 76.26 | 1098.50 (1) | 1 | 2 | 0 | −6.8% (5) | 0 | 0 |
| 11 | 5 | 18365 | 10% EC in D5W | 30 | iv | qd × 1 | 61 | 28.86 | 89.79 | 0.00 (5) | 0 | 5 | 5 | −16.0% (5) | 0 | 0 |
| 12 | 5 | 18926 | 10% EC in D5W | 7.5 | iv | qd × 1 | 37.43 | 5.29 | 16.46 | — | 0 | 0 | 0 | −7.6% (3) | 0 | 0 |
| 13 | 5 | 18926 | 10% EC in D5W | 15 | iv | qd × 1 | 61 | 28.86 | 89.79 | 0.00 (4) | 0 | 4 | 4 | −6.6% (4) | 0 | 0 |
| 14 | 5 | 18926 | 10% EC in D5W | 30 | iv | qd × 1 | 61 | 28.86 | 89.79 | 0.00 (5) | 0 | 5 | 5 | −15.5% (5) | 0 | 0 |
| 25 | 5 | 2 | D5W | 25 | iv | qd × 1 | 61 | 28.86 | 89.79 | 0.00 (5) | 0 | 5 | 4 | −10.2% (5) | 0 | 0 | groups with tumor sizes of 63-144 mm³ and group mean tumor sizes of ~87 mm³. Intravenous compound 19244 generated: 3 TFS and 2 transient CRs at 7.5 mg/kg; 5 TFS at 15 mg/kg; and 4 TFS and 1 PR at 30 mg/kg. Respective maximum group mean BW losses (3.1%, 7.6%, and 18.9% on D19) approximately doubled with dosage. A summary of the results are shown.

Figure 3:
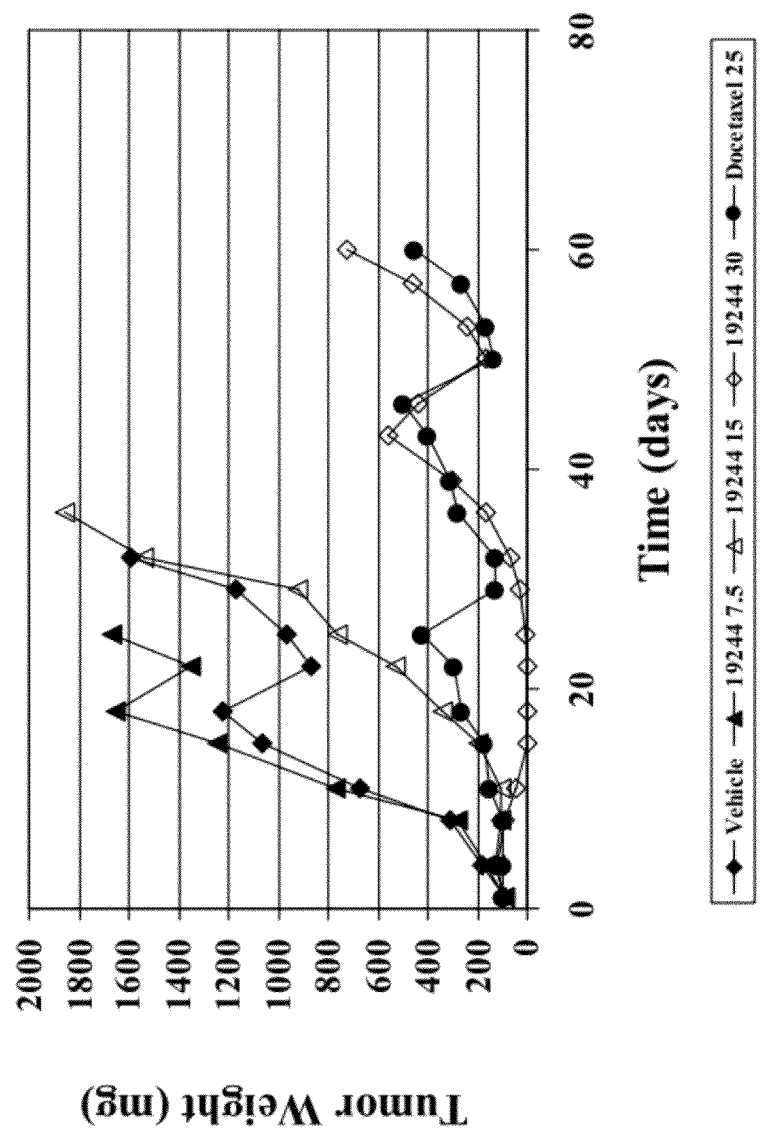
FIG. 3 depicts mean tumor growth curves for mice treated with compound 19244 and docetaxel in the MX1 study (e223) (i.v. single dose).

The mean tumor growth for this study is shown in FIG. 3.

EXAMPLE 20

In Vivo Activity of Compound 19244 in Nude Mice Bearing SKMES Human Tumor Xenografts This study was conducted at PRC as previously described. SKMES is a human lung cancer cell line. In the present study,

TABLE 8

| | | | | Treatment Regimen 1 | | | | | | | | | | | | |
|---|---|---|---|---|---|---|---|---|---|---|---|---|---|---|---|---|
| Group | n | Agent | Vehicle | mg/kg | Route | Schedule | Median TTE | T-C | % TGD | MTV (n), Day 57 | PR | CR | TFS | BW Nadir | TR | NTR |
| 1$ | 5 | vehicle 1 | 5% EC in Saline | — | po | q4d × 4 | 17.97 | — | — | — | 0 | 0 | 0 | — | 0 | 0 |
| 2 | 5 | vehicle 2 | 10% EC in D5W | — | iv | q4d × 4 | 20.34 | 2.37 | 13.17 | — | 0 | 0 | 0 | — | 0 | 0 |
| 5 | 5 | 19244 | 10% EC in D5W | 7.5 | iv | q4d × 4 | 57 | 39.03 | 217.17 | 0.00 (5) | 0 | 5 | 3 | −3.1% (19) | 0 | 0 |
| 6 | 5 | 19244 | 10% EC in D5W | 15 | iv | q4d × 4 | 57 | 39.03 | 217.17 | 0.00 (5) | 0 | 5 | 5 | −7.6% (19) | 0 | 0 |
| 7 | 5 | 19244 | 10% EC in D5W | 30 | iv | q4d × 4 | 57 | 39.03 | 217.17 | 0.00 (5) | 1 | 4 | 4 | −18.9% (19) | 0 | 0 |
| 15 | 5 | 2 | D5W | 25 | iv | qwk × 3 | 57 | 39.03 | 217.17 | 0.00 (5) | 0 | 5 | 5 | −10.9% (22) | 0 | 0 |

Figure 2:
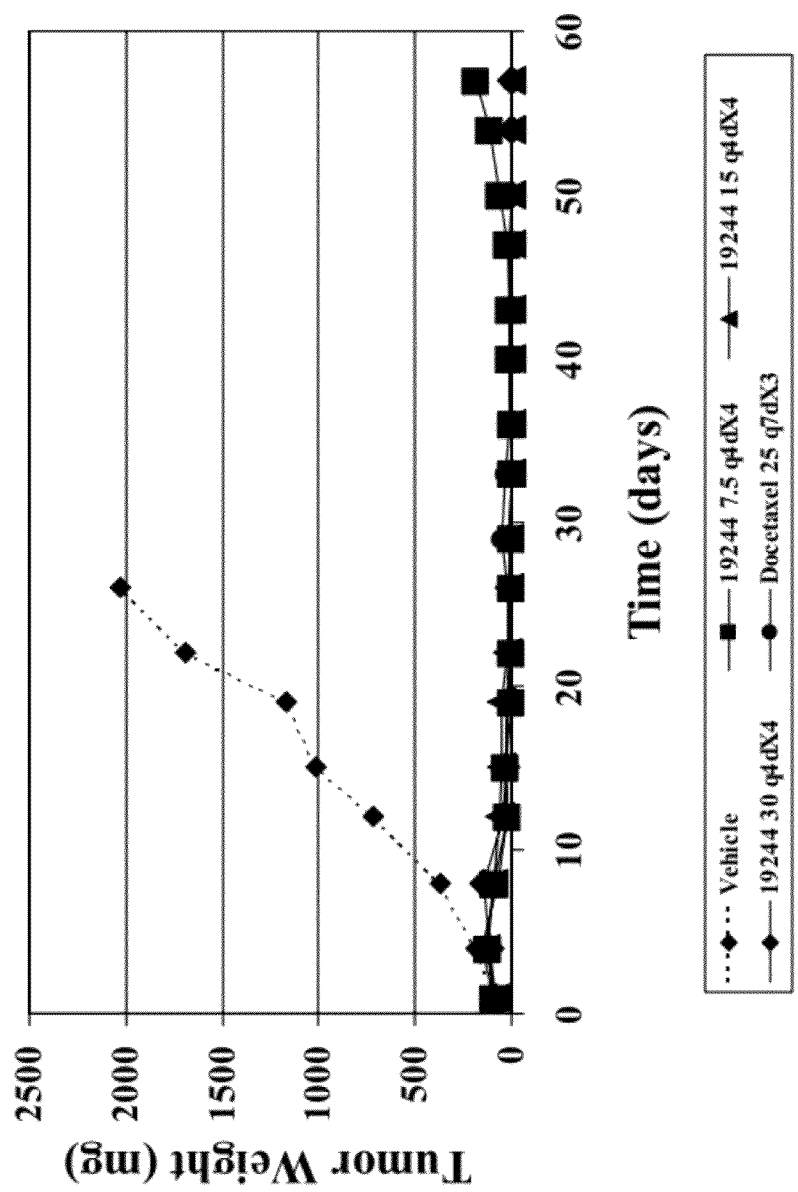
FIG. 2 depicts mean tumor growth curves for mice treated with compound 19244 in the MX1 study (e220) (i.v. q4d×4 doses).

The mean tumor growth for this study is shown in FIG. 2.

EXAMPLE 19

In Vivo Activity of Compound 19244 in Nude Mice Bearing MX1 Human Tumor Xenografts This study was conducted at PRC as previously described. Compound 19244 and docetaxel were dosed on a daily schedule. Three compound 2-treated mice survived to D60, and three tumors regressed (1 transient CR and 2 TFS). Compound 19244 at 7.5 and 15 mg/kg produced respective % TGDs of −3 and 83, and nonsignificant activities (logrank test). No 60 day survivors or regressions occurred at these lower doses. At 30 mg/kg, compound 19244 produced a % TGD of 235, and exhibited significant activity; two mice survived to D60, and all tumors regressed (1 PR, 2 transient CRs, and 2 TFS. A summary of the results are shown.

groups with tumor sizes of 63-144 mm³ and group mean tumor sizes of ~87 mm³. Intravenous compound 19244 generated: 3 TFS and 2 transient CRs at 7.5 mg/kg; 5 TFS at 15 mg/kg; and 4 TFS and 1 PR at 30 mg/kg. Respective maximum group mean BW losses (3.1%, 7.6%, and 18.9% on D19) approximately doubled with dosage. A summary of the results are shown. compound 2 and all agents were administered as i.v. monotherapies in a single 30 mg/kg dose (qd×1). The test agents were formulated in a vehicle consisting of 5% ethanol and 95% of 20% Liposyn® II. Control mice received this vehicle qd×1. Compound 2 was formulated in a vehicle consisting of 7.5% ethanol, 7.5% Tween®80, and 85% D5W (5% dextrose in water). Dosing began on Day 1 in groups of five nude mice bearing well-established (~124 mm³) subcutaneous SKMES lung tumors. The endpoint volume for tumor growth was 1,500 mm³. The study was terminated on Day 23.

TABLE 9

| | | | | Treatment Regimen 1 | | | | | | | | | | | | |
|---|---|---|---|---|---|---|---|---|---|---|---|---|---|---|---|---|
| Group | n | Agent | Vehicle | mg/kg | Route | Schedule | Median TTE | T-C | % TGD | MTV (n), Day 60 | PR | CR | TFS | BW Nadir | TR | NTR |
| 1# | 5 | vehicle | 10% EC in D5W | — | iv | qd × 1 | 17.17 | — | — | — | 0 | 0 | 0 | — | 0 | 0 |
| 2 | 5 | 19244 | 10% EC in D5W | 7.5 | iv | qd × 1 | 16.72 | −0.45 | −2.64 | — | 0 | 0 | 0 | — | 0 | 0 |
| 3 | 5 | 19244 | 10% EC in D5W | 15 | iv | qd × 1 | 31.49 | 14.32 | 83.42 | — | 0 | 0 | 0 | — | 0 | 0 |
| 4 | 5 | 19244 | 10% EC in D5W | 30 | iv | qd × 1 | 57.59 | 40.42 | 235.44 | 0.00 (2) | 1 | 4 | 2 | — | 0 | 0 |
| 11 | 5 | 2 | D5W | 25 | iv | qd × 1 | 60 | 42.83 | 249.47 | 0.00 (3) | 0 | 3 | 2 | — | 0 | 0 |

TABLE 10

| | | | | Treatment Pegimen 1 | | | | | | | | | |
|---|---|---|---|---|---|---|---|---|---|---|---|---|---|
| Group | n | Agent | mg/kg | Route | Schedule | Median TTE | T-C | % TGD | MTV (n), Day 23 | PR | CR | TFS | TR | NTR NTRm |
| 1[#] | 5 | Vehicle | — | iv | qd × 1 | 14.2 | — | — | — | 0 | 0 | 0 | 0 | 0 |
| 16 | 5 | 19244 | 30 | iv | qd × 1 | 23 | 8.8 | 61.94 | 352.00 (5) | 0 | 1 | 1 | 0 | 0 |
| 18 | 5 | 2 | 30 | iv | qd × 1 | 23 | 8.8 | 61.94 | 166.75 (4) | 2 | 0 | 0 | 0 | 0 |

Compound 19244 was active single dose in this model with one complete response and 1 TFS.

Figure 4:
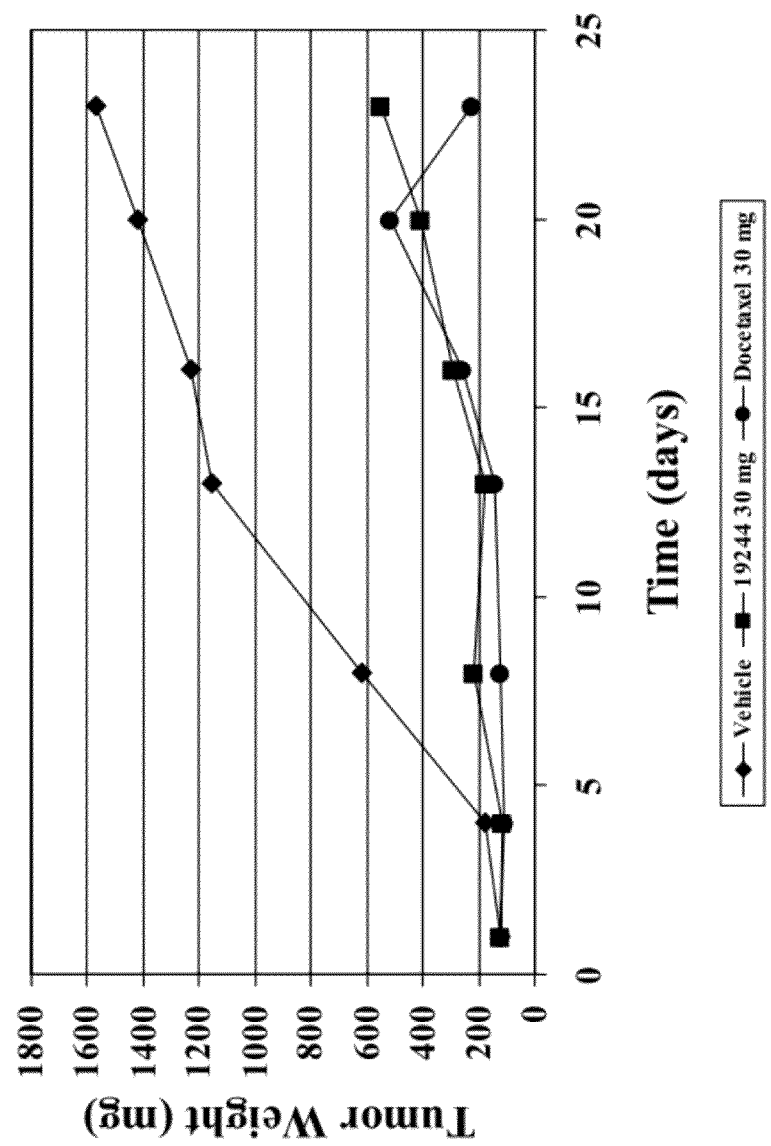
FIG. 4 depicts mean tumor growth curves for mice treated with compound 19244 and docetaxel in the SKMES study (e220) (i.v. single dose).

The mean tumor growth for this study is shown in FIG. 4.

EXAMPLE 21

In Vivo Activity of Compound 19244 in Nude Mice Bearing SKMES Human Tumor Xenografts Compound 19244 was tested for antitumor activity against human SKMES lung carcinoma xenografts at PRC. The compound 19244 was administered at 30 mg/kg, intravenously (i.v.) once daily every four days for four doses (q4d×4), in a vehicle consisting of 5% ethanol and 95% of 20% Liposyn® II. The control mice received this vehicle q4d×4. The positive reference group received 25 mg/kg compound 2 once weekly for three weeks (q7d×3) in a vehicle consisting of 7.5% ethanol, 7.5% Tween® 80, and 85% D5W (5% dextrose in water). Dosing began on Day 1 in groups of five nude mice bearing upstaged (~182 mm³) subcutaneous SKMES tumors.

Compound 19244 was active single dose in this model with two partial response and 3 TFS.

Figure 5:
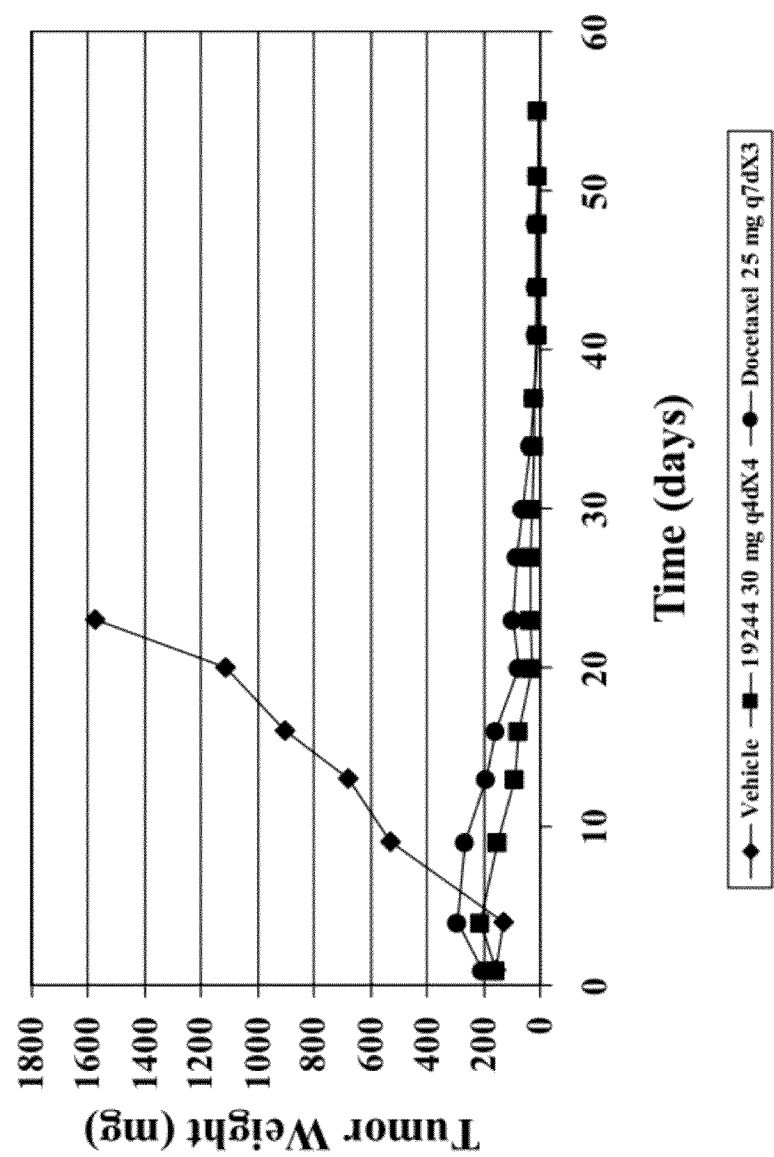
FIG. 5 depicts mean tumor growth curves for mice treated with compound 19244 and docetaxel in the SKMES study (e82) (compound 19244 dosed i.v. q4d×4 doses).

The mean tumor growth for this study is shown in FIG. 5.

EXAMPLE 22

Figure 6:
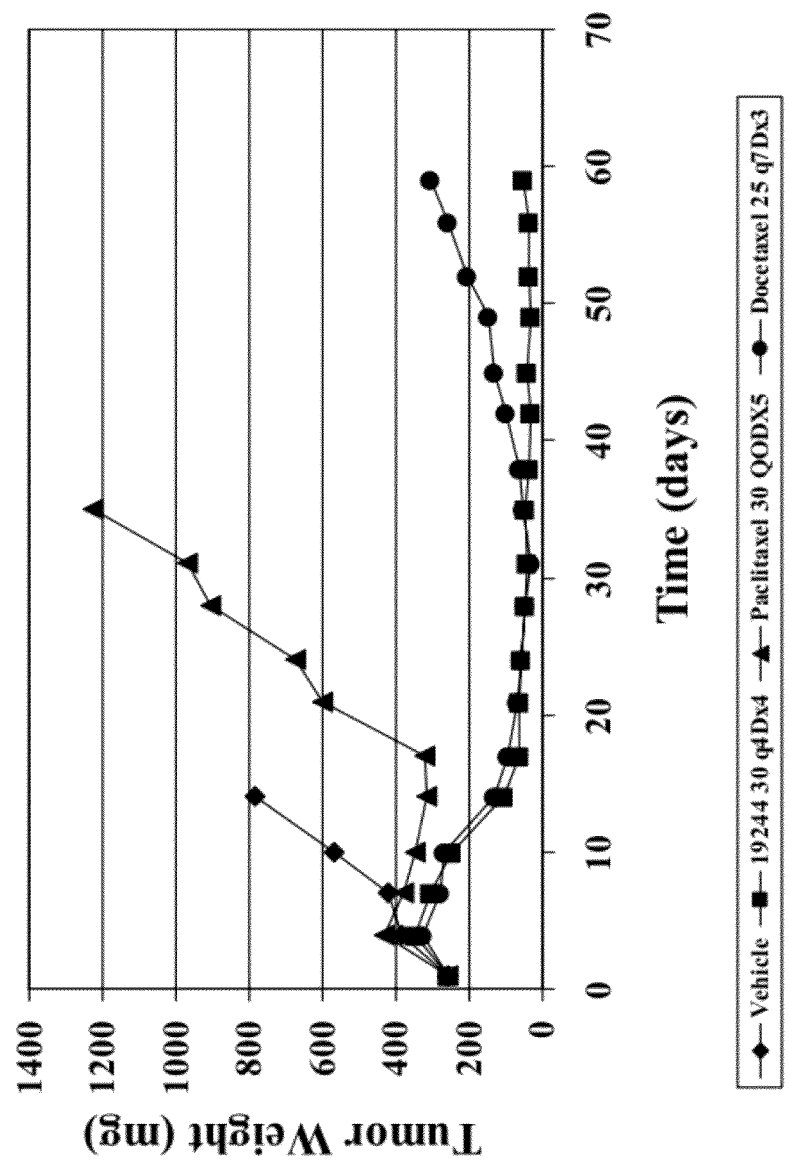
FIG. 6 depicts mean tumor growth curves for mice treated with compound 19244, paclitaxel, and docetaxel in the HT29 study (e138) (compound 19244 dosed i.v. q4d×4 doses).

In Vivo Activity of Compound 19244 in Nude Mice Bearing HT29 Human Tumor Xenografts Compound 19244 was tested by PRC for antitumor activity against human HT29 colon carcinoma xenografts. Compound 19244 was administered intravenously (i.v.) at 30 mg/kg, once daily every four days for four doses (q4d×4), in a vehicle of 5% ethanol and 95% of 20% Liposyn® II. Control mice received this vehicle q4d×4. There were six mice in each group. One positive reference group received 30 mg/kg paclitaxel q4d×4, and another received 25 mg/kg compound 2 once weekly for three weeks (q7d×3). Paclitaxel was formulated in 5% ethanol, 5% Cremophor EL®, and 90% dextrose (5%) in water (D5W). Compound 2 was formulated in 7.5% ethanol, 7.5% Tween® 80, and 85% D5W. Dosing began on Day 1 in groups of six nude mice bearing upstaged (~259 mm³) subcutaneous HT29 tumors. The endpoint volume for tumor growth was 1,000 mm³. The study duration was 59 days. Paclitaxel demonstrated relatively weak activity, while a well-tolerated compound 2 regimen produced one LTTFS and 4 PR responses. Compound 19244 outperformed compound 2 by yielding more regression responses and lower MTVs with compound 19244 yielding six regression responses, including 1 LTTFS. The mean tumor growth for this study is shown in FIG. 6.

TABLE 11

| Group | | Regimen 1 | | | | D 38 (mm³) | | | Max. BW Loss | Number of Death | |
|---|---|---|---|---|---|---|---|---|---|---|---|
| Number | N | Name | mg/kg | Route | Schedule | D45 (mm3) | D52 (mm³) | D 38 TTE | %; Day | TR | NTR |
| 1 | 6 | Vehicle | — | IV | Q4D × 4 | | | 18.1 ± 1.8 (6) | — | 0 | 0 |
| 16 | 6 | 19244 | 30 | IV | Q4D × 4 | 40 | 36.3 | | −10.5%; Day 14 | 0 | 0 |
| 21 | 6 | Paclitaxel | 30 | IV | Q4D × 4 | | | 27.5 ± 1.9 (6) | — | 0 | 0 |
| 22 | 6 | Docetaxel | 25 | IV | Q7D × 3 | 132.8 | 206.8 | | −6.6%; Day 21 | 0 | 0 |

EXAMPLE 23

In Vivo Activity of Compounds 18365, 18926, and 17932 in Nude Mice Bearing HT29 Human Tumor Xenografts This study was conducted at PRC. Each test agent was administered intravenously (i.v.), at 20, or 25, mg/kg, once daily every four days for four doses (q4d×4). The control mice received the test agent vehicle, 5% ethanol and 95% of 20% Liposyn® II, on the q4d×4 schedule. The positive reference group received 25 mg/kg compound 2 once weekly for three weeks (q7d×3), in a vehicle consisting of 7.5% ethanol, 7.5% Tween® 80, and 85% D5W (5% dextrose in water). Dosing began on Day 1 in groups of six nude mice bearing upstaged (~260 mm³) subcutaneous HT29 tumors. The endpoint volume for tumor growth was 1,000 mm³. The study duration was 61 days. Compound 2 produced 210% TGD, and yielded 1 LTTFS and 5 PR responses. The MTV, defined as the median tumor volume of animals remaining on the last day of the study (Day 61), was 196 mm³, for five mice. Compound 2 caused a tolerable group mean body-weight (BW) loss of 14.4%. 2. At 20 mg/kg, compound 17932 and compound 18926 produced MTVs of 78 mm³ and 83 mm³, respectively, which are lower than the 196-mm³ MTV of compound 2-treated mice. These test agents each yielded 5 PR responses, and no curative activity. At 25 mg/kg, compound 18365 produced five 61-day survivors. Compound 18365 demonstrated the greatest curative activity in the present study, with 2 CR and 4 PR responses along with 1 TR death.

TABLE 12

| Group | | | Regimen 1 | | | | Day 54 | | Max. BW Loss | Number of Death | |
|---|---|---|---|---|---|---|---|---|---|---|---|
| Number | N | Name | mg/kg | Route | Schedule | Day 51 mm$^3$ | Day 54 mm$^3$ | Day 54 TTE | %; Day | TR | NTR |
| 1 | 6 | % EtOH in Liposyn I | — | iv | q4d × 4 | | | 17.4 ± 3.3 (6) | — | 0 | 0 |
| 13 | 6 | 17932 | 20 | iv | q4d × 4 | 99.7 | 109.4 | | −19.3%; Day 16 | 0 | 0 |
| 14 | 6 | 18365 | 25 | iv | q4d × 4 | 112.8 | 124.7 | | −17.1%; Day 16 | 1 | 0 |
| 19 | 6 | 18926 | 20 | iv | q4d × 4 | 142.3 | 147 | | −20.7%; Day 16 | 0 | 0 |
| 22 | 6 | 2 | 25 | iv | q7d × 3 | 131.1 | 180.6 | | −14.4%; Day 19 | 0 | 0 |

Figure 7:
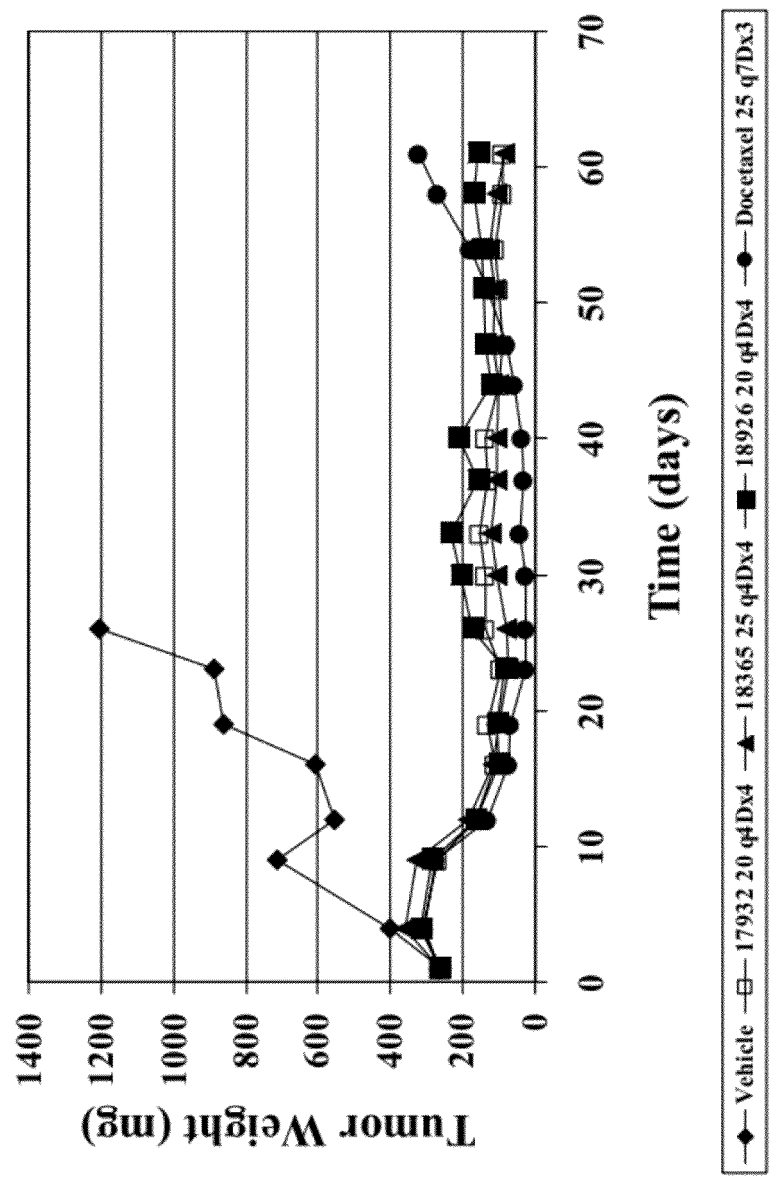
FIG. 7 depicts mean tumor growth curves for mice treated with compounds 18926, 17932, and 18365 in the HT29 study (e139) (compounds 18926, 17932, and 18365 dosed i.v. q4d×4 doses).

The mean tumor growth for this study is shown in FIG. 7.

EXAMPLE 24

In Vivo Activity of Compound 19244 in Nude Mice Bearing HT29 Human Tumor Xenografts This study was conducted at PRC. Compound 19244 was formulated in 5% ethanol and 95% Liposyn® II (5% E 95% L-II), and administered intravenously (i.v.) at 30 mg/kg, once daily every four days for four doses (q4d×4). Control mice received the 5% E 95% L-II vehicle q4d×4. A positive reference group received i.v. therapy with compound 2, at 30 mg/kg once weekly for three weeks (q7d×3), in a vehicle of 7.5% ethanol and 7.5% Tween® 80 in 5% dextrose in water. Dosing began on Day 1 in groups of six nude mice bearing upstaged (~225 mm$^3$) subcutaneous HT29 tumors. The endpoint volume for tumor growth was 1,000 mm$^3$. Compound 19244 produced 172% TGD with five 55-day survivors. Compound 19244 produced MTV of 0, but may have been administered above the maximum tolerated doses (MTDs), as there was one treatment-related (TR) death. Compound 19244 outperformed compound 2, with respect to curative activity.

TABLE 13

| | | | Regimen 1 | | | Regimen 2 | | | Max. % BW | # Death$^a$ | |
|---|---|---|---|---|---|---|---|---|---|---|---|
| Group | n | Agent | mg/kg | Route | Schedule | Day 34 | Day 41 | TTE | Loss; Day | TR | NTR |
| 1 | 6 | Vehicle | — | iv | Q4d × 4 | | | 20.1 (6) | — | 0 | 0 |
| 15 | 6 | 19244 | 30 | iv | Q4d × 4 | 17.3 | 17.3 | | −17.3%; Day 17 | 1 | 0 |
| 22 | 6 | 2 | 30 | iv | Q7d × 3 | 14.2 | 26.9 | | −16.3%; Day 20 | 0 | 0 |

Figure 8:
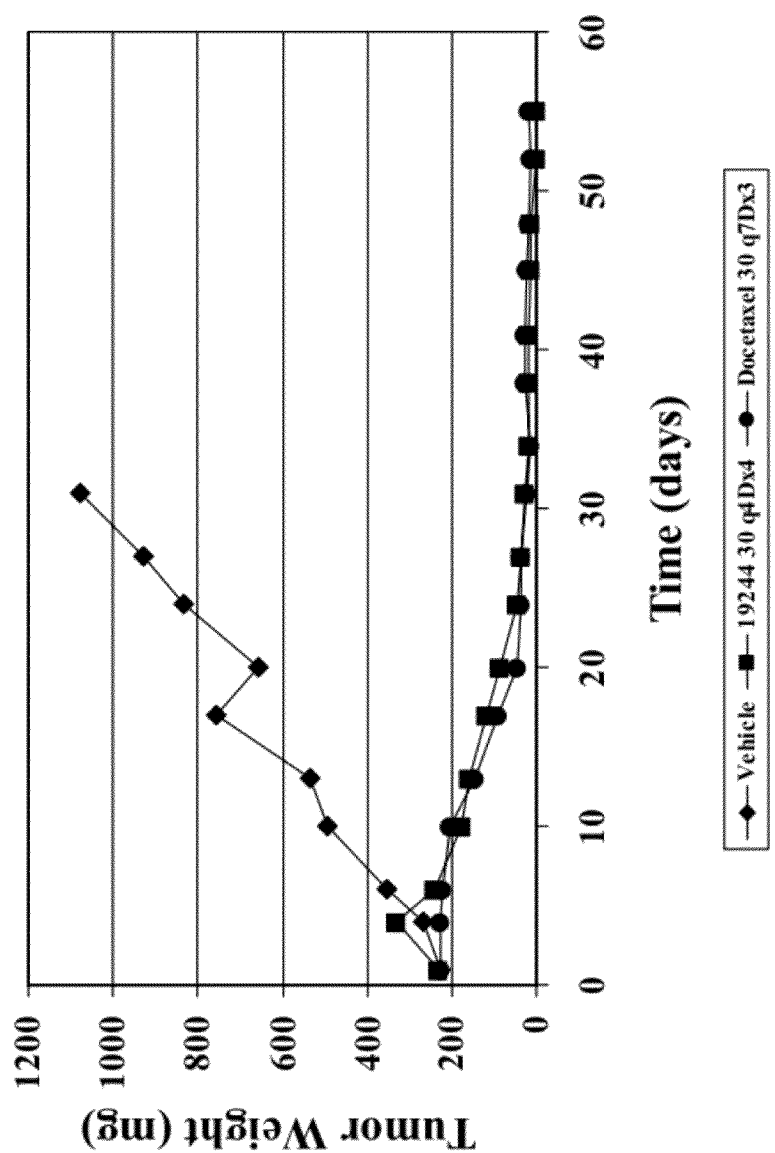
FIG. 8 depicts mean tumor growth curves for mice treated with compound 19244 in the HT29 study (e133) (compound 19244 dosed i.v. q4d×4 doses).

The mean tumor growth for this study is shown in FIG. 8.

EXAMPLE 25

In Vivo Oral and i.v. Activity of Compounds 19244 and 18365 in Nude Mice Bearing HT29 Human Tumor Xenografts This study was conducted at PRC. Compound 18365 and compound 19244 both show oral and IV activity in the HT29 xenograft tumor model on an every four day schedule for four doses. The formulation for oral studies was an ethanol and Cremophor formulation while the formulation for compound 18365 and compound 19244 dosed i.v. was 5% ethanol and 95% Liposyn II 20%. The docetaxel (compound 2) formulation was the ethanol and Tween® 80 formulation as previously described.

TABLE 14

| | | Treatment Regimen 1 | | | | | | | MTV (n), | | | | NTR | |
|---|---|---|---|---|---|---|---|---|---|---|---|---|---|---|
| Group | n | Agent | mg/kg | Route | Schedule | Median TTE | T-C | % TGD | Day 60 | PR | CR | TFS | BW Nadir | TR | NTRm | NTRa/u |
| 1$^\#$ | 6 | Vehicle | — | iv | q4d × 4 | 19.09 | | | | 0 | 0 | 0 | — | 0 | 0 |
| 7 | 6 | 18365 | 50 | po | q4d × 4 | 60 | 40.91 | 214.3 | 8.75 (6) | 2 | 4 | 3 | −7.6% (16) | 0 | 0 |
| 11 | 6 | 19244 | 60 | po | q4d × 4 | 60 | 40.91 | 214.3 | 0.25 (6) | 2 | 4 | 4 | −8.5% (16) | 0 | 0 |
| 17 | 6 | 18365 | 25 | iv | q4d × 4 | 60 | 40.91 | 214.3 | 5.00 (6) | 2 | 4 | 4 | −7.6% (16) | 0 | 0 |
| 21 | 6 | 19244 | 30 | iv | q4d × 4 | 60 | 40.91 | 214.3 | 36.00 (6) | 5 | 1 | 1 | 11.1% (16) | 0 | 0 |
| 22 | 6 | 2 | 25 | iv | qwk × 3 | 60 | 40.91 | 214.3 | 40.00 (6) | 2 | 4 | 2 | 14.3% (23) | 0 | 0 |

Figure 9:
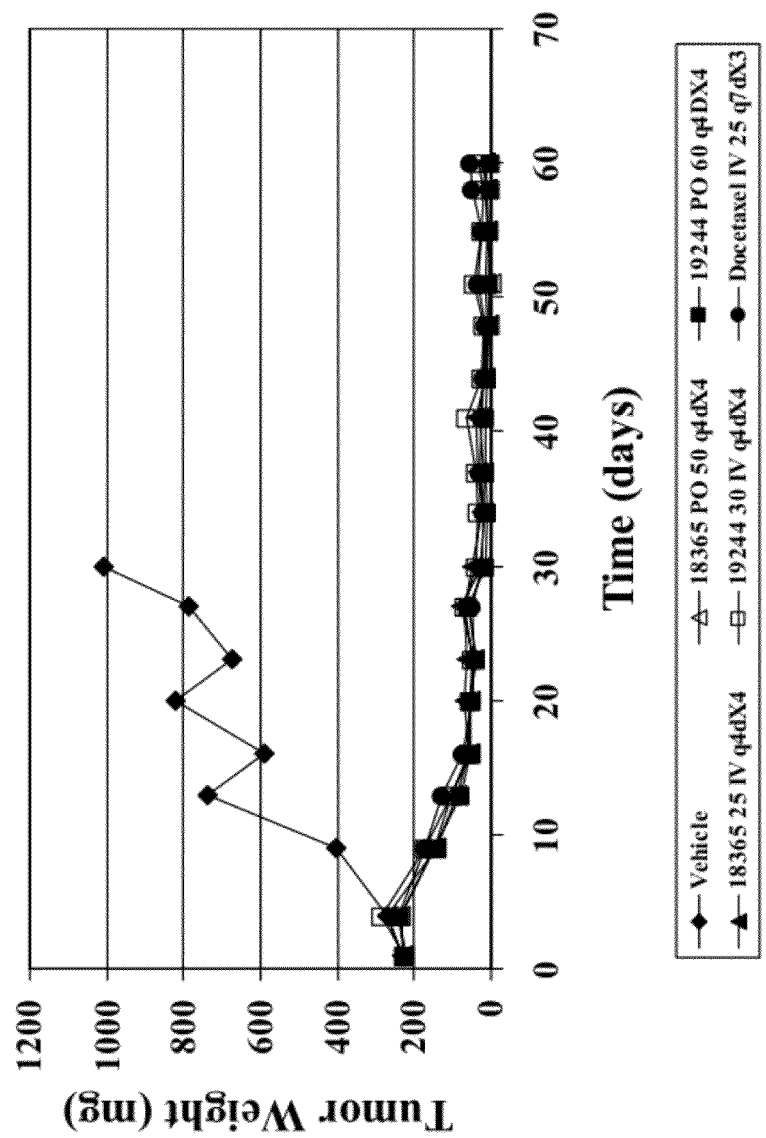
FIG. 9 depicts mean tumor growth curves for mice treated with compounds 19244 and 18365 in the HT29 study (e210) (compounds 19244 and 18365 dosed i.v. and oral q4d×4 doses).

The mean tumor growth for this study is shown in FIG. 9.

EXAMPLE 26

In Vivo Oral and Ivactivity of Compounds 19244 and 18365 in Nude Mice Bearing HT29 Human Tumor Xenografts This study was conducted at PRC. Compound 18365 and compound 19244 both showed oral and IV activity in the HT29 xenograft tumor model on an every four day schedule for four doses. The formulation for oral studies was an ethanol and Cremophor formulation while the formulation for compound 18365 and compound 19244 dosed i.v. was 5% ethanol and 95% Liposyn II 20%. The docetaxel (compound 2) formulation was the ethanol and Tween® 80 formulation as previously described.

against the human A375 melanoma xenograft. All test agents were administered i.v. at 30 mg/kg every fourth day for four doses (q4d×4), in a vehicle consisting of 5% ethanol and 95% of 20% Liposyn® II. Control mice received this vehicle i.v. on the q4d×4 regimen. The positive control group received 25 mg/kg compound 2 weekly for three weeks (qwk×3) in a vehicle consisting of 7.5% ethanol, 7.5% Tween®80 in D5W. Treatment was initiated on Day 1 in groups of six nude mice bearing established (~100 mm$^3$) s.c. A375 tumors. The endpoint was a tumor volume of 2,000 mm$^3$ and the study was terminated on Day 56. Efficacy was assessed by tumor growth delay and the number of partial and complete regressions. Animals with a CR that persisted through Day 56 were classified as long-term tumor-free survivors (TFS). Tumors in the vehicle controls all grew progressively and reached endpoint on or before Day 29 with a median of 18.1 days. The positive control, compound 2, produced a significant tumor growth delay of 8.9 days, but did not produce any regressions.

TABLE 15

| | | | | | Treatment Regimen 1 | | | | | | | | | NTR | |
|---|---|---|---|---|---|---|---|---|---|---|---|---|---|---|---|
| Group | n | Agent | Vehicle | mg/kg | Route | Schedule | Median TTE | T-C | % TGD | MTV (n), Day 59 | PR | CR | TFS | BW Nadir | TR | NTRm | NTRa/u |
| 1# | 6 | Vehicle | — | — | iv | q4d × 4 | 17.5 | | | — | 0 | 0 | 0 | — | 0 | 0 | 0 |
| 9 | 6 | 18926 | EC | 50 | po | q4d × 4 | 59 | 41.5 | 237.14 | 20.25 (6) | 5 | 1 | 1 | 10.4% (17) | 0 | 0 | 0 |
| 19 | 6 | 18926 | EL | 25 | iv | q4d × 4 | 59 | 41.5 | 237.14 | 0.00 (5) | 0 | 5 | 5 | 13.5% (17) | 1 | 0 | 0 |
| 22 | 6 | 2 | ET | 25 | iv | qwk × 3 | 59 | 41.5 | 237.14 | 600.00 (6) | 3 | 0 | 0 | −5.6% (24) | 0 | 0 | 0 |

Figure 10:
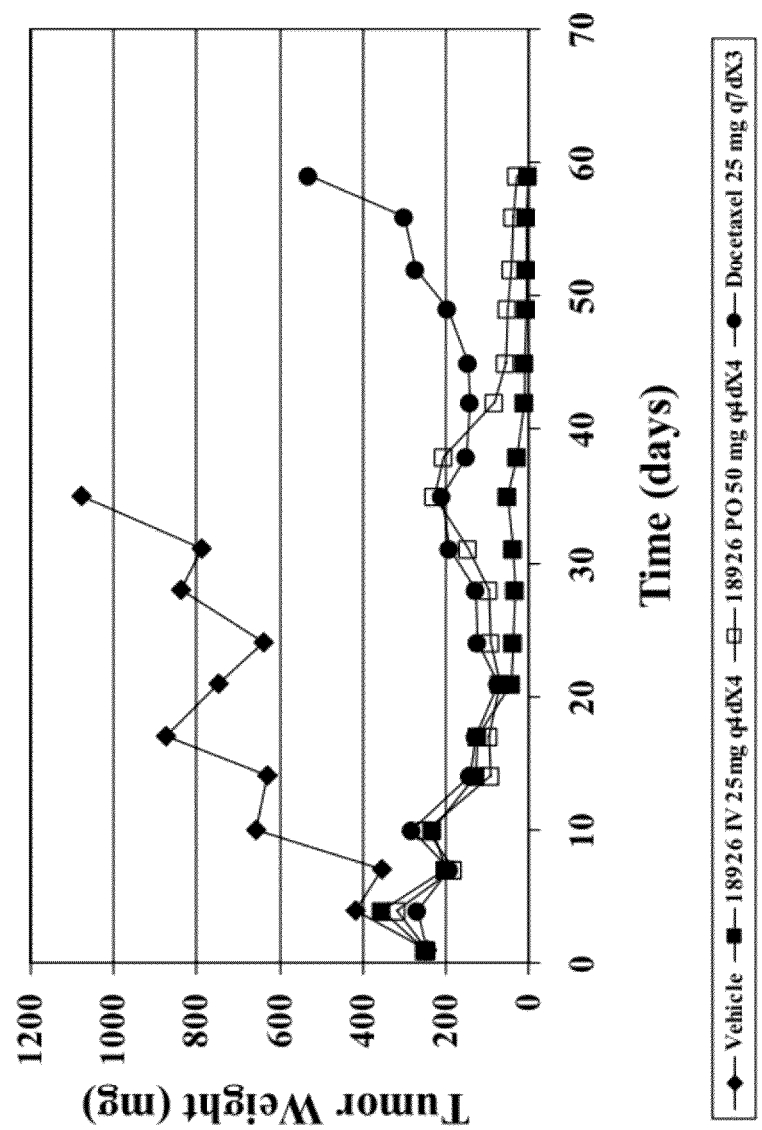
FIG. 10 depicts mean tumor growth curves for mice treated with compound 18926 in the HT29 study (e212) (18926 dosed i.v. and oral q4d×4 doses).

The mean tumor growth for this study is shown in FIG. 10.

EXAMPLE 27

In Vivo i.v. Activity of Compounds 19244, 18926, and 18365 in Nude Mice Bearing A375 Human Tumor Xenografts Compounds 18926, 18365, and 19244 were screened by Piedmont Research Center, LLC for antitumor activity At the dose level evaluated, the compounds were highly efficacious, producing regressions in the majority of treated mice.

TABLE 16

| | | | Treatment Regimen 1 | | | | | | |
|---|---|---|---|---|---|---|---|---|---|
| Group | n | Agent | Vehicle | mg/kg | Route | Schedule | Median TTE | T-C | % TGD | Stat Sign |
| 1# | 6 | Vehicle | EL | — | iv | q4d × 4 | 18.06 | | | |
| 12 | 6 | 18365 | EL | 30 | iv | q4d × 4 | 56 | 37.94 | 210.08 | |
| 15 | 6 | 18926 | EL | 30 | iv | q4d × 4 | 56 | 37.94 | 210.08 | |
| 19 | 6 | 19244 | EL | 30 | iv | q4d × 4 | 56 | 37.94 | 210.08 | |
| 22 | 6 | 2 | ET | 25 | iv | qwk × 3 | 26.92 | 8.86 | 49.06 | |

| | | | | | | | NTR | |
|---|---|---|---|---|---|---|---|---|
| Group | n | MTV(n), Day 56 | PR | CR | TFS | BW Nadir | TR | NTRm | NTRa/u |
| 1# | 6 | — | 0 | 0 | 0 | — | 0 | 0 | 0 |
| 12 | 6 | 0.00 (6) | 0 | 5 | 5 | −9.8% (14) | 0 | 0 | 0 |
| 15 | 6 | 0.00 (6) | 0 | 6 | 6 | 13.3% (18) | 0 | 0 | 0 |
| 19 | 6 | 0.00 (6) | 0 | 6 | 6 | 10.4% (18) | 0 | 0 | 0 |
| 22 | 6 | — | 0 | 0 | 0 | −4.0% (25) | 0 | 0 | 0 |

Figure 11:
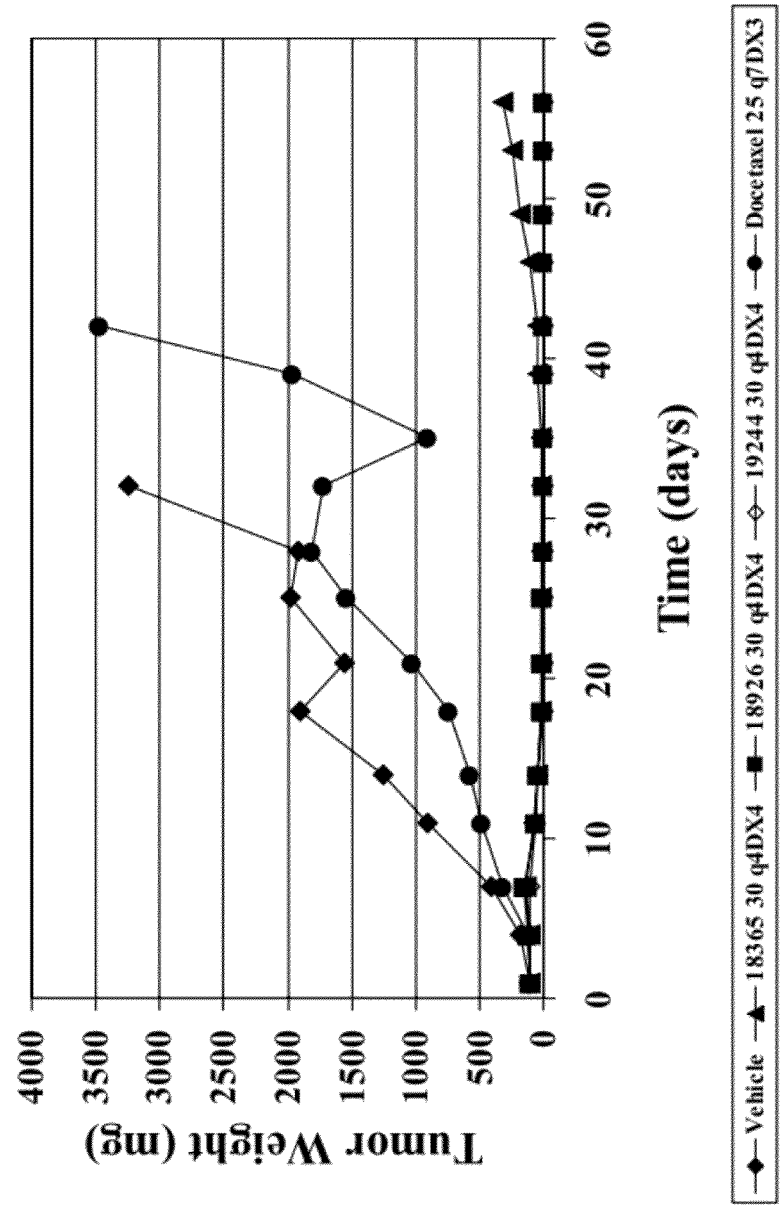
FIG. 11 depicts mean tumor growth curves for mice treated with compounds 18926, 18365, and 19244 in the A375 study (e209) (compounds 18926, 19244, and 18365 dosed i.v. q4d×4 doses).

The mean tumor growth for this study is shown in FIG. 11.

EXAMPLE 28

In Vivo i.v. Activity of Compound 18926 and Docetaxel in Nude Mice Bearing MSTO-211H Human Tumor Xenografts MSTO-211H is a resistant mesothelioma cancer cell line. Compound 18926 and docetaxel were tested by Taxolog, Inc., Tallahassee, Fla. for antitumor activity against the human MSTO-211H mesothelioma xenograft in nude mice. Compound 18926 was administered i.v. at 25 mg/kg every fourth day for four doses (q4d×4), in a vehicle consisting of 5% ethanol and 95% of 20% Liposyn® II. Control mice received this vehicle i.v. on the q4d×4 regimen. The positive control group received 25 mg/kg compound 2 weekly for three weeks (qwk×3) in a vehicle consisting of 7.5% ethanol, 7.5% Tween® 80 in D5W. Treatment was initiated on Day 1 in groups of six nude mice bearing established (~225 mm$^3$) s.c. MSTO-211H tumors. The study was terminated on Day 48. Tumors in the vehicle controls all grew progressively and reached endpoint on or before Day 20. The positive control, compound 2, did not produce any regressions. Compound 18926 was very active in this model with a tumor nadir size of 32 mg (mean) for a tumor regression of 85% over the initial tumor weight of 222 mg. Both compounds exhibited high weight loss with docetaxel showing a maximum weight loss of 31% and compound 18926 showing a weight loss of 24%

Figure 12:
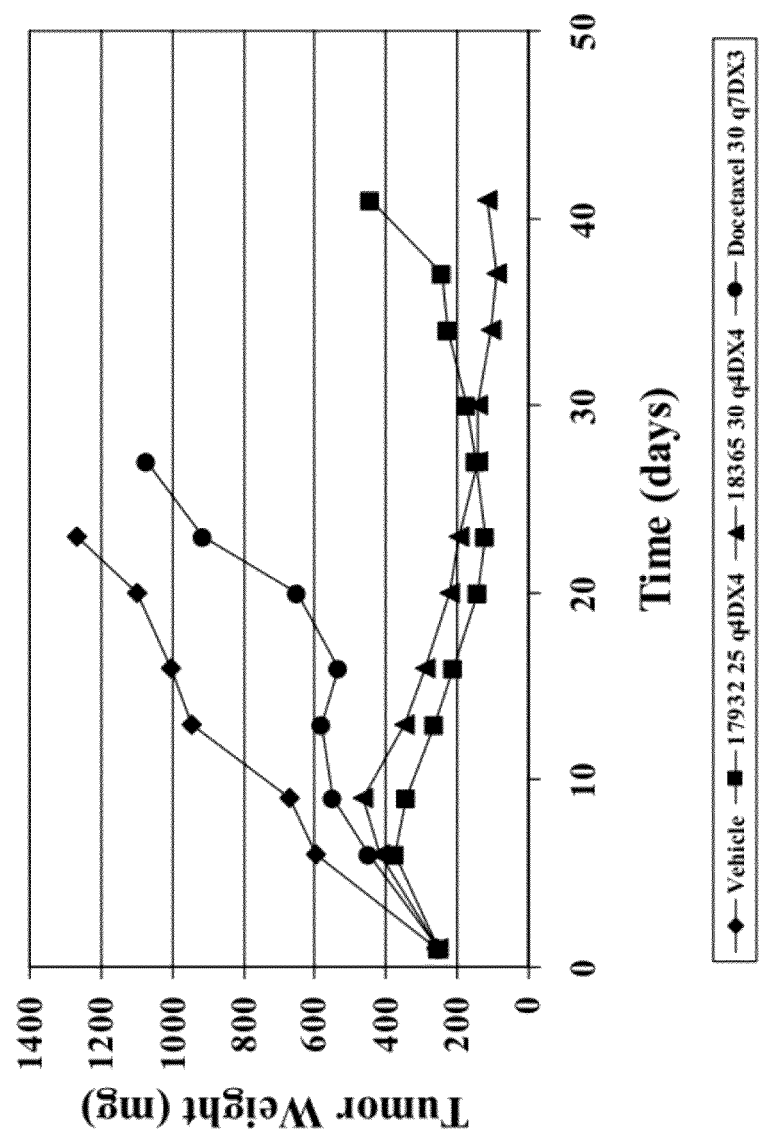
FIG. 12 depicts mean tumor growth curves for mice treated with compound 18926 in the MSTO-211H study (004) (18926 dosed i.v. q4d×4 doses).

The mean tumor growth for this study is shown in FIG. 12.

EXAMPLE 29

In Vivo i.v. Activity of Compound 19244 and Docetaxel in Nude Mice Bearing MSTO-211H Human Tumor Xenografts Compound 19244 and docetaxel were tested by Taxolog, Inc., Tallahassee, Fla. for antitumor activity against the human MSTO-211H mesothelioma xenograft in nude mice. Compound 19244 was administered i.v. at 30 mg/kg every fourth day for four doses (q4d×4), in a vehicle consisting of 5% ethanol and 95% of 20% Liposyn® II. Control mice received this vehicle i.v. on the q4d×4 regimen. The positive control group received 25 mg/kg compound 2 weekly for three weeks (qwk×3) in a vehicle consisting of 7.5% ethanol, 7.5% Tween®80 in D5W. Treatment was initiated on Day 1 in groups of six nude mice bearing established (~220 mm$^3$) s.c. MSTO-211H tumors. The study was terminated on Day 48. Tumors in the vehicle controls all grew progressively and reached endpoint on or before Day 30. The positive control, compound 2 did not produce any regressions. Compound 19244 was very active in this model with a tumor nadir size of 51 mg (mean) for a tumor regression of 77% over the initial tumor weight of 220 mg. Both compounds exhibited high weight loss with docetaxel showing a maximum weight loss of 24% and compound 19244 showing a weight loss of 21%.

Figure 13:
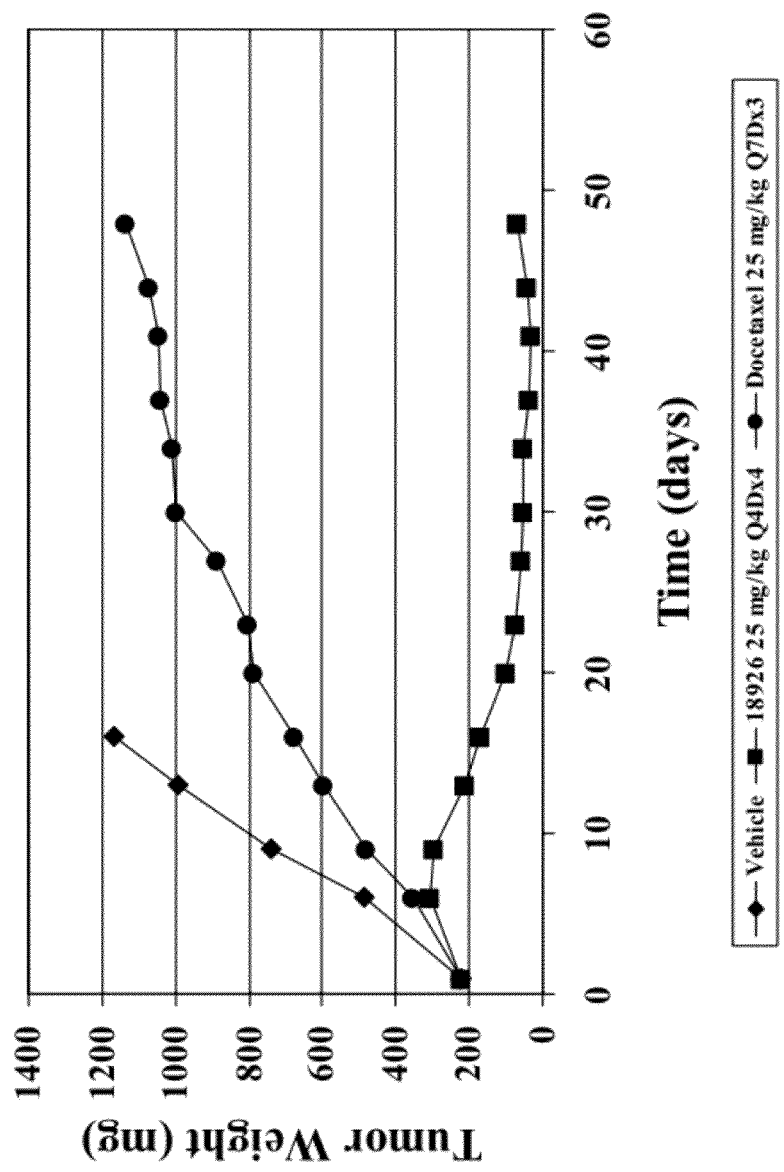
FIG. 13 depicts mean tumor growth curves for mice treated with compound 19244 in the MSTO-211H study (008) (19244 dosed i.v. q4d×4 doses).

The mean tumor growth for this study is shown in FIG. 13.

EXAMPLE 30

In Vivo i.v. Activity of Compounds 18926 and 18365 in Nude Mice Bearing MSTO-211H Human Tumor Xenografts Compounds 18365 and 18926 were tested by Taxolog, Inc., Tallahassee, Fla. for antitumor activity against the human MSTO-211H mesothelioma xenograft in nude mice. Compound 18926 was administered i.v. at 20 mg/kg and compound 18365 was administered a dose of 25 mg/kg i.v. every fourth day for four doses (q4d×4), in a vehicle consisting of 10% ethanol, 10% Cremophor EL® and 80% of D5W. Control mice received this vehicle i.v. on the q4d×4 regimen. The positive control group received 25 mg/kg compound 2 weekly for three weeks (qwk×3) in a vehicle consisting of 7.5% ethanol, 7.5% Tween®80 in D5W. Treatment was initiated on Day 1 in groups of five nude mice bearing established (~220 mm$^3$) s.c. MSTO-211H tumors. The study is ongoing and not yet terminated. Compounds 18926 and 18365 are both very active in this study with both compounds showing significant regression. Both compounds exhibited weight loss with compound 18926 showing a maximum weight loss of 16% and compound 18365 showing a weight loss of 18% and also 1 TR.

Figure 14:
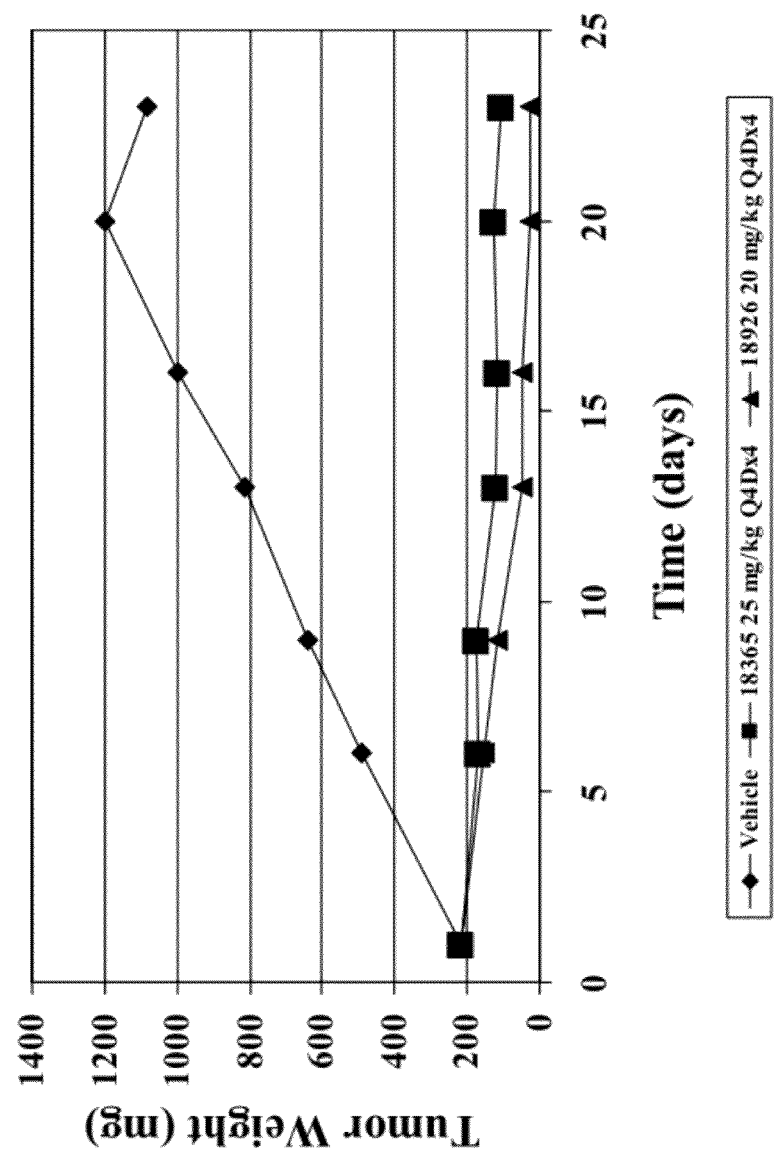
FIG. 14 depicts mean tumor growth curves for mice treated with compounds 18926 and 18365 in the MSTO-211H study (101) (compounds 18926 and 18365 dosed i.v. q4d×4 doses).

The mean tumor growth for this study is shown in FIG. 14.

EXAMPLE 31

In Vivo i.v. Activity of Compounds 18926 and 18365 and Other Anti-Cancer Compounds in Nude Mice Bearing MSTO-211H Human Tumor Xenografts Compounds 18365 and 18926 along with other anti-cancer compounds were tested by Taxolog, Inc., Tallahassee, Fla. for antitumor activity against the human MSTO-211H mesothelioma xenograft in nude mice according to the following protocol.

TABLE 17

| Group Number | N | Compound | Vehicle | mg/kg | Route | Schedule |
| --- | --- | --- | --- | --- | --- | --- |
| 1 | 5 | Vehicle | 10% E, 10% C, 80% D5W | 0 | IV | Q4D × 4 |
| 3 | 5 | Docetaxel | 7.5% E, 7.5% Tw80, 85% D5W | 25 | IV | Q7D × 3 |
| 4 | 5 | Paclitaxel | 5% E, 5% C, 90% D5W | 30 | IV | Q2D × 5 |
| 5 | 5 | Irinotecan | NaCl | 60 | IP | Q4D × 3 |
| 6 | 5 | Gemcitabine | NaCl | 30 | IP | Q3D × 3 |
| 7 | 5 | Pemetrexed | NaCl | 300 | IP | QD × 10 |
| 8 | 5 | Carboplatin | NaCl | 15 | IP | Q4D × 3 |
| 9 | 5 | Doxorubicin | NaCl | 5 | IV | Q7D × 3 |
| 10 | 5 | Vincristine | NaCl | 1 | IP | Q4D × 3 |
| 11 | 5 | 18365 | 10% E, 10% C, 80% D5W | 30 | IV | Q4D × 4 |
| 12 | 5 | 18926 | 10% E, 10% C, 80% D5W | 30 | IV | Q4D × 4 |

Treatment was initiated on Day 1 in groups of five nude mice bearing established (~185 mm³) s.c. MSTO-211H tumors. Compound 18365 was very active in this study with tumor regressions. Compound 18926 was toxic at this dose in this study.

Figure 15:
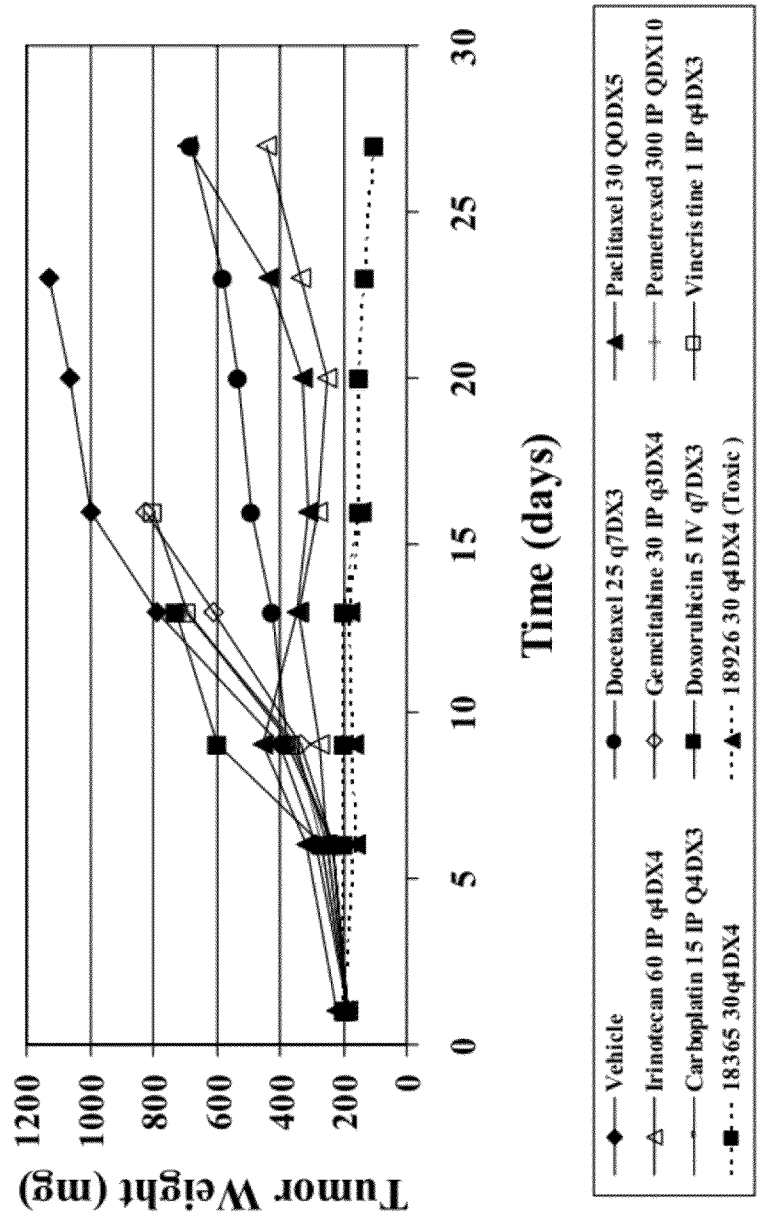
FIG. 15 depicts mean tumor growth curves for mice treated with compounds 18926, 18365, and various anticancer compounds in the MSTO-211H study (091) (compounds 18926 and 18365 dosed i.v. q4d×4 doses).

The mean tumor growth for this study is shown in FIG. 15.

EXAMPLE 32

In Vivo i.v. Activity of Compounds 18365, 19244, and Docetaxel in Nude Rats Bearing BxPC-3 Human Pancreatic Tumor Xenografts Compounds 18365 and 19244 were tested by Oncodesign, France for antitumor activity against the human BxPC-3 human pancreatic xenograft model in nude rats.

Method: Twenty four (24) hours after a whole body irradiation with a γ-source (7.0 Gy, $Co^{60}$, INRA, Dijon, France) $20 \times 10^6$ BxPC-3 cells in 200 μl of RPMI 1640 culture medium were subcutaneously injected in the right flank of 8 female Nude rats to generate tumor material. When the tumor size reaches approximately 1,000 mm³, the tumors were surgically excised for implantation into recipient Nude female rats. Twenty four (24) hours after a whole body irradiation (7.0 Gy, $Co^{60}$, INRA, Dijon, France), fresh BxPC-3 tumor fragments were sc implanted in the right flank of 52 Nude female rats (1 fragment/rat) at D0 using surgical pliers and skin was stitched. The antitumor activity study was started at D21 when the mean tumor volume has reached 321.6±131.2 mm³. Before the start of treatments, 42 tumor bearing rats out of 52 grafted were randomized into 7 groups of 6 animals. The mean tumor volume of each group was comparable and not statistically different from the other groups (analysis of variance).

The treatment schedule is summarized in the table below:

TABLE 18

| Group | Number of rats | Treatment | dose (mg/kg/adm) | Adm route | Treatment Day* |
|---|---|---|---|---|---|
| 1 | 6 | Vehicle | — | IV | D21, D28, D42 and D49 |
| 2 |  | 18365 | 5 |  | D21, D28, D42 and D49 |
| 3 |  |  | 7 |  | D21 and D42 |
| 4 |  | 19244 | 5 |  | D21, D42 and D49 |
| 5 |  |  | 7 |  | D21 and D42 |
| 6 |  | TXT | 5 |  | D21, D28, D42 and D49 |
| 7 |  |  | 7 |  | D21 and D42 |

As severe body weight loss was observed with no recovery between each treatment, the original Q7Dx4 treatment schedule was adjusted to compound and dose. At 5 mg/kg/inj, 4 treatments were administered at D21, D28, D42 and D49 for compound 18365 and TXT as for compound 19244 3 injections only were done at D21, D42 and D49 due to slower body weight recovery. At 7 mg/kg/inj, only two treatments were performed at D21 and D42 due to severe body weight loss.

Compound 18365

The mean doubling time (DT) of tumors from rats of vehicle treated group was 10.9±6.0 days. The mean doubling time of tumors from rats treated with compound 18365 at 5 mg/kg/inj were increased to 24.7±10.4 days but not significantly different when compared to vehicle group. When treated at 7 mg/kg/inj, no DT analysis was made since only one animal was available for DT evaluation. The time to reach volume (T to V) of 1,000 mm³ for vehicle treated rats was 30.0±2.7 days. The T to V of 1,000 mm³ for compound 18365 at 5 mg/kg/inj treated group was statistically significantly increased (64.3±16.3 days) when compared to the vehicle treated group (p=0.0007). When treated at 7 mg/kg/inj, no sufficient number of animals (only one) was available to conclude.

Compound 18365 at 5 mg/kg/inj induced optimal T/C % value of 11.0% at D53 (n=5). The T/C % values were lower than 42% from D33. At D81 (final sacrifice), two animals were recorded with complete tumor regression in this group. Compound 18365 at 7 mg/kg/inj induced optimal T/C % value of 13.2% at D53 (n=3). The T/C % values were lower than 42% from D33. A marked antitumor activity of compound 18365 was evidenced in the model of Nude rats bearing subcutaneous BxPC-3 tumor when treated by repeated IV injections at 5 and 7 mg/kg/inj, a total of four treatments (at D21, D28, D42 and D49) and two treatments (at D21 and D42) being administrated, respectively. At the 5 mg/kg/inj, the repeated IV treatments with compound 18365 were not well tolerated by Nude rats bearing subcutaneous BxPC-3 tumor. A severe body weight loss was observed, reaching −16.9±6.1% at D33 (close to the significant threshold) and leading to delay the day of treatment. The schedule Q7Dx4 was changed to treatments at D21, D28, D42 and D49. Only one rat (ID 3171) was sacrificed at D35 due to no body weight recovery.

At 7 mg/kg/inj, the repeated IV treatments with compound 18365 were not tolerated by Nude rats bearing subcutaneous BxPC-3 tumor. After the first treatment, a severe and statistically significant body weight loss was observed (MBWC D21-D26 of −16.5±7.2 and −2.0±4.8% for the compound 18365 at 7 mg/kg/inj and the vehicle treated groups respectively, p<0.0001). The body weight loss and time to recover body weight led to reduce the number of treatments. The schedule Q7Dx4 was changed to only two treatments at D21 and D42. The second treatment led also to a severe body weight loss and body weight recover was only observed for one animal. Three rats were found dead (at D23, D27 and D49) and two were sacrificed (at D53 and D70). Only one rat out of six treated with compound 18365 at 7 mg/kg/inj was alive at the end of the study.

Compound 19244

At 5 mg/kg/inj, the repeated IV treatments with compound 19244 were well tolerated by Nude rats bearing subcutaneous BxPC-3 tumor. After the first injection, a severe and statistically significant body weight loss was observed (MBWC D21-D26 of −15.9±5.6 and −2.0±4.8% for the compound 19244 at 5 mg/kg/inj and the vehicle treated groups respectively, p<0.0001). The loss of body weight led to reduce the number of treatments and delay the day of treatments. The schedule Q7Dx4 was changed to treatments at D21, D42 and D49. Three rats were found dead (at D34, D49 and D55) when treated with compound 19244 at 5 mg/kg/inj. At 7 mg/kg/inj, the repeated IV treatments with compound 19244 were not tolerated by Nude rats bearing subcutaneous BxPC-3 tumor. After the first treatment, a severe and statistically significant body weight loss was observed (MBWC D21-D26 of −20.1±5.7 and −2.0±4.8% for the compound 19244 at 7 mg/kg/inj and the vehicle treated groups respectively, p<0.0001). The body weight loss and time to recover body weight led to reduce the number of treatments. The schedule Q7Dx4 was changed to only two treatments at D21 and D42. Three rats were found dead (at D27, D28 and D31) and one was sacrificed at D49. Only two rats out of six treated with compound 19244 at 7 mg/kg/inj were alive at the end of the study.

The mean doubling time of tumors from rats treated with compound 19244 at 5 mg/kg/inj were increased to 19.3±6.5 days but the difference was not statistically significant when compared to vehicle group (DT of 10.9±6.0 days). When treated at 7 mg/kg/inj, no sufficient number of animals (only one) was available to conclude.

The T to V of 1,000 mm$^3$ for compound 19244 at 5 mg/kg/inj treated group was increased (46.0±11.6 days) when compared to the vehicle treated group but the difference was not statistically significant (p=0.0240). When treated at 7 mg/kg/inj, no sufficient number of animals (only one) was available to conclude.

Compound 19244 at 5 mg/kg/inj induced optimal T/C % value of 27.7% at D53 (n=4). The T/C % values were lower than 42% from D33. Compound 18365 at 7 mg/kg/inj induced optimal T/C % value of 8.9% at D53 (n=2). The T/C % values were lower than 42% from D33.

A marked antitumor activity of compound 19244 was evidenced in the model of Nude rats bearing subcutaneous BxPC-3 tumor when treated by repeated IV injections at 5 and 7 mg/kg/inj, a total of three treatments (at D21, D42 and D49) and two treatments (at D21 and D42) being administered, respectively.

TXT

At 5 mg/kg/inj, the repeated IV treatments with TXT were not well tolerated by Nude rats bearing subcutaneous BxPC-3 tumor. A severe body weight loss was observed, reaching −15.4±8.2% at D33 (close to the significant threshold) and leading to delay the day of treatment. The schedule Q7D×4 was changed to treatments at D21, D28, D42 and D49. One rat was sacrificed at D35 and two were found dead at D58.

At 7 mg/kg/inj, the repeated IV treatments with TXT were not tolerated by Nude rats bearing subcutaneous BxPC-3 tumor. After the first treatment, a severe and statistically significant body weight loss was observed (MBWC D21-D26 of −16.3±7.0 and −2.0±4.8% for the TXT at 7 mg/kg/inj and the vehicle treated groups respectively, p<0.0001). The body weight loss and time to recover body weight led to reduce the number of treatments. The schedule Q7D×4 was changed to only two treatments at D21 and D42. Two rats were found dead (at D28 and D29) and two were sacrificed (at D60 and D70). Only two rats out of six treated with TXT at 7 mg/kg/inj were alive at the end of the study.

The mean doubling time of tumors from rats treated with TXT at 5 mg/kg/inj could not be calculated as no animal was available for DT evaluation. When treated at 7 mg/kg/inj, no sufficient number of animals (only two) was available to conclude.

The T to V of 1,000 mm$^3$ for TXT at 5 or 7 mg/kg/inj treated group was increased when compared to the vehicle treated group but only one or two animals are available for evaluation.

TXT at 5 mg/kg/inj induced optimal T/C % value of 3.8% at D60 (n=2). The T/C % values were lower than 42% from D33. At D81 (final sacrifice), one animal was recorded with complete tumor regression in this group. TXT at 7 mg/kg/inj induced optimal T/C % value of 12.3% at D56. The T/C % values were lower than 42% from D33.

A marked antitumor activity of TXT was evidenced in the model of Nude rats bearing subcutaneous BxPC-3 tumor when treated by repeated IV injections at 5 and 7 mg/kg/inj, a total of four treatments (at D21, D28, D42 and D49) and two treatments (at D21 and D42) being administered, respectively Summary of results from rat xenograft study Toxicity Rat xenograft Study

18365

5 mg/kg 16.9% wt loss, 1 sacrificed weight loss 7 mg/kg 3 found dead, 2 sacrificed weight loss

19244

5 mg/kg 3 found dead 7 mg/kg 3 found dead, 1 sacrificed

Docetaxel 5 mg/kg 2 found dead 1 sacrificed 7 mg/kg 2 found dead 2 sacrificed

Figure 16:
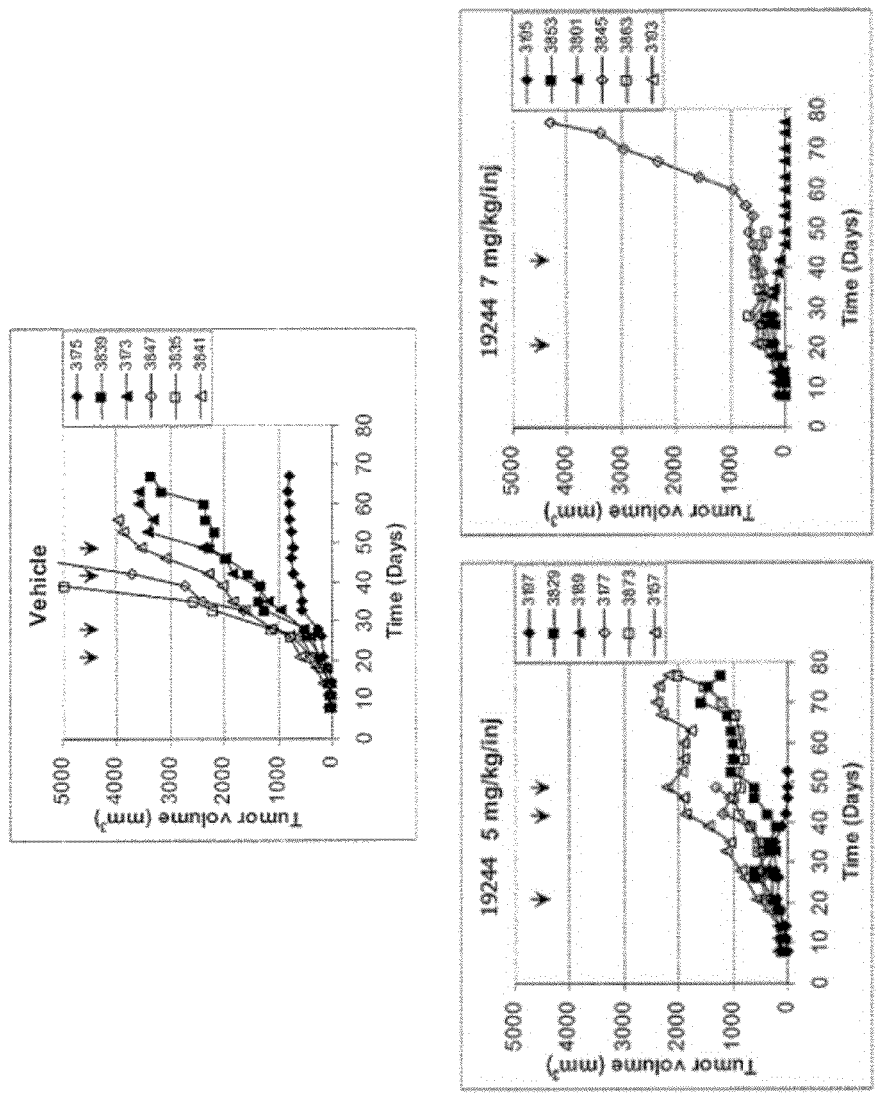
FIG. 16 depicts mean tumor growth curves for rats treated with vehicle and compound 19244 in the BxPC-3 study.
Figure 17:
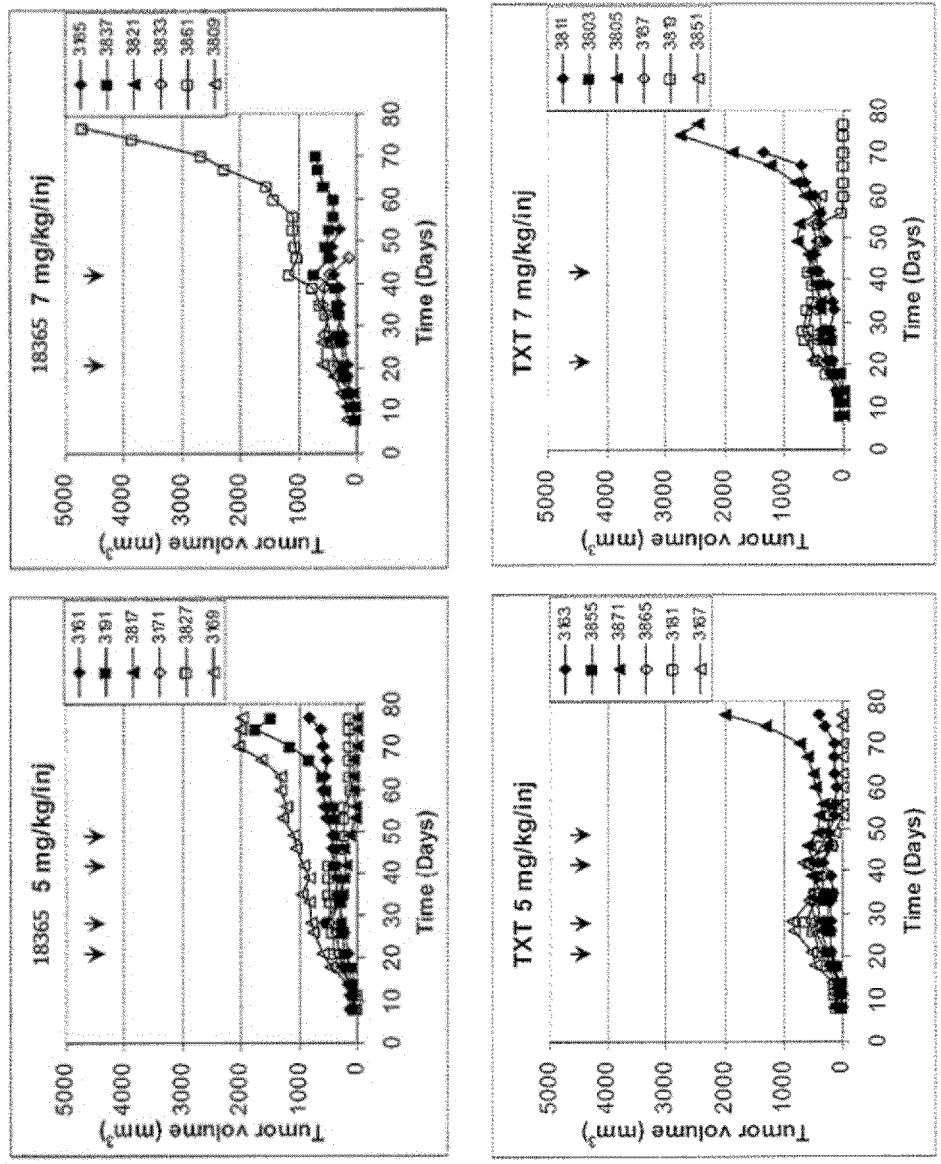
FIG. 17 depicts mean tumor growth curves for rats treated with docetaxel and compound 18365 in the BxPC-3 study.

In conclusion, the xenograft study showed that when compound 18365 was dosed on the same schedule and dose as docetaxel it was less toxic and better tolerated in nude rats. FIG. 15 shows the tumor growth for the vehicle control and the compound 19244 groups. FIG. 16 shows the tumor growth for the compound 18365 and the docetaxel group.

EXAMPLE 33

In Vivo Toxicity Assessmentin Rats

Toxicity was assessed in 250-300 g Sprague-Dawley rats and three rats were used per dose group using a dose of 12 mg/kg for intravenous administration. Animals were observed and clinical chemistry data collected at days 4 and 10. Rats were euthanized on day 11 and the nerves were excised and fixed upon euthanization for further examination.

Each rat is scored as described below and a final toxicity score that incorporates all parameters is assigned. A dead rat is assigned a score of zero. Table 18 below gives the criteria for how each toxicity parameter contributes to the score. Most of the parameters contribute a positive value towards a total possible score of 130. For body weight, white blood cell, and platelet decreases, recovery is considered. If the parameter does not show recovery, then a −5 is subtracted from the total. The total score is divided by 13 to put it on a scale from 0 to 10. As for the neurotoxicity score, a −10 indicates that axonal degeneration lesions were seen, while a 0 indicates there were no lesions. The same technique was used to measure toxicity in studies using a dosing regimen of weekly for three weeks where the clinical chemistry was taken 4 days after the last dose.

The axonal degeneration was also measured quantitatively to estimate the number of axons degenerated for a uniform surface area.

TABLE 19

| Score | Axonal degeneration |
|---|---|
| 0 | no degen axons |
| 1 | 1-3 degen axons |
| 2 | 4-10 degen axons |
| 3 | 11-50 degen axons |
| 4 | 50+ degen axons |

TABLE 20

Criteria for Rat Toxicity Scoring

| Observation | Score | | | | Recovery Week 2 | |
|---|---|---|---|---|---|---|
| Neurotoxicity | N (0) | Y (1-4) | | | N | Y |
| | 0 | −10 | | | | |
| Body Weight Loss | ≧20% | ≧15% | ≧10% | <10% | | |
| | 0 | 5 | 10 | 20 | −5 | 0 |
| WBC decrease | ≧50% | ≧25% | ≧10% | <10% | | |
| | 0 | 5 | 10 | 20 | −5 | 0 |
| Platelets decrease | ≧75% | ≧50% | ≧25% | <25% | | |
| | 0 | 5 | 10 | 20 | −5 | 0 |
| AST elevation | ≧2 × cont. | ≧1.5 × cont | ≧1.25 × cont | <1.25 × cont | | |
| | 0 | 5 | 10 | 20 | | |
| ALT elevation | ≧2 × cont | ≧1.5 × cont | ≧1.25 × cont | <1.25 × cont | | |
| | 0 | 5 | 10 | 20 | | |
| BUN elevation | ≧2 × cont | ≧1.5 × cont | ≧1.25 × cont | <1.25 × cont | | |
| | 0 | 5 | 10 | 20 | | |
| Water/Loose Diarrhea | N | Y | | | | |
| | 5 | 0 | | | | |
| Bloody/Mucoid Diarrhea | N | Y | | | | |
| | 5 | 0 | | | | |

Maximum score (each rat) = 130;
Group score = average of 3 rats/13;
Avg = average of 3 groups
cont = control
AST = Aspartate aminotransferase (AST);
Wt Avg = (Σ(dose × grp score))/24
ALT = Alanine aminotransferase
BUN = Blood urine nitrogen
WBC = White blood cell
PTL = Platelet;

In the rat toxicity study e206, compound 19244 had a score of 7.7 with docetaxel as a control showing a score of 5.9. The dose of 12 mg/kg is equivalent to 72 mg/m$^2$ which is similar to the human dose of docetaxel when dosed every three weeks. Not only does compound 19244 have a similar score to docetaxel in this study but the axonal degeneration was less than the docetaxel control. This could indicate a potential benefit in the clinic of a lowered risk of peripheral neuropathy. There was no mortality in the study. Compound 19244 was formulated in an ethanol and Liposyn II 20% formulation and docetaxel was formulated in an ethanol and Tween® 80 based formulation as previously described.

TABLE 21

Results from e206 study

| IV Dose/Rat | Mort | Neuro Tox | Day 1 BW | Day 8 BW | Day 10 BW | Day 4 WBC | Day 10 WBC | Day 4 PLT | Day 10 PLT | Day 4 ALT | Day 4 AST | Day 4 BUN | Dia L/W | Dia B/M | Total | Score |
|---|---|---|---|---|---|---|---|---|---|---|---|---|---|---|---|---|
| 19244 12 mg/kg | | | | | | | | | | | | | | | | |
| Rat 1 | | 0 | 231 | 219 | 227 | 3.87 | 16.4 | 1220 | 994 | 26 | 204 | 18 | n | n | | |
| | | 0 | | 20 | 0 | 0 | 0 | 20 | 0 | 20 | 10 | 20 | 5 | 5 | 100 | 7.7 |
| Rat 2 | | 0 | 230 | 197 | 203 | 3.52 | 15 | 1005 | 1137 | 19 | 158 | 12 | n | n | | |
| | | 0 | | 10 | 0 | 0 | 0 | 20 | 0 | 20 | 20 | 20 | 5 | 5 | 100 | 7.7 |
| Rat 3 | | 0 | 227 | 208 | 221 | 4.92 | 11.7 | 792 | 1370 | 28 | 119 | 12 | n | n | | |
| | | 0 | | 20 | 0 | 0 | 0 | 10 | 0 | 20 | 20 | 20 | 5 | 5 | 100 | 7.7 |
| | | | | | | | | | | | | | | | AVE | 7.7 |

| IV | Neuro | Day 1 | Day 8 | Day 10 | Day 4 | Day 10 | Day 4 | Day 10 | Day 4 | Day 4 | Day 4 | Dia | Dia | | |
|---|---|---|---|---|---|---|---|---|---|---|---|---|---|---|---|
| Docetaxel 12 mg/kg | | | | | | | | | | | | | | | |
| Rat 1 | 4 | 242 | 217 | 221 | 3.96 | 11 | 835 | 1540 | 32 | 179 | 15 | n | n | | |
| | −10 | | 10 | 0 | 0 | 0 | 10 | 0 | 20 | 10 | 20 | 5 | 5 | 70 | 5.4 |
| Rat 2 | 4 | 215 | 200 | 208 | 2.34 | 10.1 | 768 | 1550 | 39 | 230 | 8 | n | n | | |
| | −10 | | 20 | 0 | 0 | 0 | 10 | 0 | 20 | 5 | 20 | 5 | 5 | 75 | 5.8 |
| Rat 3 | 3 | 240 | 220 | 233 | 5.45 | 11.7 | 1000 | 1478 | 31 | 264 | 13 | n | n | | |
| | −10 | | 20 | 0 | 0 | 0 | 20 | 0 | 20 | 5 | 20 | 5 | 5 | 85 | 6.5 |
| | | | | | | | | | | | | | | AVE | 5.9 |

In the rat toxicity study e195, compound 17932 had a score of 8.1 (average of 7.3, 7.7, and 9.2) which is lower than the docetaxel historical control. Compound 17932 also showed very little axonal degeneration. Compound 17932 was formulated in an ethanol and Liposyn II 20% formulation.

TABLE 22

Results from e195 study

| IV Dose/Rat | Mortality | Neuro Tox | Day 1 BW | Day 8 BW | Day 10 BW | Day 4 WBC | Day 10 WBC | Day 4 PLT | Day 10 PLT | Day 4 ALT | Day 4 AST | Day 4 BUN | Dia L/W | Dia B/M | Total | Score |
|---|---|---|---|---|---|---|---|---|---|---|---|---|---|---|---|---|
| 17932 12 mg/kg | | | | | | | | | | | | | | | | |
| Rat 1 | 1 | | 234 | 211 | 226 | 5.47 | 11.2 | 742 | 957 | 27 | 121 | 15 | n | n | | |
|  | −10 | | | 20 | 0 | 5 | 0 | 10 | 0 | 20 | 20 | 20 | 5 | 5 | 95 | 7.3 |
| Rat 2 | 0 | | 231 | 205 | 210 | 7.92 | 14.6 | 836 | 1207 | 20 | 100 | 9 | n | n | | |
|  | 0 | | | 10 | 0 | 10 | 0 | 10 | 0 | 20 | 20 | 20 | 5 | 5 | 100 | 7.7 |
| Rat 3 | 0 | | 230 | 211 | 211 | 9.24 | 25.3 | 854 | 1506 | 24 | 111 | 9 | n | n | | |
|  | 0 | | | 20 | 0 | 20 | 0 | 10 | 0 | 20 | 20 | 20 | 5 | 5 | 120 | 9.2 |

In the rat toxicity study e196, compound 18365 had a score of 7.7 which is lower than the docetaxel historical control. Compound 18365 also showed no axonal degeneration. Compound 18365 was formulated in an ethanol and Liposyn II 20% formulation.

TABLE 23

Results from e196 study

| IV Dose/Rat | Mortality | Neuro Tox | Day 1 BW | Day 8 BW | Day 10 BW | Day 4 WBC | Day 10 WBC | Day 4 PLT | Day 10 PLT | Day 4 ALT | Day 4 AST | Day 4 BUN | Dia L/W | Dia B/M | Total | Score |
|---|---|---|---|---|---|---|---|---|---|---|---|---|---|---|---|---|
| 18365 12 mg/kg | | | | | | | | | | | | | | | | |
| Rat 1 | 0 | | 239 | 225 | 241 | 5.62 | 12.1 | 1106 | 1214 | 20 | 98 | 15 | n | n | | |
|  | 0 | | | 20 | 0 | 5 | 0 | 20 | 0 | 20 | 10 | 20 | 5 | 5 | 105 | 8.1 |
| Rat 2 | 0 | | 222 | 203 | 211 | 5.65 | 10.2 | 968 | 1201 | 19 | 101 | 18 | n | n | | |
|  | 0 | | | 20 | 0 | 5 | 0 | 10 | 0 | 20 | 10 | 10 | 5 | 5 | 85 | 6.5 |
| Rat 3 | 0 | | 229 | 213 | 225 | 3.39 | 13.4 | 1035 | 1080 | 20 | 81 | 15 | n | n | | |
|  | 0 | | | 20 | 0 | 0 | 0 | 20 | 0 | 20 | 20 | 20 | 5 | 5 | 110 | 8.5 |
|  | | | | | | | | | | | | | | | AVE | 7.7 |

In the rat toxicity study e199, compound 18926 had a score of 7.4 with docetaxel as a control showing a score of 6.4. Not only does compound 18926 have a similar score to docetaxel in this study but compound 18926 showed no axonal degeneration. This could indicate a potential benefit in the clinic of a lowered risk of peripheral neuropathy. There was no mortality in the study. Compound 18926 was formulated in an ethanol and Liposyn II 20% formulation and docetaxel was formulated in an ethanol and Tween® 80 based formulation as previously described.

TABLE 24

Results from e199 study

| IV Dose/Rat | Mort | Neuro Tox | Day 1 BW | Day 8 BW | Day 10 BW | Day 4 WBC | Day 10 WBC | Day 4 PLT | Day 10 PLT | Day 4 ALT | Day 4 AST | Day 4 BUN | Dia L/W | Dia B/M | Total | Score |
|---|---|---|---|---|---|---|---|---|---|---|---|---|---|---|---|---|
| 18926 12 mg/kg | | | | | | | | | | | | | | | | |
| Rat 1 | 0 | | 219 | 200 | 204 | 5.06 | 12.8 | 829 | 1319 | 26 | 33 | 9 | n | n | | |
|  | 0 | | | 20 | 0 | 0 | 0 | 10 | 0 | 20 | 20 | 20 | 5 | 5 | 100 | 7.7 |
| Rat 2 | 0 | | 241 | 213 | 223 | 5.79 | 11.8 | 960 | 1547 | 31 | 129 | 9 | n | n | | |
|  | 0 | | | 10 | 0 | 5 | 0 | 20 | 0 | 20 | 5 | 20 | 5 | 5 | 90 | 6.9 |
| Rat 3 | 0 | | 231 | 206 | 208 | 4.86 | 11.6 | 948 | 1442 | 32 | 26 | 12 | n | n | | |
|  | 0 | | | 10 | 0 | 0 | 0 | 20 | 0 | 20 | 20 | 20 | 5 | 5 | 100 | 7.7 |
|  | | | | | | | | | | | | | | | AVE | 7.4 |

TABLE 24-continued

Results from e199 study

| IV | Neuro | Day 1 | Day 8 | Day 10 | Day 4 | Day 10 | Day 4 | Day 10 | Day 4 | Day 4 | Day 4 | Dia | Dia | Total | Score |
|---|---|---|---|---|---|---|---|---|---|---|---|---|---|---|---|
| Docetaxel 12 mg/kg | | | | | | | | | | | | | | | |
| Rat 1 | 3 | 228 | 225 | 229 | 4.89 | 19 | 922 | 1378 | 24 | 87 | 10 | n | n | | |
|  | −10 | | 20 | 0 | 0 | 0 | 10 | 0 | 20 | 20 | 20 | 5 | 5 | 90 | 6.9 |
| Rat 2 | 2 | 214 | 212 | 218 | 4.23 | 12.4 | 757 | 1360 | 32 | 132 | 10 | n | n | | |
|  | −10 | | 20 | 0 | 0 | 0 | 10 | 0 | 20 | 5 | 20 | 5 | 5 | 75 | 5.8 |
| Rat 3 | 3 | 245 | 235 | 245 | 5.99 | 31.6 | 922 | 1435 | 27 | 97 | 12 | n | n | | |
|  | −10 | | 20 | 0 | 5 | 0 | 10 | 0 | 20 | 10 | 20 | 5 | 5 | 85 | 6.5 |
|  | | | | | | | | | | | | | | AVE | 6.4 |

In the e371 single dose study, compounds 18365, 18926, and 19244 were compared side by side with docetaxel. Compounds 18365, 18926, and 19244 were formulated in an ethanol, Cremophor EL® and D5W formulation (10:10:80) and docetaxel was formulated in an ethanol Tween® 80 based formulation. Compounds 18365, 18926, and 19244 all showed less axonal degeneration than docetaxel and also a higher (safer) rat toxicity score.

TABLE 25

Results from e371 single dose study

| IV Dose/Rat | Mort | Neuro Tox | Day 1 BW | Day 8 BW | Day 10 BW | Day 4 WBC | Day 10 WBC | Day 4 PLT | Day 10 PLT | Day 4 ALT | Day 4 AST | Day 4 BUN | Dia L/W | Dia B/M | Total | Score |
|---|---|---|---|---|---|---|---|---|---|---|---|---|---|---|---|---|
| 18365 12 mg/kg | | | | | | | | | | | | | | | | |
| Rat 1 | | 0 | 227 | 216 | 230 | 6.53 | 40.4 | 736 | 1070 | 18 | 65 | 13 | n | n | | |
|  | | 0 | | 20 | 0 | 5 | 0 | 20 | 0 | 20 | 20 | 20 | 5 | 5 | 115 | 8.8 |
| Rat 2 | | 0 | 231 | 213 | 231 | 6.39 | 14.6 | 777 | 849 | 17 | 59 | 13 | n | n | | |
|  | | 0 | | 20 | 0 | 5 | 0 | 20 | 0 | 20 | 20 | 20 | 5 | 5 | 115 | 8.8 |
| Rat 3 | | 0 | 240 | 211 | 220 | 4.18 | 15.2 | 770 | 1682 | 17 | 70 | 14 | n | n | | |
|  | | 0 | | 10 | 0 | 0 | 0 | 20 | 0 | 20 | 20 | 20 | 5 | 5 | 100 | 7.7 |
|  | | | | | | | | | | | | | | | AVE | 8.5 |

| IV | Neuro | Day 1 | Day 8 | Day 10 | Day 4 | Day 10 | Day 4 | Day 10 | Day 4 | Day 4 | Day 4 | Dia | Dia | Total | Score |
|---|---|---|---|---|---|---|---|---|---|---|---|---|---|---|---|
| 18926 12 mg/kg | | | | | | | | | | | | | | | |
| Rat 1 | 0 | 230 | 219 | 220 | 4.94 | 12.4 | 889 | 1359 | 28 | 84 | 11 | n | n | | |
|  | 0 | | 20 | 0 | 0 | 0 | 20 | 0 | 20 | 20 | 20 | 5 | 5 | 110 | 8.5 |
| Rat 2 | 0 | 238 | 220 | 224 | 5.97 | 14.5 | 781 | 1383 | 26 | 109 | 15 | n | n | | |
|  | 0 | | 20 | 0 | 5 | 0 | 20 | 0 | 20 | 20 | 20 | 5 | 5 | 115 | 8.8 |
| Rat 3 | 1 | 227 | 208 | 215 | 6.69 | 15.5 | 831 | 1398 | 29 | 107 | 16 | n | n | | |
|  | −10 | | 20 | 0 | 5 | 0 | 20 | 0 | 20 | 20 | 20 | 5 | 5 | 105 | 8.1 |
|  | | | | | | | | | | | | | | AVE | 8.5 |
| 19244 12 mg/kg | | | | | | | | | | | | | | | |
| Rat 1 | 1 | 231 | 204 | 212 | 7.03 | 9.26 | 693 | 1000 | 25 | 80 | 11 | n | n | | |
|  | −10 | | 10 | 0 | 5 | 0 | 10 | 0 | 20 | 20 | 20 | 5 | 5 | 85 | 6.5 |
| Rat 2 | 0 | 235 | 204 | 212 | 3.23 | 7.66 | 598 | 1181 | 18 | 91 | 12 | n | n | | |
|  | 0 | | 10 | 0 | 0 | 0 | 10 | 0 | 20 | 20 | 20 | 5 | 5 | 90 | 6.9 |
| Rat 3 | 0 | 231 | 220 | 230 | 4 | 10 | 684 | 1027 | 20 | 77 | 10 | n | n | | |
|  | 0 | | 20 | 0 | 0 | 0 | 10 | 0 | 20 | 20 | 20 | 5 | 5 | 100 | 7.7 |
|  | | | | | | | | | | | | | | AVE | 7.1 |
| Docetaxel 12 mg/kg | | | | | | | | | | | | | | | |
| Rat 1 | 1 | 226 | 211 | 223 | 6.51 | 9.6 | 735 | 906 | 30 | 115 | 11 | n | n | | |
|  | −10 | | 20 | 0 | 5 | 0 | 20 | 0 | 20 | 10 | 20 | 5 | 5 | 95 | 7.3 |
| Rat 2 | 1 | 238 | 217 | 228 | 5.15 | 7.03 | 708 | 1568 | 21 | 97 | 11 | n | n | | |
|  | −10 | | 20 | 0 | 0 | 0 | 10 | 0 | 20 | 20 | 20 | 5 | 5 | 90 | 6.9 |

TABLE 25-continued

Results from e371 single dose study

| Rat 3 | 1 | 229 | 216 | 228 | 5.42 | 12.4 | 670 | 1198 | 28 | 119 | 13 | n | n | | |
|---|---|---|---|---|---|---|---|---|---|---|---|---|---|---|---|
| | −10 | | 20 | 0 | 0 | 0 | 10 | 0 | 20 | 10 | 20 | 5 | 5 | 80 | 6.2 |
| | | | | | | | | | | | | | AVE | 6.8 |

In the e371 multiple dose study, compounds 18365, 18926, and 19244 were compared side by side with docetaxel. Compounds 18365, 18926, and 19244 were formulated in an ethanol, Cremophor EL® and D5W formulation (10:10:80) and docetaxel was formulated in an ethanol Tween® 80 based formulation. Compounds 18365 and 18926 showed less axonal degeneration than docetaxel and compound 19244 when dosed weekly was similar to docetaxel. In comparison to the single dose study, compound 18926 showed a lower score than docetaxel when dosed weekly, indicating in the clinic, compound 18926 may be better in an every three week schedule rather than a weekly schedule. However, there was no mortality in this study.

In the e346 multiple dose study, compounds 17932, 18365, 18926, and 19244 were compared side by side with docetaxel. Compounds 18365, 18926, and 19244 were formulated in an ethanol, Liposyn II 20% based formulation (5:95) and docetaxel was formulated in an ethanol, Tween® 80 based formulation. Compounds 18365, 17932, and 18926 all showed much less axonal degeneration than docetaxel. Compound 19244 when dosed weekly also showed high axonal degeneration, but was still lower than docetaxel. In comparison to the single dose studies, compound 18926 showed a lower score than docetaxel when dosed weekly, indicating in the clinic, compound 18926 may be better in an every three week schedule rather than a weekly schedule. However, there was no mortality in this study.

TABLE 26

Results from e371 multiple dose study

| IV Dose/Rat | Mort | Neuro Tox | Day 1 BW | Day 22 BW | Day 24 BW | Day 18 WBC | Day 24 WBC | Day 18 PLT | Day 24 PLT | Day 18 ALT | Day 18 AST | Day 18 BUN | Dia L/W | Dia B/M | Total | Score |
|---|---|---|---|---|---|---|---|---|---|---|---|---|---|---|---|---|
| 18365 12 mg/kg | | | | | | | | | | | | | | | | |
| Rat 1 | 1 | | 232 | 215 | 232 | 8.07 | 13 | 1119 | 1046 | 19 | 103 | 17 | n | n | | |
| | −10 | | | 20 | 0 | 10 | 0 | 20 | 0 | 20 | 20 | 20 | 5 | 5 | 110 | 8.5 |
| Rat 2 | 1 | | 233 | 229 | 244 | 3.89 | 4.04 | 991 | 867 | 36 | 94 | 12 | n | n | | |
| | −10 | | | 20 | 0 | 0 | 0 | 20 | 0 | 20 | 20 | 20 | 5 | 5 | 100 | 7.7 |
| Rat 3 | 2 | | 235 | 214 | 232 | 6.38 | 17.2 | 973 | 1341 | 23 | 96 | 10 | n | n | | |
| | −10 | | | 20 | 0 | 5 | 0 | 20 | 0 | 20 | 20 | 20 | 5 | 5 | 105 | 8.1 |
| | | | | | | | | | | | | | | AVE | 8.1 |

| IV | Neuro | Day 1 | Day 22 | Day 24 | Day 18 | Day 24 | Day 18 | Day 24 | Day 18 | Day 18 | Day 18 | Dia | Dia | | |
|---|---|---|---|---|---|---|---|---|---|---|---|---|---|---|---|
| 18926 12 mg/kg | | | | | | | | | | | | | | | | |
| Rat 1 | 1 | 216 | 179 | 196 | 4.79 | 6.88 | 1242 | 1457 | 30 | 93 | 11 | n | n | | |
| | −10 | | 5 | 0 | 5 | 0 | 20 | 0 | 20 | 20 | 20 | 5 | 5 | 90 | 6.9 |
| Rat 2 | 2 | 243 | 173 | 187 | 3.39 | 0.954 | 684 | 77.5 | 32 | 120 | 17 | y | n | | |
| | −10 | | 0 | 0 | 0 | −5 | 20 | −5 | 20 | 20 | 20 | 0 | 5 | 65 | 5.0 |
| Rat 3 | 1 | 244 | 200 | 216 | 12.2 | 8.47 | 1174 | 1502 | 31 | 219 | 17 | n | n | | |
| | −10 | | 5 | 0 | 20 | 0 | 20 | 0 | 20 | 5 | 20 | 5 | 5 | 90 | 6.9 |
| 19244 12 mg/kg | | | | | | | | | | | | | | | | |
| Rat 1 | 2 | 213 | 202 | 214 | 5.24 | 4.77 | 1019 | 768 | 24 | 95 | 15 | n | n | | |
| | −10 | | 20 | 0 | 5 | −5 | 20 | 0 | 20 | 20 | 20 | 5 | 5 | 100 | 7.7 |
| Rat 2 | 3 | 246 | 205 | 222 | 2.42 | 1.76 | 1056 | 1381 | 68 | 347 | 20 | n | n | | |
| | −10 | | 5 | 0 | 0 | −5 | 20 | 0 | 10 | 0 | 10 | 5 | 5 | 40 | 3.1 |
| Rat 3 | 3 | 237 | 229 | 241 | 4.9 | 5.4 | 1000 | 1161 | 27 | 92 | 11 | n | n | | |
| | −10 | | 20 | 0 | 5 | 0 | 20 | 0 | 20 | 20 | 20 | 5 | 5 | 105 | 8.1 |
| | | | | | | | | | | | | | | AVE | 6.3 |
| Docetaxel 12 mg/kg | | | | | | | | | | | | | | | | |
| Rat 1 | 3 | 249 | 230 | 244 | 4.03 | 9.27 | 758 | 1192 | 28 | 101 | 19 | n | n | | |
| | −10 | | 20 | 0 | 0 | 0 | 20 | 0 | 20 | 20 | 20 | 5 | 5 | 100 | 7.7 |
| Rat 2 | 3 | 212 | 215 | 228 | 3.54 | 8.23 | 720 | 1120 | 33 | 126 | 12 | n | n | | |
| | −10 | | 20 | 0 | 0 | 0 | 20 | 0 | 20 | 20 | 20 | 5 | 5 | 100 | 7.7 |
| Rat 3 | 3 | 236 | 225 | 250 | 5 | 7.57 | 742 | 1058 | 34 | 131 | 19 | n | n | | |
| | −10 | | 20 | 0 | 5 | 0 | 20 | 0 | 20 | 20 | 20 | 5 | 5 | 105 | 8.1 |
| | | | | | | | | | | | | | | AVE | 7.8 |

TABLE 27

Results from e346 multiple dose study

| IV Dose/Rat | Mortality | Neuro Tox | Day 1 BW | Day 22 BW | Day 24 BW | Day 18 WBC | Day 24 WBC | Day 18 PLT | Day 24 PLT | Day 18 ALT | Day 18 AST | Day 18 BUN | Dia L/W | Dia B/M | Total | Score |
|---|---|---|---|---|---|---|---|---|---|---|---|---|---|---|---|---|
| 17932 12 mg/kg | | | | | | | | | | | | | | | | |
| Rat 1 | | 0 | 250 | 190 | 193 | 5.2 | 28 | 546 | 1134 | 38 | 164 | 16 | n | n | | |
| | | 0 | | 0 | 0 | 0 | 0 | 10 | 0 | 20 | 10 | 20 | 5 | 5 | 70 | 5.4 |
| Rat 2 | | 1 | 231 | 185 | 199 | 5.04 | 6.15 | 1083 | 1329 | 28 | 142 | 12 | n | n | | |
| | | −10 | | 5 | 0 | 0 | 0 | 20 | 0 | 20 | 20 | 20 | 5 | 5 | 85 | 6.5 |
| Rat 3 | | 0 | 230 | 168 | 188 | 4.52 | 4.49 | 627 | 1010 | 38 | 144 | 11 | n | n | | |
| | | 0 | | 0 | 0 | 0 | −5 | 10 | 0 | 20 | 20 | 20 | 5 | 5 | 75 | 5.8 |
| | | | | | | | | | | | | | | | AVE | 5.9 |

| IV | Neuro | Day 1 | Day 22 | Day 24 | Day 18 | Day 24 | Day 18 | Day 24 | Day 18 | Day 18 | Day 18 | Dia | Dia | | |
|---|---|---|---|---|---|---|---|---|---|---|---|---|---|---|---|
| 18365 12 mg/kg | | | | | | | | | | | | | | | |
| Rat 1 | 2 | 214 | 201 | 216 | 4.03 | 7.03 | 699 | 1270 | 36 | 162 | 10 | n | n | | |
| | −10 | | 20 | 0 | 0 | 0 | 20 | 0 | 20 | 10 | 20 | 5 | 5 | 90 | 6.9 |
| Rat 2 | 1 | 236 | 226 | 232 | 4.68 | 6.24 | 772 | 1053 | 31 | 153 | 9 | n | n | | |
| | −10 | | 20 | 0 | 0 | 0 | 20 | 0 | 20 | 20 | 20 | 5 | 5 | 100 | 7.7 |
| Rat 3 | 0 | 260 | 230 | 241 | 7.36 | 14.4 | 751 | 1305 | 377 | 276 | 9 | n | n | | |
| | 0 | | 10 | 0 | 0 | 0 | 20 | 0 | 0 | 0 | 20 | 5 | 5 | 60 | 4.6 |
| | | | | | | | | | | | | | | AVE | 6.4 |
| 18926 12 mg/kg | | | | | | | | | | | | | | | |
| Rat 1 | 1 | 222 | 156 | 166 | 4.74 | 12.3 | 611 | 520 | 60 | 237 | 18 | n | n | | |
| | −10 | | 0 | 0 | 0 | 0 | 10 | −5 | 20 | 5 | 10 | 5 | 5 | 40 | 3.1 |
| Rat 2 | 0 | 227 | 160 | 169 | 3.3 | 11.4 | 772 | 1009 | 102 | 389 | 18 | n | n | | |
| | 0 | | 0 | 0 | 0 | 0 | 20 | 0 | 10 | 0 | 10 | 5 | 5 | 50 | 3.8 |
| Rat 3 | 1 | 255 | 168 | 176 | 4.93 | 10.2 | 943 | 276 | 49 | 283 | 16 | n | n | | |
| | −10 | | 0 | 0 | 0 | 0 | 20 | −5 | 20 | 0 | 20 | 5 | 5 | 55 | 4.2 |
| | | | | | | | | | | | | | | AVE | 3.7 |
| 19244 12 mg/kg | | | | | | | | | | | | | | | |
| Rat 1 | 3 | 226 | 198 | 208 | 3.3 | 7.1 | 724 | 940 | 30 | 143 | 9 | n | n | | |
| | −10 | | 10 | 0 | 0 | 0 | 20 | 0 | 20 | 20 | 20 | 5 | 5 | 90 | 6.9 |
| Rat 2 | 3 | 244 | 201 | 216 | 3.79 | 3.11 | 1221 | 653 | 31 | 117 | 10 | n | n | | |
| | −10 | | 5 | 0 | 0 | −5 | 20 | −5 | 20 | 20 | 20 | 5 | 5 | 75 | 5.8 |
| Rat 3 | 3 | 233 | 184 | 196 | 3.97 | 9.13 | 980 | 1531 | 64 | 158 | 11 | n | n | | |
| | −10 | | 0 | 0 | 0 | 0 | 20 | 0 | 20 | 10 | 20 | 5 | 5 | 70 | 5.4 |
| | | | | | | | | | | | | | | AVE | 6.0 |
| Paclitaxel 12 mg/kg | | | | | | | | | | | | | | | |
| Rat 1 | 1 | 233 | 251 | 260 | 10.8 | 10.2 | 1005 | 999 | 75 | 274 | 17 | n | n | | |
| | −10 | | 20 | 0 | 5 | −5 | 20 | 0 | 20 | 0 | 20 | 5 | 5 | 80 | 6.2 |
| Rat 2 | 2 | 235 | 261 | 269 | 11.2 | 18.3 | 1153 | 1358 | 58 | 158 | 19 | n | n | | |
| | −10 | | 20 | 0 | 5 | 0 | 20 | 0 | 20 | 10 | 10 | 5 | 5 | 85 | 6.5 |
| Rat 3 | 2 | 231 | 251 | 266 | 9.05 | 14.5 | 924 | 1084 | 32 | 112 | 15 | n | n | | |
| | −10 | | 20 | 0 | 5 | 0 | 20 | 0 | 20 | 20 | 20 | 5 | 5 | 105 | 8.1 |
| | | | | | | | | | | | | | | AVE | 6.9 |
| Docetaxel 12 mg/kg | | | | | | | | | | | | | | | |
| Rat 1 | 4 | 248 | 220 | 235 | 3.07 | 11.9 | 885 | 1544 | 24 | 95 | 15 | n | n | | |
| | −10 | | 10 | 0 | 0 | 0 | 20 | 0 | 20 | 20 | 20 | 5 | 5 | 90 | 6.9 |
| Rat 2 | 4 | 230 | 224 | 234 | 3.06 | 6.72 | 889 | 1368 | 27 | 162 | 13 | n | n | | |
| | −10 | | 0 | 0 | 0 | 0 | 20 | 0 | 20 | 10 | 20 | 5 | 5 | 90 | 6.9 |
| Rat 3 | 4 | 221.8 | 211 | 225 | 3 | 12.6 | 492 | 1231 | 35 | 182 | 10 | n | n | | |
| | −10 | | 20 | 0 | 0 | 0 | 10 | 0 | 20 | 10 | 20 | 5 | 5 | 80 | 6.2 |
| | | | | | | | | | | | | | | AVE | 6.7 |

What is claimed is:

1. A taxane having the structure (1):

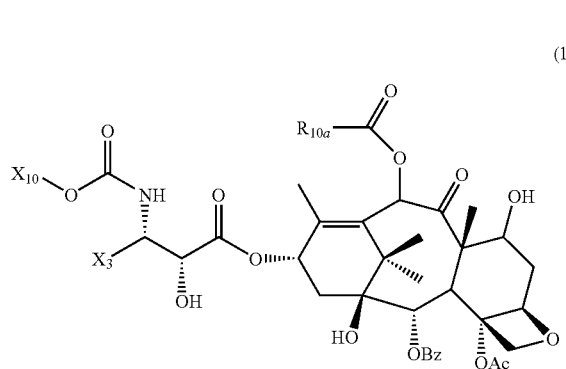

(1)

wherein $R_{10a}$ is ethyl or cyclopropyl; $X_3$ is thienyl; and $X_{10}$ is cyclobutyl or cyclopentyl.

2. The taxane of claim 1, the taxane having a structure selected from (1AA), (1BB), (1CC), and (1DD):

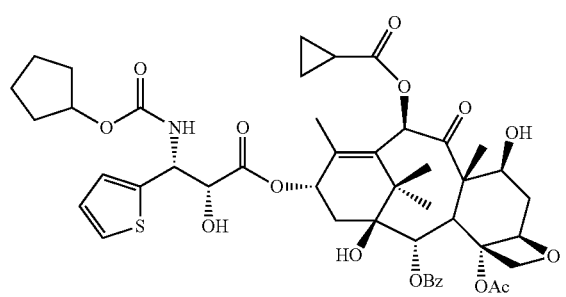

(1AA)

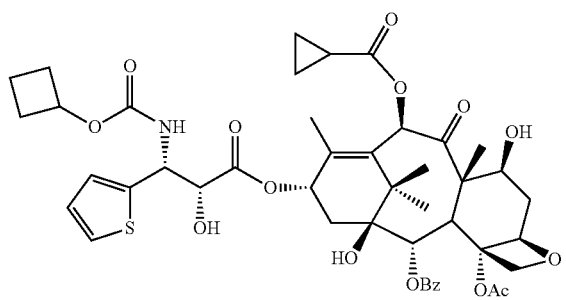

(1BB)

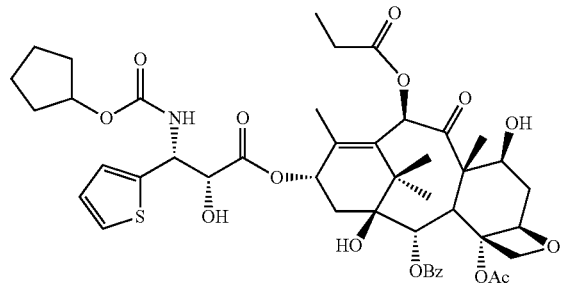

(1CC)

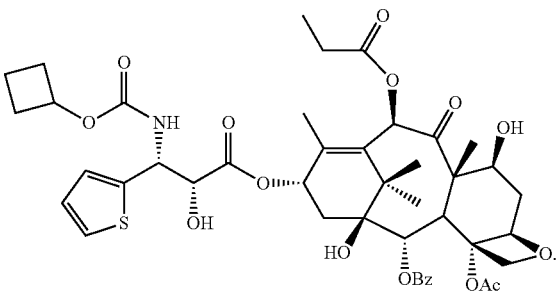

(1DD)

3. A pharmaceutical composition comprising a taxane having the structure (1):

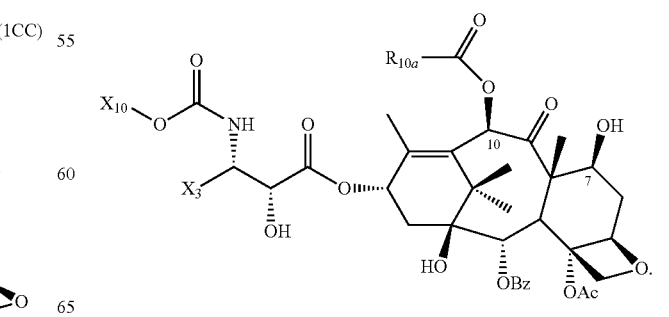

(1)

and at least one pharmaceutically acceptable carrier, wherein $R_{10a}$ is ethyl or cyclopropyl; $X_3$ is thienyl; and $X_{10}$ is cyclobutyl or cyclopentyl.

4. The pharmaceutical composition of claim 3 wherein the taxane has the structure (1bb):

(1bb)

5. The pharmaceutical composition of claim 3 wherein the taxane has a strcture selected from (1A), (1B), (1C), and (1D):

(1A)

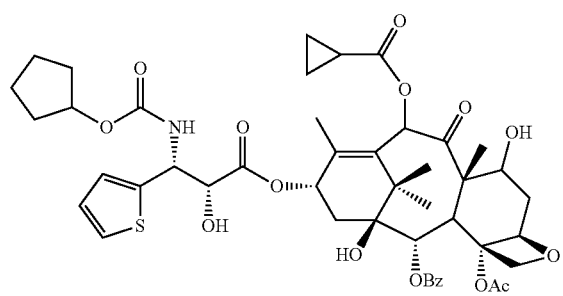

(1B)

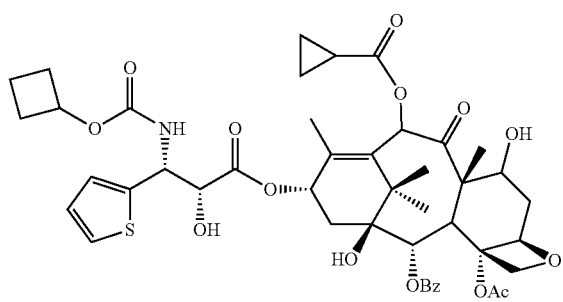

(1C)

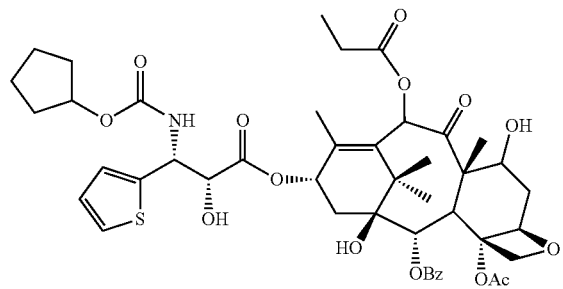

(1D)

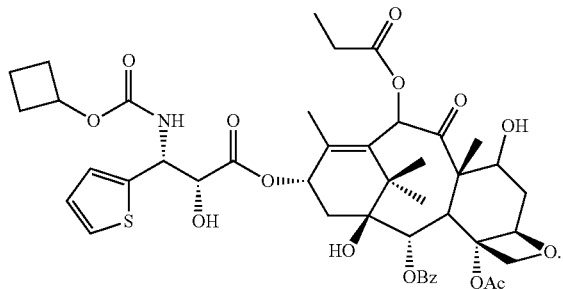

6. The pharmaceutical composition of claim 3 wherein the taxane has a structure selected from (1AA), (1BB), (1CC), and (1DD):

(1AA)

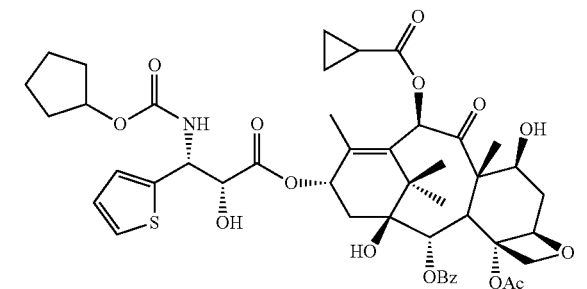

(1BB)

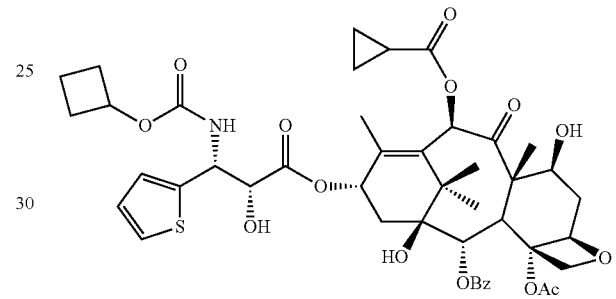

(1CC)

(1DD)

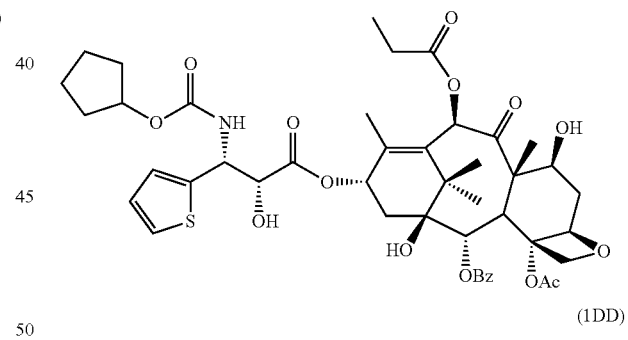

7. A method of inhibiting tumor growth in a mammal, said method comprising administering to the mammal a therapeutically effective amount of a pharmaceutical composition comprising the taxane of claim 1.

8. The method of claim 7 wherein the taxane has a structure selected from (1AA), (1BB), (1CC), and (1DD):

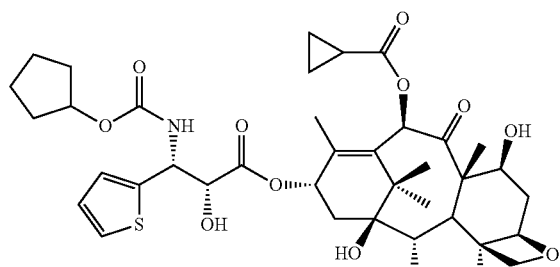
(1AA)

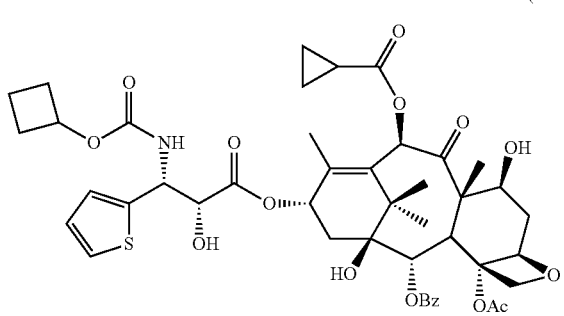
(1BB)

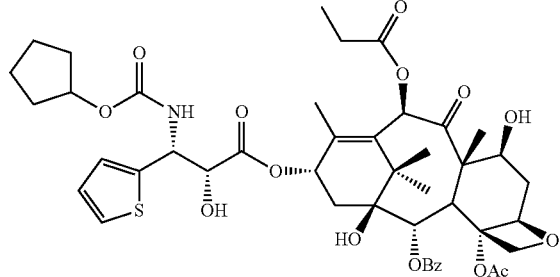
(1CC)

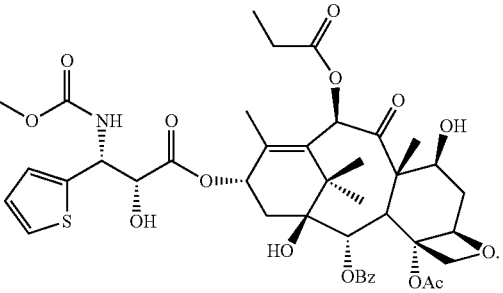
(1DD)

9. The method of claim 7 wherein the tumor includes tumor cells exhibiting multidrug resistance.

10. The method of claim 9 wherein the multidrug resistant tumor cells overexpress a drug-efflux transporter.

11. The method of claim 10 wherein the drug-efflux transporter is an ATP-binding cassette transporter.

12. The method of claim 11 wherein the ATP-cassette transporter is P-glycoprotein, an MDR-associated protein, a breast cancer resistance protein, a multidrug resistance-associated protein, or a combination thereof.

13. The method of claim 7 wherein the tumor is resistant to paclitaxel.

14. The method of claim 7 wherein the tumor is resistant to docetaxel.

15. The method of claim 7 wherein the tumor is an epithelial cell carcinoma.

16. The method of claim 7 wherein the tumor is a brain glioblastoma, a breast carcinoma, a colon carcinoma, a kidney carcinoma, a liver carcinoma, a lung carcinoma, an ovarian carcinoma, a pancreatic carcinoma, a renal carcinoma, or a skin melanoma.

17. The method of claim 7 wherein the tumor is a colon carcinoma, a lung carcinoma, a pancreatic carcinoma, a renal carcinoma, or a skin melanoma.

18. The method of claim 7 wherein the tumor is a colon carcinoma, a lung carcinoma, a renal carcinoma, or a skin melanoma.

19. The method of claim 7 wherein the tumor is SNB-19 brain glioblastoma, HCT116 colon carcinoma, HT-29 colon carcinoma, DLD-1 colon carcinoma, A549 lung carcinoma, HOP-18 lung carcinoma, MSTO-211H mesothelioma, A375 melanoma, MALME-3 melanoma, SK-MEL-28 melanoma, OVCAR4 ovarian carcinoma, OVCAR5 ovarian carcinoma, PANC-1 pancreatic adenocarcinoma, BxPC-3 pancreatic carcinoma, 786-0 renal carcinoma, or TK-10 renal carcinoma.

20. The method of claim 7 wherein the tumor is DLD-1 colon carcinoma, MSTO-211H mesothelioma, A375 melanoma, or 786-0 renal carcinoma.

* * * * *